United States Patent
Bradbury et al.

(10) Patent No.: US 11,931,425 B2
(45) Date of Patent: *Mar. 19, 2024

(54) METHODS OF TREATMENT USING ULTRASMALL NANOPARTICLES TO INDUCE CELL DEATH OF NUTRIENT-DEPRIVED CANCER CELLS VIA FERROPTOSIS

(71) Applicants: Memorial Sloan Kettering Cancer Center, New York, NY (US); Cornell University, Ithaca, NY (US)

(72) Inventors: Michelle S. Bradbury, New York, NY (US); Ulrich Wiesner, Ithaca, NY (US); Michael Overholtzer, Glen Ridge, NJ (US); Howard Scher, Tenafly, NJ (US); Kai Ma, Ithaca, NY (US)

(73) Assignees: Memorial Sloan Kettering Cancer Center, New York, NY (US); Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/566,015

(22) Filed: Dec. 30, 2021

(65) Prior Publication Data
US 2022/0118106 A1 Apr. 21, 2022

Related U.S. Application Data

(63) Continuation of application No. 16/902,577, filed on Jun. 16, 2020, now Pat. No. 11,246,946, which is a continuation of application No. 15/573,855, filed as application No. PCT/US2016/034351 on May 26, 2016, now Pat. No. 10,736,972.

(60) Provisional application No. 62/280,960, filed on Jan. 20, 2016, provisional application No. 62/168,636, filed on May 29, 2015.

(51) Int. Cl.
A61K 47/69 (2017.01)
A61K 38/22 (2006.01)
A61K 47/60 (2017.01)

(52) U.S. Cl.
CPC .......... *A61K 47/6929* (2017.08); *A61K 38/22* (2013.01); *A61K 47/60* (2017.08); *A61K 47/6923* (2017.08)

(58) Field of Classification Search
None
See application file for complete search history.

(56) References Cited

U.S. PATENT DOCUMENTS

| | | |
|---|---|---|
| 3,867,519 A | 2/1975 | Michaels |
| 3,870,791 A | 3/1975 | Haddad et al. |
| 4,051,842 A | 10/1977 | Hazel et al. |
| 4,136,177 A | 1/1979 | Lin et al. |
| 4,140,122 A | 2/1979 | Kuhl et al. |
| 4,255,415 A | 3/1981 | Chrai et al. |
| 4,383,529 A | 5/1983 | Webster |
| 4,688,506 A | 8/1987 | van Breems |
| 4,713,224 A | 12/1987 | Tamhankar et al. |
| 4,774,339 A | 9/1988 | Haugland et al. |
| 4,788,603 A | 11/1988 | Fujimura et al. |
| 4,810,636 A | 3/1989 | Corey |
| 4,812,409 A | 3/1989 | Babb et al. |
| 4,931,279 A | 6/1990 | Bawa et al. |
| 5,187,288 A | 2/1993 | Kang et al. |
| 5,248,782 A | 9/1993 | Haugland et al. |
| 5,274,113 A | 12/1993 | Kang et al. |
| 5,433,896 A | 7/1995 | Kang et al. |
| 5,776,427 A | 7/1998 | Thorpe et al. |
| 5,830,912 A | 11/1998 | Gee et al. |
| 5,985,877 A | 11/1999 | Dionne et al. |
| 6,254,852 B1 | 7/2001 | Glajch et al. |
| 6,268,222 B1 | 7/2001 | Chandler et al. |
| 7,601,355 B2 | 10/2009 | Howard et al. |
| 8,084,001 B2 | 12/2011 | Burns et al. |
| 8,239,007 B2 | 8/2012 | Voegele et al. |
| 8,298,677 B2 | 10/2012 | Wiesner et al. |
| 8,389,679 B2 | 3/2013 | Eckert et al. |
| 8,409,876 B2 | 4/2013 | Wiesner et al. |
| 8,961,825 B2 | 2/2015 | Wiesner et al. |
| 9,625,456 B2 | 4/2017 | Bradbury et al. |

(Continued)

FOREIGN PATENT DOCUMENTS

| | | |
|---|---|---|
| CN | 106659797 A | 5/2017 |
| WO | WO-99/22026 A1 | 5/1999 |

(Continued)

OTHER PUBLICATIONS

Bai, T. et al., Haloperidol, a sigma receptor 1 antagonist, promotes ferroptosis in hepatocellular carcinoma cells, Biochemical and Biophysical Research Communications, 491(4):919-925, (2017).
Ballou, B. et al., Sentinel Lymph Node Imaging Using Quantum Dots in Mouse Tumor Models, Bioconjugate Chem. 18:389-396 (2007).
Benezra, M. et al., Targeted multimodal silica nanoparticles with efficient urinary excretion for nanomedicine, Cancer Research, 64(7), one page (2009).

(Continued)

*Primary Examiner* — Danah Al-Awadi
(74) *Attorney, Agent, or Firm* — Choate, Hall & Stewart LLP; William R. Haulbrook; Margo R. Monroe

(57) ABSTRACT

Described herein is a method of induced cell death via ferroptosis by nanoparticle ingestion. Moreover, the present disclosure describes the administration of high concentrations of ultrasmall nanoparticles at multiple times over the course of treatment in combination with a nutrient-depleted environment, thereby modulating cellular metabolic pathways to induce cell death by the mechanism ferroptosis. Ferroptosis involves iron, reactive oxygen species, and a synchronous mode of cell death execution.

19 Claims, 52 Drawing Sheets

(56) References Cited

U.S. PATENT DOCUMENTS

| | | | |
|---|---|---|---|
| 9,999,694 | B2 | 6/2018 | Bradbury et al. |
| 10,039,847 | B2 | 8/2018 | Bradbury et al. |
| 10,111,963 | B2 | 10/2018 | Yoo et al. |
| 10,485,881 | B2 | 11/2019 | Bradbury et al. |
| 10,548,997 | B2 | 2/2020 | Bradbury et al. |
| 10,548,998 | B2 | 2/2020 | Bradbury et al. |
| 11,559,591 | B2 | 1/2023 | Bradbury et al. |
| 2003/0219785 | A1 | 11/2003 | Hallahan et al. |
| 2004/0101822 | A1 | 5/2004 | Wiesner et al. |
| 2004/0248856 | A1 | 12/2004 | Lanza et al. |
| 2006/0106306 | A1 | 5/2006 | Essner et al. |
| 2006/0173362 | A1 | 8/2006 | Toms et al. |
| 2006/0183246 | A1 | 8/2006 | Wiesner et al. |
| 2006/0245971 | A1 | 11/2006 | Burns et al. |
| 2006/0251726 | A1 | 11/2006 | Lin et al. |
| 2008/0097225 | A1 | 4/2008 | Tearney et al. |
| 2008/0139787 | A1 | 6/2008 | De Jesus et al. |
| 2008/0213377 | A1 | 9/2008 | Bhatia et al. |
| 2008/0292556 | A1 | 11/2008 | Texier-Nogues et al. |
| 2010/0261208 | A1 | 10/2010 | Schollhorn |
| 2010/0262017 | A1 | 10/2010 | Frangioni |
| 2011/0028662 | A1 | 2/2011 | Wiesner et al. |
| 2012/0107237 | A1 | 5/2012 | Miao et al. |
| 2013/0017265 | A1 | 1/2013 | Farokhzad et al. |
| 2013/0039848 | A1 | 2/2013 | Bradbury et al. |
| 2014/0028210 | A1 | 1/2014 | Maxik et al. |
| 2014/0248210 | A1 | 9/2014 | Bradbury et al. |
| 2015/0174268 | A1 | 6/2015 | Li |
| 2015/0182118 | A1 | 7/2015 | Bradbury et al. |
| 2015/0343091 | A1 | 12/2015 | Yoo et al. |
| 2015/0366995 | A1 | 12/2015 | Wiesner et al. |
| 2016/0018404 | A1 | 1/2016 | Iyer et al. |
| 2016/0202185 | A1 | 7/2016 | Zhuang et al. |
| 2017/0239378 | A1 | 8/2017 | Bradbury et al. |
| 2017/0326261 | A1 | 11/2017 | Oukhatar et al. |
| 2018/0093000 | A1 | 4/2018 | Bradbury et al. |
| 2018/0133346 | A1 | 5/2018 | Wiesner et al. |
| 2018/0169264 | A1 | 6/2018 | Bradbury et al. |
| 2018/0326103 | A1 | 11/2018 | Bradbury et al. |
| 2019/0070310 | A1 | 3/2019 | Bradbury et al. |
| 2020/0101180 | A1 | 4/2020 | Bradbury et al. |
| 2020/0179538 | A1 | 6/2020 | Ma et al. |
| 2020/0289668 | A1 | 9/2020 | Bradbury et al. |
| 2020/0316219 | A1 | 10/2020 | Bradbury et al. |
| 2020/0376149 | A1 | 12/2020 | Bradbury et al. |
| 2020/0383943 | A1 | 12/2020 | Bradbury et al. |
| 2021/0145985 | A1 | 5/2021 | Bradbury et al. |
| 2023/0158180 | A1 | 5/2023 | Bradbury et al. |

FOREIGN PATENT DOCUMENTS

| | | |
|---|---|---|
| WO | WO-2004/074504 A2 | 9/2004 |
| WO | WO-2004/108902 A2 | 12/2004 |
| WO | WO-2006/099445 A2 | 9/2006 |
| WO | WO-2007/002540 A2 | 1/2007 |
| WO | WO-2007/136413 A2 | 11/2007 |
| WO | WO-2007/149062 A2 | 12/2007 |
| WO | WO-2008/044138 A1 | 4/2008 |
| WO | WO-2008/142571 A2 | 11/2008 |
| WO | WO-2009/029870 A2 | 3/2009 |
| WO | WO-2009/064964 A2 | 5/2009 |
| WO | WO-2011/003109 A1 | 1/2011 |
| WO | WO-2011/084620 A2 | 7/2011 |
| WO | WO-2011/130598 A1 | 10/2011 |
| WO | WO-2013/087734 A2 | 6/2013 |
| WO | WO-2013/192609 A1 | 12/2013 |
| WO | WO-2014/011973 A2 | 1/2014 |
| WO | WO-2014/145606 A1 | 9/2014 |
| WO | WO-2015/103420 A1 | 7/2015 |
| WO | WO-2015/183882 A1 | 12/2015 |
| WO | WO-2016/015044 A1 | 1/2016 |
| WO | WO-2016/100340 A1 | 6/2016 |
| WO | WO-2016/164578 A1 | 10/2016 |
| WO | WO-2016/196201 A1 | 12/2016 |
| WO | WO-2017/044701 A1 | 3/2017 |
| WO | WO-2018/102372 A1 | 6/2018 |
| WO | WO-2018/191316 A1 | 10/2018 |
| WO | WO-2018/213851 A1 | 11/2018 |
| WO | WO-2018/217528 A1 | 11/2018 |
| WO | WO-2018/218087 A1 | 11/2018 |
| WO | WO-2018/237253 A1 | 12/2018 |
| WO | WO-2019/113004 A1 | 6/2019 |

OTHER PUBLICATIONS

Benezra, M. et al., Ultrasmall Integrin-Targeted Silica Nanoparticles Modulate Signaling Events and Cellular Processes in a Concentration-Dependent Manner, Small, 11(14):1721-1732 (2015).

Benezra, M. et al., Multimodal silica nanoparticles are effective cancer-targeted probes in a model of human melanoma, Journal of Clinical Investigation, 121(7):2768-2780(2011).

Bogush, G. H. et al., Preparation of Monodisperse Silica Particles: Control of Size and Mass Fraction, J. Non-Cryst. Solids, 104:95-106 (1988).

Brien, J. F. et al., A Study of the Calcium Carbimide-Ethanol Interaction in Man, Europ. J. Clin. Pharmacol. 14(2):133-41 (1978).

Brülisauer, L. et al., Disulfide-containing parenteral delivery systems and their redox- biological fate, Journal of Controlled Release, 195:147-154 (2014).

Burns, et al., Fluorescent Silica Nanoparticles with Efficient Urinary Excretion for Nanomedicine, Nano Letters 9(1):442-8 (2009).

Chakraborty, M. et al., External Beam Radiation of Tumors Alters Phenotype of Tumor Cells to Render Them Susceptible to Vaccine-Mediated T-Cell Killing, Cancer Research, 64:4328-4337 (2004).

Chen, F. et al., In Vivo Integrity and Biological Fate of Chelator-Free Zirconium-89 Labeled Mesoporous Silica Nanoparticles, ACSNANO, 8(9):7950-7959, (2015).

Chen, F et al., Target-or-Clear Zirconium-89 Labeled Silica Nanoparticles for Enhanced Cancer-Directed Uptake in Melanoma: A Comparison of Radiolabeling Strategies, Chemistry of Materials, 29(19):8269-8281 (2017).

Cho, Y. S. et al., Cetuximab-conjugated magneto-fluorescent silica nanoparticles for in vivo colon cancer targeting and imaging, Cancer Letters, 299:63-71 (2010).

Choi, Y. J. et al., Combined inhibition of IGFR enhances the effects of getfitinib in H1650: a lung cancer cell line with EGFR mutation and primary resistance to EGFR-TK inhibitors, Cancer Cehmother Pharmacol, 66:381-388 (2010).

Crespi, M. D. et al., Mitroxantrone Affects Topoisomerase Activities In Human Breast Cancer Cells, Biochemical and Biophysical Research Communications, 136(2):521-8 (1986).

Cressman, S. et al., Binding and Uptake of RGD-Containing Ligands to Cellular $\alpha V^{\beta}3$ Integrins, Int J Pept Res Ther, 15:49-59 (2009).

Cristy, M. and Eckerman, K. F., Specific absorbed fractions of energy at various ages from internal photon sources (I-VII). Oak Ridge National Laboratory Report ORNL/TM-8381N1-7. Springfield, VA: National Technical Information Service, Dept. of Commerce (1987).

Crow, R. T. and Crothers, D. M., Inhibition of Topoisomerase I by Anthracycline Antibiotics: Evidence for General Inhibition of Topoisomerase I by DNA-Binding Agents, J. Med. Chem. 37(19):3191-3194 (1994).

Database Biosis [online] Biosciences Information Service, Von Angerer, E. et al., The Effect of a Combination of Zindoxifene and Cisplatin on Dunning R3327-G Prostatic Carcinomas of the Rat, XP002788768, Database Accession No. PREV199294042193, abstract and Journal of Cancer Research and Clinical Oncology, 118(5):339-343, (1992).

Database Medline [online], US National Library of Medicine (NLM), Urakami, S. et al., Long-term control or possible cure? Treatment of stage D2 prostate cancer under chemotherapy using cisplatin and estramustine phosphate followed by maximal androgen blockade, XP002788770, Database accession No. NLM18092143 abstract & International Urology and Nephrology, 40(2):365-368, (2008).

Database Medline, [online] U.S. National Library of Medicine (Nlm), Klump, R. et al., Radiotherapy and concomitant chemoradiotherapy in the NB rat prostate adenocarcinoma model,

(56) References Cited

OTHER PUBLICATIONS

XP002788769, Database accession No. NLM2519835 abstract, & In Vivo (Athens, Greece), 3(2):109-111, (1989).
De Jong, M. et al., Comparison of 111In-Labeled Somatostatin Analogues for Tumor Scintigraphy and Radionuclide Therapy, Cancer Res., 58:437-41 (1998).
De Jong, M. et al., Internalization of radiolabelled [DTPA$^0$]octreotide and [DOTA0, Tyr$^3$]ocetreotide:peptides for somatostatin receptor-targeted scintigraphy and radionuclide therapy, Nucl. Med. Commun., 19(3):283-288 (1998).
Denny, W. A. and Baguley, B. C., Dual Topoisomerase I/II Inhibitors in Cancer Therapy, Curr. Top. Med. Chem., 3(3):339-353 (2003).
Detappe, A. et al., Advanced multimodal nanoparticles delay tumor progression with clinical radiation therapy, Journal of Controlled Release, 238:103-113 (2016).
Ding, Y. et al., The performance of thiol-terminated PEG-paclitaxel-conjugated gold nanoparticles, Biomaterials, 34:10217-10227 (2013).
Dixon, S. J. et al., Ferroptosis: An Iron-Dependent Form of Nonapoptotic Cell Death, Cell, 149(51):1060-1072 (2012).
Doronina, S. O. et al., Novel Peptide Linkers for Highly Potent Antibody Auristatin Conjugate, Bioconjugate Chem., 19(10):1960-1963, (2008).
Etrych, T. et al., Biodegradable start HPMA polymer-drug conjugates: Biodegradability, distribution and anti-tumor efficacy, Journal of Controlled Release, 154:241-248 (2011).
European Extended Search Report, Application No. 14763612.0, 10 pages, dated Oct. 19, 2016.
European Extended Search Report, Application No. 17165118.5, 6 pages, dated Jul. 19, 2017.
Foglesong, P. D. et al., Doxorubicin inhibits human DNA topoisomerase I, Cancer Chemother. Pharmacol., 30(2):123-125 (1992).
Frauwirth, K. A. and Thompson, C. B., Activation and inhibition of lymphocytes by costimulation, The Journal of clinical Investigation, 109(3):295-299 (2002).
Fuller, , J. E. et al., Intracellular delivery of core-shell fluorescent silica nanoparticles, Science Direct, Biomaterials, 29:1526-1532 (2008).
Gatto, B. et al., Identification of Topoisomerase I as the Cytotoxic Target of the Protoberberine Alkaloid Coralyne, Cancer Res., 15(12):2795-2800 (1996).
Gladson, C. A. and Cheresh, D. A., Glioblastoma Expression of Vitronectin and Alpha v Beta 3 Integrin, Adhesion Mechanism for Transformed Glial Cells, J. Clin. Invest. 88:1924-1932 (1991).
Goel, S. et al. VEGF121-Conjugated Mesoporous Silica Nanoparticle: A Tumor Targeted Drug Delivery System, ACS Applied Materials & Interfaces, 6:21677-21685, (2014).
Guo, Jipeng et al., Ferroptosis: A Novel Anti-tumor Action for Cisplatin, Cancer Research Treatment, 50(2):445-460. (2018).
Herz, E. et al., Large Stokes-Shift Fluorescent Silica Nanoparticles with Enhanced Emission over Free Dye for Single Excitation Multiplexing, Macromol Rapid Commun., 30(22): 1907-1910 (2009).
Hilderbrand, S. A. and Weissleder, R., Near-infrared fluorescence: application to in vivo molecular imaging, Curr. Opin. Chem. Bioi., 14:71-9 (2010).
International Search Report, PCT/US2016/034351 (Methods of Treatment Using Ultrasmall Nanoparticles To Induce Cell Death of Nutrient-Deprived Cancer Cells Via Ferroptosis, filed May 26, 2016), issued by ISA/EPO, 6 pages, dated Aug. 23, 2016.
Ito et al., Pharmacokinetics 101, Paediatr Child Health, 16(9):535-536, (2011).
Kalbasi, A. et al., Radiation and immunotherapy: a synergistic combination, Clinical review, The Journal of Clinical Investigation, 127(7):2756-2763 (2013).
Kasukabe, T. et al., Combined treatment with cotylenin A and phenethyl isothiocyanate induces strong antitumor activity mainly through the induction of ferroptotic cell death in human pancreatic cancer cells, Oncology Reports, 36(2):968-976, (2016).
Kim, D. et al., Antitumor activity of sorafenib-incorporated nanoparticles of dextran/poly (dl-lactide-co-glycolide) block copolymer, Nanoscale Research Letters, 7(1):91 (2012).
Kim, S. E. et al., Ultrasmall nanoparticles induce ferroptosis in nutrient-deprived cancer cells and suppress tumour growth, Nature Nanotechnology, 11(11):977-985, (2016).
Kim, S. et al., Near-infrared fluorescent type II quantum dots for sentinel lymph node mapping, Nature Biotechnology 22(1):93-97 (2004).
Kim, Y. H. et al., In situ vaccination against mycosis fungoides by intratumoral injection of a TLR9 agonist combined with radiation: a phase 1/2 study, Blood, 119(2):355-363 (2012).
Klump, R. et al., Radiotherapy and Concomitant Chemoradiotherapy in the NB Rat Prostate Adenocarcinoma Model, in vivo, International Journal of In Vivo Research, 3(2):109-112, (1989).
Koole et al., Paramagnetic lipid-coated silica nanoparticles with a fluorescent quantum dot core: a new contrast agent platform for multimodality imaging, Bioconjugate Chem., 19(12):2471-2479 (2008).
Krenning, E. P. et al., Somatostatin Receptor Scintigraphy with Indium-111-DTPA-D-Phe-1-Octreolide in Man: Metabolism, Dosimetry and Comparison with Iodine-123-Tyr-3-Octreotide, J Nucl. Med. 33:652-8 (1992).
Lachaier, E. et al., Sorafenib Induces Ferroptosis in Human Cancer Cell Lines Originating from Different Solid Tumors, Anticancer Research, 34:6417-6422 (2014).
Larson, D. R et al., Silica Nanoparticle Architecture Determines Radiative Properties of Encapsulated Fluorophores, Chem. Mater. 20:2677-2684 (2008).
Lee. G. Y. et al., Theranostic Nanoparticles with Controlled Release of Gemcitabine for Targeted Therapy and MRI of Pancreatic Cancer, ACS NANO, 7(3):2078-2089, (2013).
Lewis et al. Comparison of Four 64Cu-labeled Somatostatin Analogs in Vitro and in a Tumor-Bearing Rat Model: Evaluation of New Derivatives for Positron Emission Imaging and Targeted Radiotherapy. J Med Chem., 42:1341-7 (1999).
Lin et al., In Vitro Toxicity of Silica Nanoparticles in Human Lung Cancer Cells, Toxicology and Applied Pharmacology, 217:252-259, (2006).
Li, T. et al., Human Topoisomerase I Poisoning by Protoberberines: Potential Roles for Both Drug-DNA and Drug-Enzyme Interactions, Biochemistry, 39(24):7107-7116 (2000).
Li, Z. et al., $^{64}$Cu-labeled Tetrameric and Octomeric RGD Peptides for Small-Animal PET of Tumor $\alpha v^\beta 3$ Integrin Expression, J. Nucl Med. 48:1162-1171 (2007).
Loir, B. et al., Expression of the MC1 Receptor Gene in Normal and Malignant Human Melanocytes. A Semiquantitative RT-PCR Study, Cell Mol. Biol., 45(7):1083-1092 (1999).
Lu, J. et al., Biocompatibility, Biodistribution, and Drug-Delivery Efficiency of Mesoporous Silica Nanoparticles for Cancer Therapy in Animals, Small, 6(16):1794-1805, (2010).
Ma, K. et al., Control of Ultrasmall Sub-10 nm Ligand-Functionalized Fluorescent Core-Shell Silica Nanoparticle Growth in Water, Chem. Mater., 27:4119-4133, (2015).
Ma, Kai and Wiesner, Ulrich, Modular and Orthogonal Post-PEGylation Surface Modifications by Insertion Enabling Penta-Functional Ultrasmall Organic-Silica Hybrid Nanoparticles, Chem. Mater., 29:6840?6855, (2017).
Ma, S. et al., Ferroptosis and autophagy induced cell death occur independently after siramesine and lapatinib treatment in breast cancer cells, PLOS ONE, 12(8):e0182921, 14 pages, (2017).
Ma, S. et al., Ferroptosis is induced following siramesine and lapatinib treatment in breast cancer cells, Cell Death and Disease, 7(7):e2307, 11 pages, (2016).
Makhey et al., Sbustitute Benzo[i]phenanthridines as Mammalian Topoisomerase-Targeting Agents, Bioorg. Med. Chem. 11(8):1809-1820 (2003).
Mayer, R. J. et al., Randomized Trial of TAS-102 for Refractory Metastatic Colorectal Cancer, NEJM, 372(20):1909-1919 (2015).
Mckeage et al., Phase I and Pharmacokinetic Study of an Oral Platinum Complex Given Daily for 5 Days in Patients With Cancer, Journal of Clinical Oncology, 15(7):2691-2700 (1997).

(56) References Cited

OTHER PUBLICATIONS

Montet, X. et al., Multivalent Effects of RGD Peptides Obtained by Nanoparticle Display, J. Med. Chem. 49:6087-6093 (2006).

Nunes, Jessica J. et al., Targeting NF-kappa B Signaling by Artesunate Restores Sensitivity of Castrate-Resistant Prostate Cancer Cells to Antiandrogens, NEOPLASIA, 19(4):333-345, (2017).

Núñez, N. P. et al., PPAR-γ Ligands and Amino Acid Deprivation Promote Apoptosis of Melanoma, Prostate, and Breast Cancer Cells, Cancer Letters, 236:133-141, (2006).

Ohnishi, S. et al., Organic Alternatives to Quantum Dots for Intraoperative Near-Infrared Fluorescent Sentinel Lymph Node Mapping, Molecular Imaging 4(3):172-181 (2005).

Omidfar, K., and Shirvani, Z. Single Domain Antibodies: A New Concept for Epidermal Growth Factor Receptor and EGFRvIII Targeting, DNA and Cell Biology, 31(6):1015-1026, (2012).

Ow, H. et al., Bright and Stable Core-Shell Fluorescent Silica Nanoparticles, Nano Letters, 5(1):113-117 (2005).

Papamicheal, D., The Use of Thymidylate Synthase Inhibitors in the Treatment of Advanced Colorectal Cancer: Current Status, The Oncologist, 4:478-487 (1999).

Patel, K. N. et al., MUC1 plays a role in tumor maintenance in aggressive thryroid carcinomas, Surgery 138(6):994-1002 (2005).

Phillips, E. et al., Clinical translation of an ultrasmall inorganic optical-PET imaging nanoparticle probe, Science Translational Medicine, 6(260):260ra149-260ra149 (2014).

Piatyszek, M.A. et al., Iodo-Gen-Mediated Radioiodination of Nucleic Acids, J. Anal. Biochem. 172(2):356-359 (1988).

Pommier, Y., Topoisomerase I inhibitors: camptothecins and beyond, Nat. Rev. Cancer, 6(10):789-802 (2006).

Prosecution File History of Chinese Application 201080039307.2 as of Oct. 5, 2016, 54 pages.

Prosecution File History of European Application No. 10 794 842.4 as of Jul. 29, 2016, 30 pages.

Ren, G. et al., PET of Malignant Melanoma Using [18]F-Labeled Metallopeptides, The Journal of Nuclear Medicine, 50(11):1865-1872 (2009).

Reubi, J.C. et al., Distribution of Somatostatin Receptors in Normal and Tumor Tissue, Metabolism, 39(9)(2):78-81 (1990).

Reubi, J.C. et al., Somatostatin Receptors and Their Subtypes in Human Tumors and in Peritumoral Vessels, Metabolism, 45(8)(1):39-41 (1996).

Rianasari, I. et al., Covalent Coupling of Nanoparticles with Low-Density Functional Ligands to Surface via Click Chemistry, Int. J. Mol. Sci. 14:3705-3717 (2013).

Ruoslahti, E. and Pierschbacher, M. D., New Perspectives in Cell Adhesion: RGD and Integrins, Science 238:491 (1987).

Sadasivan, et al., Alcoholic Solvent Effect on Silica Synthesis—NMR and DLS Investigation, J. Sol-Gel Science and Technology, 12:5-14 (1998).

Sanderson, R. J. et al., In vivo Drug-Linker Stability of an Anti-CD30 Dipeptide-Linked Auristatin Immunoconjugate, Clinical cancer Research, 11:843-852 (2005).

Sato, M. et al., The ferroptosis inducer erastin irreversibly inhibits systems $\chi_c$-and synergizes with cisplatin to increase cisplatin's cytotoxicity in cancer cells, Scientific Reports, 8(1):968, 9 pages, (2018).

Schladt, T. D. et al., Multifunctional superparamagnetic MnO@SiO2 core/shell nanoparticles and their application for optical and magnetic resonance imaging, Journal of Materials Chemistry, 22:9253-9262, (2012).

Seftor, R. E. B. et al., Role of the alpha v beta 3 integrin in human melanoma cell invasion, Proc. Natl. Acad. Sci., 89:1557-1561 (1992).

Sehm, T. et al., Temozolomide toxicity operated in a xCT/SLC7a11 dependent manner and is fostereed by ferroptosis, Oncotarget, 7(46):74630-74647, (2016).

Seung, S. K. et al., Phase 1 Study of Stereotactic Body Radiotherapy and Interleukin-2: Tumor and Immunological Responses, Science Trnslational Medicine 14(137):137ra74 1-7 (2012).

Seymour, L.W., Passive Tumor Targeting of Soluble Macromolecules and Drug Conjugates, Critical Reviews in Therapeutic Drug Carrier Systems, 9(2):135-187 (1992).

Sharma, P. et al., Nanoparticles of bioimaging, Advances in Colloid and Interface Science, 123-126:471-485 (2006).

Slowing, I. I. et al., Mesoporous silica nanoparticles as controlled release drug delivery and gene transfection carriers, Advanced Drug Delivery Reviews, 60:1278-1288 (2008).

Soster, M. et al., Targeted dual-color silica nanoparticles provide univocal identification of micrometastases in preclinical models of colorectal cancer, International Journal of Nanomedicine, 7:4797-4807 (2012).

Stabin, M. G. et al., OLINDA/EXM: The Second-Generation Personal Computer Software for Internal Dose Assessment in Nuclear Medicine, J Nucl Med. 46:1023-1027 (2005).

Suteewong, T. et al., Highly Animated Mesoporous Silica Nanoparticles with Cubic Pore Structure, Journal of American Chemical Society, 133(2):172-175, (2011).

Takeshima, T. et al., Local Radiation Therapy Inhibits Tumor Growth through the Generation of Tumor-Specific CTL: Its Potentiation by Combination with Th1 Cell Therapy, Cancer Research, 70(7):2697-2706 (2010).

Takezawa, K. et al., Sorafenib Inhibits Non-Small Cell Lung Cancer Cell Growth by Targeting B-RAF in KRAS Wild-Type Cells and C-RAF in KRAS Mutant Cells, Cancer Res, 69(16):6515- 6521 (2009).

Tanaka, E. et al., Image-Guided Oncologic Surgery Using Invisible Light: Completed Pre-Clinical Development for Sentinel Lymph Node Mapping, Annals of Surgical Oncology 13(12):1671-1681 (2006).

Tavernaro, I. et al., Bright Fluorescent silica-nanoparticle probes for high-resolution STED and confocal microscopy, Beilstein Journal of Nanotechnology, 8:1283-1296, (2017).

Thakor, A. S. and Gambhir, S. S., Nanooncology: The Future of Cancer Diagnosis and Therapy, CA Cancer J. Clin., 63(6):395-418 (2013).

Topalian, S. L et al., Safety, Activity, and Immune Correlates of Anti-PD-1 Antibody in Cancer, The New England Journal of Medicine, 366(26):2443-2454 (2012).

Urakami, S. et al., Long-term control or possible cure? Treatment of stage D2 prostate cancer under chemotherapy using cisplatin and estramustine phosphate followed by maximal androgen blockade, Int. Urol. Nephol., 40:365-368, (2008).

Van Schooneveld, M. M. et al., Improved Biocompatibility and Pharmacokinetics of Silica Nanoparticles by Means of a Lipid Coating: A Multimodality Investigation, Nano Letters, 8(8):2517-2525 (2008).

Vejayakumaran, P. et al., Structural and thermal characterizations of silica nanoparticles grafted with pendant maleimide and epoxide grops, Journal of Colloid and Interface Science, 328:81-91 (2008).

Von Angerer, E. et al., The effect of a combination of zindoxifene and cisplatin on Dunning R3327-G prostatic carcinomas of the rat, Cancer Research Clinical Oncology, 118:339-343, (1992).

Wang, X. et al., Folate Receptor-Targeted Aggregation-Enhanced Near-IR Emitting Silica Nanoprobe for One-Photon in Vivo and Two-Photon ex Vivo Fluorescence Bioimaging, Bioconjugate Chemistry, 22:1438-1450 (2011).

Wang, Y. et al., Tumor cell targeted delivery by specific peptide-modified mesoporous silica nanoparticles, J. Mater. Chem., 22:14608-14616, (2012).

Webb, et al., Sphingomyelin-cholesterol liposomes significantly enhance the pharmacokinetic and therapeutic properties of vincristine in murine and human tumour models, British J. of Cancer 72:896-904 (1995).

Webster, A. et al., Optical calcium sensors: development of a generic method for their introduction to the cell using conjugated cell penetrating peptides, Analyst, 130:163-70 (2005).

Wersäll, P.J. et al., Regression of non-irradiated metastases after extracranial stereotactic radiotherapy in metastatic renal cell carcinoma, Acta Oncologica, 45:493-497 (2006).

Wilks, M. Q. et al., Imaging PEG-Like Nanoprobes in Tumor, Transient Ischemia, and Inflamatory Disease Models, Bioconjugate Chemistry, 26(6):1061-1069, (2015).

(56) References Cited

OTHER PUBLICATIONS

Written Opinion, PCT/US2016/034351 (Methods of Treatment Using Ultrasmall Nanoparticles To Induce Cell Death of Nutrient-Deprived Cancer Cells Via Ferroptosis, filed May 26, 2016), issued by ISA/EPO, 9 pages, dated Aug. 23, 2016.

Wu, P. et al., Imaging Breast Cancer Cells and Tissues Using Peptide-Labeled Fluorescent Silica Nanoparticles, Journal of Nanoscience and Nanotechnology, 8(5):2483-2487 (2008).

Xia, T. et al., Polyethyleneimine Coating Enhances the Cellular Uptake of Mesoporous Silica Nanoparticles and Allows Safe Delivery of siRNA and DNA Constructs, ACS Nano, 3(10):3273-3286, (2009).

Xie, Y. et al., Ferroptosis: process and function, Cell Death and Differentiation, 23(3):369-379, (2016).

Xu, Z. et al., DNA Minor Groove Biding-Directed Poisoning of Human DNA Topoisomerase I by Terbenzimidazoles, Biochemistry 37(10):3558-3566 (1998).

Yamaguchi, Y. et al., Piperlongumine rapidly induces the death of human pancreatic cancer cells mainly through the induction of ferroptosis, International Journal of Oncology, 52:1011-1022, (2018).

Yu, Y. et al., The ferroptosis inducer erastin enhances sensitivity of acute myeloid leukemia cells to chemotherapeutic agents, Molecular & Cellular Oncology, 2(4):e1054549-1-e1054549-7, (2015).

Zeng, J. et al., Anti-PD-1 Blockade and Stereotactic Radiation Produce Long-Term Survival in Mice With Intracranial Gliomas, Intl. J. Radiation Oncol. Biol. Phys., 86(2):343-349 (2013).

Zhang, et al., Copper-62 labeled ReCCMSH peptide analogs for melanoma PET imaging, Curr Radiopharm, 5(4):329-335 (2012) (ABSTRACT only attached).

Zhang, X. L. et al., Ultrasmall 1-6, radioiodinated alpha MSH-C dots for melanoma imaging and therapy, Journal of Labelled Compounds and Radiopharmaceuticals, 58(1):S114 (2015).

Zhen, C. et al., Radioiodination of Rhenium Cyclized a-Melanocyte-Stimulating Hormone Resulting in Enhanced Radioactivity Localization and Retention in Melanoma, Cancer Research, 64:1411-1418, (2004).

Zhong, Y. J. et al., Cathepsin B-cleavable doxorubicin prodrugs for targeted cancer therapy (Review), International Journal of Oncology, 42:373-383, (2013).

Mulder, W.J.M. et al., Quantum Dots with a Paramagnetic Coating as a Bimodal Molecular Imaging Probe, Nano Letters, 6(1):1-6, (2006).

Choi, C.H.J. et al., Targeting kidney mesangium by nanoparticles of defined size, PNAS, 108(16):6656-6661, (2011).

Lin, Y.S. et al., Well-Ordered Mesoporous Silica Nanoparticles as Cell Markers, Chem. Mater. 17:4570-4573, (2005).

Peuschel, H. et al., Quantification of Internalized Silica Nanoparticles via STED Microscopy, Biomed. Res. Int., 2015; 961208 (2015).

Quest Medical Imaging, Instructions for use, Artemis Handheld System, Version 2.5, 24 pages (2013).

Wang, Y. et al., Fluorescent detection of ATP based on signaling DNA aptamer attached silica nanoparticles, Nanotechnology, 19(41):415605 (2008).

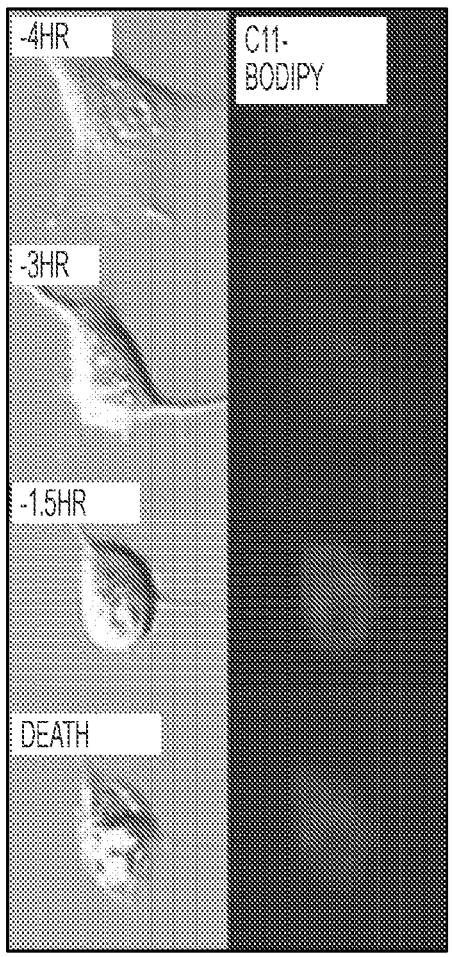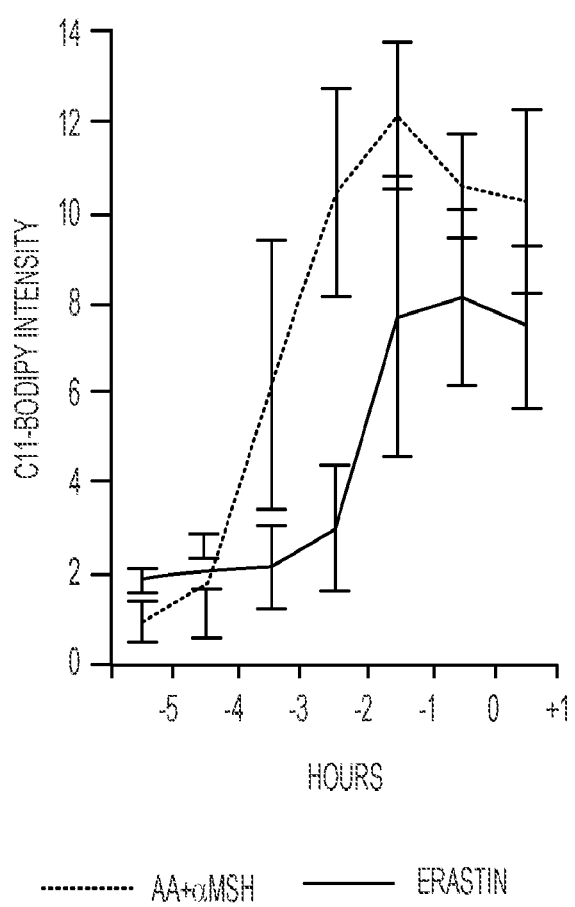
FIG. 3F                                   FIG. 3G

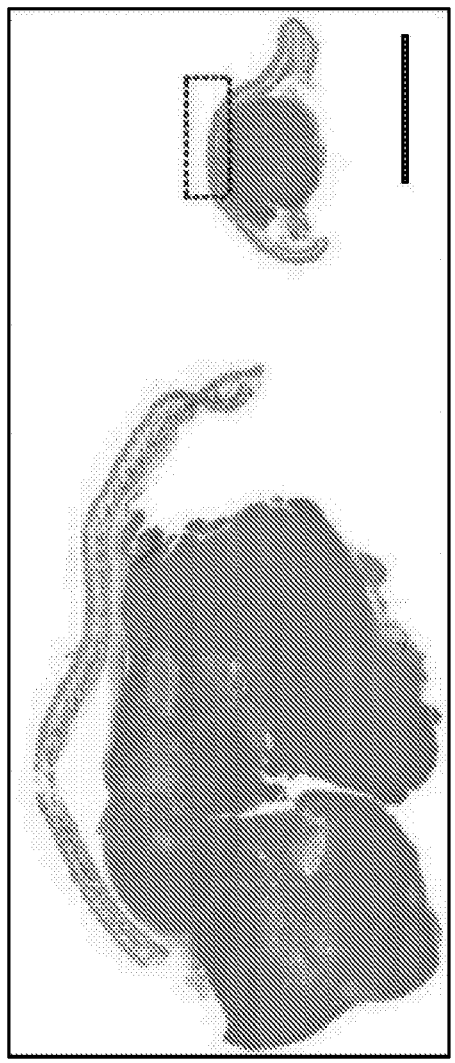
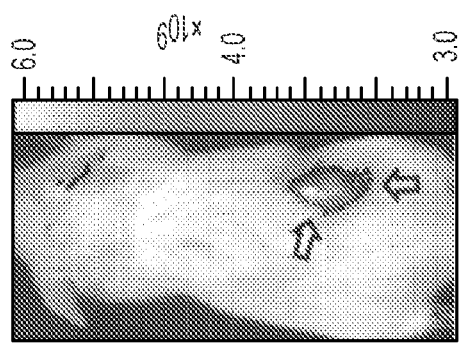
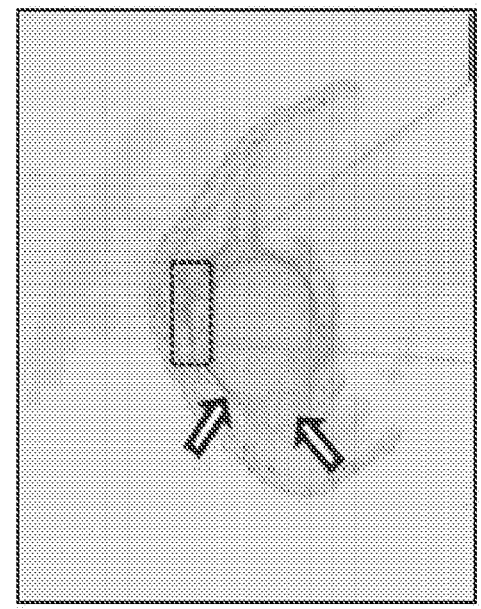
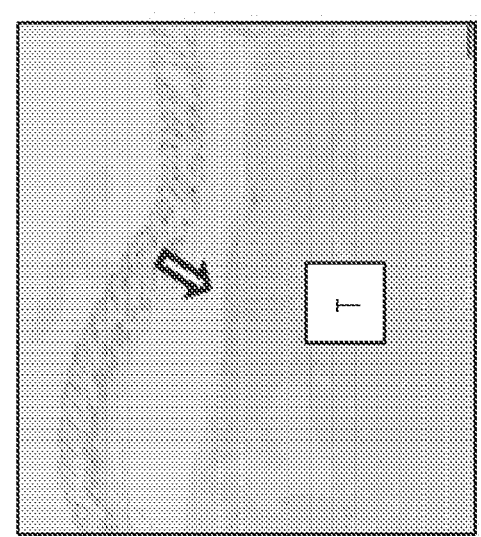
FIG. 5D
FIG. 5F
FIG. 5C
FIG. 5E

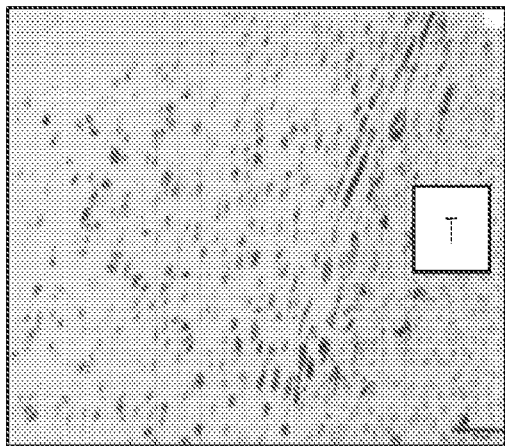
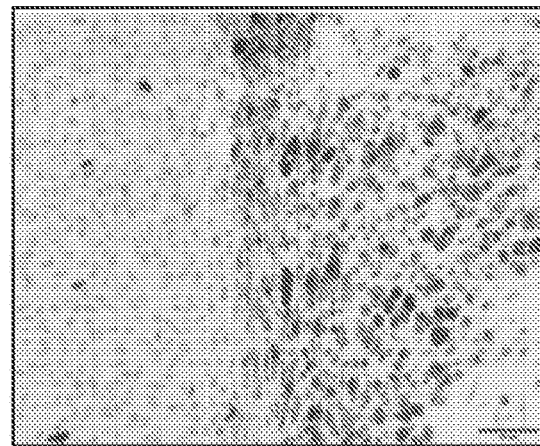
FIG. 5G    FIG. 5H
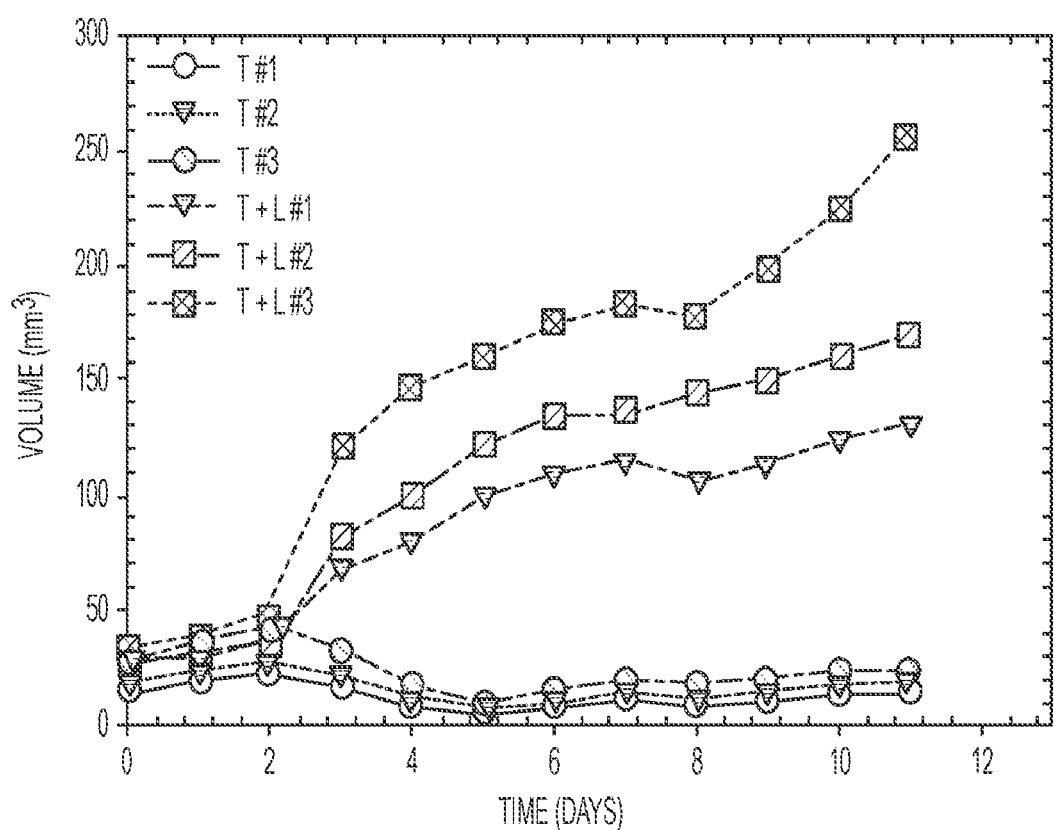
FIG. 5I

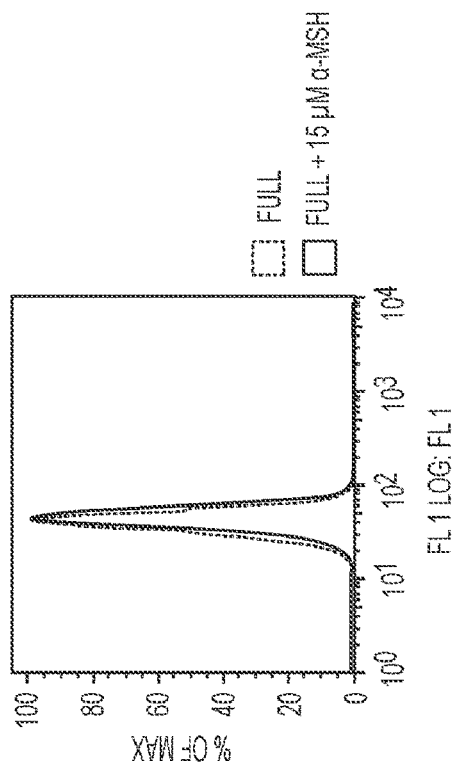
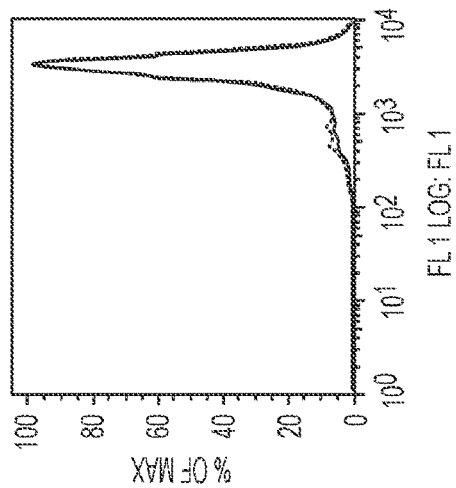
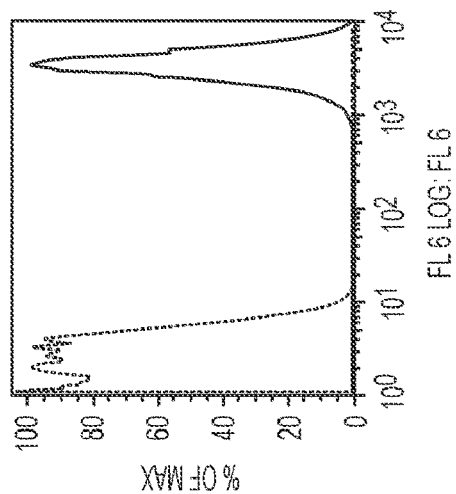
FIG. 7A
FIG. 7B
FIG. 7C

METHODS OF TREATMENT USING ULTRASMALL NANOPARTICLES TO INDUCE CELL DEATH OF NUTRIENT-DEPRIVED CANCER CELLS VIA FERROPTOSIS

CROSS REFERENCE TO RELATED APPLICATIONS

This application is a continuation of U.S. application Ser. No. 16/902,577 filed on Jun. 16, 2020, which is a continuation of U.S. application Ser. No. 15/573,855 filed on Nov. 14, 2017, which is a U.S. National Stage Entry of International Application No. PCT/US16/34351 filed May 26, 2016, which claims the benefit of U.S. Application Ser. No. 62/168,636 filed on May 29, 2015 and U.S. Application Ser. No. 62/280,960 filed on Jan. 20, 2016, the disclosures of each of which are hereby incorporated by reference in their entireties.

GOVERNMENT SUPPORT

This invention was made with government support under grant numbers CA199081, GM111350, and CA161280 awarded by the National Institutes of Health. The government has certain rights in the invention.

FIELD OF THE INVENTION

This invention relates generally to the use of nanoparticles, e.g., ultrasmall nanoparticles, to modulate molecular-level interactions (e.g., cellular/subcellular functions, e.g., cell death). In particular embodiments, the invention relates to methods of treatment with ultrasmall nanoparticles (e.g., C or C' dots) to selectively induce cell death in nutrient-deprived cancer cells via ferroptosis.

BACKGROUND

The design and development of highly integrated, cancer-targeted nanomedicines promise to enhance disease-specific targeting and improve access to intracellular pharmacological targets. However, a detailed understanding of molecular-level interactions (e.g., modulation of cellular/subcellular functions) driving the fate of nanomedicines in biological systems remains elusive. For example, the complex interplay between endocytosis and intracellular trafficking, physiologic, and/or metabolic pathways and how the targeted nanoparticles navigate these complex systems can be important to homeostatic regulation. Moreover, this interplay can vary due to the properties of the particle probe, surrounding biological conditions, and nature of the disease itself. Furthermore, particle uptake and accumulation within specific intracellular compartments may alter functional, metabolic, and/or energy homeostasis. For example, a number of particle-based probes undergoing endocytosis and intracellular trafficking have been shown to induce autophagy and to inhibit lysosome function. However, how these effects modulate cell survival over time remains unclear.

Ultrasmall (e.g., having a diameter no greater than 20 nm, e.g., no greater than 15 nm, e.g., no greater than 10 nm) FDA-approved fluorescent organo-silica particles (C dots) that were previously surface-adapted with PET radiolabels and the integrin-targeting peptide cyclo-(Arg-Gly-Asp-Tyr) (cRGDY) were found to be a working molecular cancer imaging agent in humans. For example, C dots were shown to preferentially accumulate within $\alpha v \beta 3$ integrin-expressing primary and/or metastatic lesions in small and larger animal and human subject melanoma models in addition to demonstrating bulk renal clearance. Detail on C dots are described in U.S. Pat. No. 8,298,677 B2 "Fluorescent silica-based nanoparticles", U.S. Publication No. 2013/0039848 A1 "Fluorescent silica-based nanoparticles", and U.S. Publication No. US 2014/0248210 A1 "Multimodal silica-based nanoparticles", the contents of which are incorporated herein by reference in their entireties. Moreover, ultrasmall poly(ethylene glycol)-coated (PEGylated) near-infrared (NIR) fluorescent silica nanoparticle, referred to as C' dots, with diameters controllable down to the sub-10 nm range that were additionally surface-modified with a 14-mer peptide analog, alpha-melanocyte stimulating hormone ($\alpha$-MSH) were found to target melanocortin-1 receptors (MC1-R) expressed on malignant melanoma cells. However, it remains unknown as to how these particles may modulate cellular function and intracellular trafficking.

Thus, there remains a need to determine how variations in concentration and time-based processes influence the post-internalization fate of particle-based probes to improve the design of application-specific nanomedicine (e.g., C and C' dot) platforms.

SUMMARY

Described herein is a method of induced cell death via ferroptosis by nanoparticle ingestion. Moreover, the present disclosure describes the administration of high concentrations of ultrasmall (e.g., having a diameter no greater than 20 nm, e.g., no greater than 15 nm, e.g., no greater than 10 nm) nanoparticles at multiple times over the course of treatment in combination with a nutrient-depleted environment, thereby modulating cellular metabolic pathways to induce cell death by the mechanism ferroptosis. Ferroptosis involves iron, reactive oxygen species, and a synchronous mode of cell death execution.

It was found that treatment of cells with $\alpha$-MSH-PEG-C' dots in a particular nutrient-deprived environment can induce ferroptosis in cancer cells (or PEG-C' dots without $\alpha$-MSH, e.g., requiring a longer period of time compared to $\alpha$-MSH-PEG-C' dots), even without the presence of a drug. Taken together, the results described herein indicated that cells cultured in the absence of amino acids and treated with $\alpha$-MSH-PEG-C' dots undergo cell death by ferroptosis. Ferroptosis in this context was observed to propagate from cell to cell in a wave-like manner. Without having to be bound by theory, this suggested cell to cell communication of a death-inducing signal.

In one aspect, the invention is directed to a method of treatment of a subject, the method comprising: administering nanoparticles for accumulation at sufficiently high concentration in tumor tissue to induce ferroptosis (e.g., ferroptotic cell death involving iron-dependent necrosis or reactive oxygen species-dependent necrosis).

In certain embodiments, the nanoparticles comprise ultrasmall nanoparticles (e.g., C dot, e.g., C' dot).

In certain embodiments, the high concentration is greater than 1 µM, e.g., greater than 15 µM, e.g., greater than 60 µM. In certain embodiments, the high concentration is a local concentration within a range from 0.18 µM to 1.8 µM in the tumor tissue (e.g., wherein the high concentration is a local concentration in the tumor tissue of at least 0.18 µM, at least 0.3 µM, at least 0.4 µM, at least 0.5 µM, or at least 0.6 µM; e.g., wherein the nanoparticles are silica-based, e.g., wherein the nanoparticles are C dots or C' dots).

In certain embodiments, the tumor tissue is sufficiently amino acid (or metabolically) deprived.

In certain embodiments, the tumor tissue is sensitized to the induction of ferroptosis.

In another aspect, the invention is directed to a method of combinational treatment of a subject, the method comprising: administering a drug for transport to (and/or accumulation in) a tumor tissue; and administering nanoparticles for accumulation at sufficiently high concentration in the tumor tissue (to induce ferroptosis).

In certain embodiments, the drug comprises a chemotherapeutic agent (e.g., TAS-102).

In certain embodiments, the nanoparticles comprise ultrasmall nanoparticles (e.g., C dot, e.g., C' dot).

In certain embodiments, the high concentration is greater than 1 µM, e.g., greater than 15 µM, e.g., greater than 60 µM. In certain embodiments, the high concentration is a local concentration within a range from 0.18 µM to 1.8 µM in the tumor tissue (e.g., wherein the high concentration is a local concentration in the tumor tissue of at least 0.18 µM, at least 0.3 µM, at least 0.4 µM, at least 0.5 µM, or at least 0.6 µM; e.g., wherein the nanoparticles are silica-based, e.g., wherein the nanoparticles are C dots or C' dots).

In certain embodiments, the tumor tissue is sufficiently amino acid (or metabolically) deprived. In certain embodiments, the tumor tissue is sensitized to the induction of ferroptosis.

In certain embodiments, administering the drug and administering the nanoparticles are accomplished by administering a composition comprising both the drug and the nanoparticles.

In certain embodiments, the composition comprises nanoparticle drug conjugates.

In another aspect, the invention is directed to a method of combinational treatment of a subject, the method comprising: depriving a tumor tissue (e.g., prostate cancer tissue) of hormones; and administering nanoparticles for accumulation at sufficiently high in the tumor tissue to induce ferroptosis.

In certain embodiments, the tumor tissue is deprived of hormones via castration (e.g., chemical castration).

In certain embodiments, the nanoparticles comprise ultrasmall nanoparticles (e.g., C dot, e.g., C' dot).

In certain embodiments, the high concentration is greater than 1 µM, e.g., greater than 15 µM, e.g., greater than 60 µM. In certain embodiments, the high concentration is a local concentration within a range from 0.18 µM to 1.8 µM in the tumor tissue (e.g., wherein the high concentration is a local concentration in the tumor tissue of at least 0.18 µM, at least 0.3 µM, at least 0.4 µM, at least 0.5 µM, or at least 0.6 µM; e.g., wherein the nanoparticles are silica-based, e.g., wherein the nanoparticles are C dots or C' dots).

In certain embodiments, the tumor tissue is sufficiently amino acid (or metabolically) deprived.

In certain embodiments, the tumor tissue is sensitized to the induction of ferroptosis.

In certain embodiments, the tumor tissue is selected from the group consisting of renal, prostate, melanoma, pancreatic, lung, fibrosarcoma, breast, brain, ovarian, and colon tumor tissue. In certain embodiments, the tumor pancreatic tissue comprises BxPC3 cells. In certain embodiments, the tumor lung tissue comprises H1650 cells.

In certain embodiments, the nanoparticles have an average diameter no greater than 15 nm. In certain embodiments, the nanoparticles have an average diameter no greater than 10 nm. In certain embodiments, the nanoparticles have an average diameter from about 5 nm to about 7 nm (e.g., about 6 nm).

In certain embodiments, the nanoparticles comprise from 1 to 20 targeting moieties, wherein the targeting moieties bind to receptors on tumor cells (e.g., wherein the nanoparticles have an average diameter no greater than 15 nm, e.g., no greater than 10 nm, e.g., from about 5 nm to about 7 nm, e.g., about 6 nm). In certain embodiments, the 1 to 20 targeting moieties comprises alpha-melanocyte-stimulating hormone (αMSH). In certain embodiments, the nanoparticles comprise a targeting moiety (e.g., αMSH).

In certain embodiments, the nanoparticles are administered multiple times over the course of treatment.

In certain embodiments, the method further comprises administering the nanoparticles every 3 or 4 days over the course of treatment.

In certain embodiments, the administered nanoparticles have a drug (e.g., a chemotherapeutic agent) attached. In certain embodiments, the drug is attached via a linker moiety (e.g., attached covalently or non-covalently).

In certain embodiments, drug delivery combines with native immunomodulation properties of the administered nanoparticles (e.g., wherein the nanoparticles comprise α-MSH-PEG-C' dots, e.g., wherein α-MSH is bound to a surface of the nanoparticles) (e.g., wherein the nanoparticles comprise an organic-polymer coating (e.g., polyethylene glycol (PEG))) to increase the therapeutic potential of C dots in cancer treatment and/or tissue repair processes (e.g., wound healing).

In another aspect, the invention is directed to a composition comprising nanoparticles (e.g., ultrasmall nanoparticles, e.g., C dot, e.g., C' dot) for use in a method of treating a subject, wherein the treating comprises delivering the composition to a tumor tissue of the subject for accumulation at sufficiently high concentration (e.g., greater than 1 µM, e.g., greater than 15 µM, e.g., greater than 60 µM) in tumor tissue (e.g., wherein the high concentration is a local concentration within a range from 0.18 µM to 1.8 µM in the tumor tissue) (e.g., wherein the high concentration is a local concentration in the tumor tissue of at least 0.18 µM, at least 0.3 µM, at least 0.4 µM, at least 0.5 µM, or at least 0.6 µM; e.g., wherein the nanoparticles are silica-based, e.g., wherein the nanoparticles are C dots or C' dots) (e.g., that is sufficiently amino acid (or metabolically) deprived or otherwise sensitive to the induction of ferroptosis) to induce ferroptosis.

In another aspect, the invention is directed to a composition comprising nanoparticles (e.g., ultrasmall nanoparticles, e.g., C dot, e.g., C' dot) for accumulation at sufficiently high concentration (e.g., greater than 1 µM, e.g., greater than 15 µM, e.g., greater than 60 µM) in tumor tissue (e.g., wherein the high concentration is a local concentration within a range from 0.18 µM to 1.8 µM in the tumor tissue) (e.g., wherein the high concentration is a local concentration in the tumor tissue of at least 0.18 µM, at least 0.3 µM, at least 0.4 µM, at least 0.5 µM, or at least 0.6 µM; e.g., wherein the nanoparticles are silica-based, e.g., wherein the nanoparticles are C dots or C' dots) (e.g., that is sufficiently amino acid (or metabolically) deprived or otherwise sensitive to the induction of ferroptosis) to induce ferroptosis for use in therapy.

In another aspect, the invention is directed to a first composition comprising a drug (e.g., a chemotherapeutic agent, e.g., TAS 102) and a second composition comprising nanoparticles (e.g., ultrasmall nanoparticles, e.g., C dot, e.g., C' dot) for use in a method of treating a subject, wherein the treating comprises delivering the first composition for transport to (and/or accumulation in) a tumor tissue of the subject; and delivering the second composition to the tumor tissue of the subject for accumulation at sufficiently high concentration (e.g., greater than 1 µM, e.g., greater than 15 µM, e.g., greater than 60 µM) in tumor tissue (e.g., wherein the high concentration is a local concentration within a range from 0.18 µM to 1.8 µM in the tumor tissue) (e.g., wherein the high concentration is a local concentration in the tumor tissue of at least 0.18 µM, at least 0.3 µM, at least 0.4 µM, at least 0.5 µM, or at least 0.6 µM; e.g., wherein the nanoparticles are silica-based, e.g., wherein the nanoparticles are C dots or C' dots) (e.g., that is sufficiently amino acid (or metabolically) deprived or otherwise sensitive to the induction of ferroptosis) to induce ferroptosis.

In another aspect, the invention is directed to a first composition comprising a drug (e.g., any chemotherapeutic agent, e.g., TAS 102) for transport to (and/or accumulation in) a tumor tissue of a subject; and a second composition comprising nanoparticles (e.g., ultrasmall nanoparticles, e.g., C dot, e.g., C' dot) for accumulation at sufficiently high concentration (e.g., greater than 1 µM, e.g., greater than 15 µM, e.g., greater than 60 µM) in tumor tissue (e.g., wherein the high concentration is a local concentration within a range from 0.18 µM to 1.8 µM in the tumor tissue) (e.g., wherein the high concentration is a local concentration in the tumor tissue of at least 0.18 µM, at least 0.3 µM, at least 0.4 µM, at least 0.5 µM, or at least 0.6 µM; e.g., wherein the nanoparticles are silica-based, e.g., wherein the nanoparticles are C dots or C' dots) (e.g., that is sufficiently amino acid (or metabolically) deprived or otherwise sensitive to the induction of ferroptosis) to induce ferroptosis for use in therapy.

In another aspect, the invention is directed to a composition comprising nanoparticles (e.g., ultrasmall nanoparticles, e.g., C dot, e.g., C' dot) for use in a method of treating a subject, wherein the treating comprises depriving a tumor tissue (e.g., prostate tissue) of the subject of hormones (e.g., via castration (e.g., chemical castration)); and delivering the composition to the tumor tissue of the subject for accumulation at sufficiently high concentration (e.g., greater than 1 µM, e.g., greater than 15 µM, e.g., greater than 60 µM) in tumor tissue (e.g., wherein the high concentration is a local concentration within a range from 0.18 µM to 1.8 µM in the tumor tissue) (e.g., wherein the high concentration is a local concentration in the tumor tissue of at least 0.18 µM, at least 0.3 µM, at least 0.4 µM, at least 0.5 µM, or at least 0.6 µM; e.g., wherein the nanoparticles are silica-based, e.g., wherein the nanoparticles are C dots or C' dots) (e.g., that is sufficiently amino acid (or metabolically) deprived or otherwise sensitive to the induction of ferroptosis) to induce ferroptosis.

Elements of embodiments involving one aspect of the invention (e.g., methods) can be applied in embodiments involving other aspects of the invention (e.g., systems), and vice versa.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In certain embodiments, administration is oral. Additionally or alternatively, in certain embodiments, administration is parenteral. In certain embodiments, administration is intravenous.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In certain embodiments, biodegradable materials are enzymatically broken down. Alternatively or additionally, in certain embodiments, biodegradable materials are broken down by hydrolysis. In certain embodiments, biodegradable polymeric materials break down into their component polymers. In certain embodiments, breakdown of biodegradable materials (including, for example, biodegradable polymeric materials) includes hydrolysis of ester bonds. In certain embodiments, breakdown of materials (including, for example, biodegradable polymeric materials) includes cleavage of urethane linkages.

"Cancer": As used herein, the term "cancer" refers to a malignant neoplasm or tumor (Stedman's Medical Dictionary, 25th ed.; Hensly ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; connective tissue cancer;

epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B cell ALL, T cell ALL), acute myelocytic leukemia (AML) (e.g., B cell AML, T cell AML), chronic myelocytic leukemia (CML) (e.g., B cell CIVIL, T cell CML), and chronic lymphocytic leukemia (CLL) (e.g., B cell CLL, T cell CLL)); lymphoma such as Hodgkin lymphoma (HL) (e.g., B cell HL, T cell HL) and non Hodgkin lymphoma (NHL) (e.g., B cell NHL such as diffuse large cell lymphoma (DLCL) (e.g., diffuse large B cell lymphoma), follicular lymphoma, chronic lymphocytic leukemia/small lymphocytic lymphoma (CLL/SLL), mantle cell lymphoma (MCL), marginal zone B cell lymphomas (e.g., mucosa associated lymphoid tissue (MALT) lymphomas, nodal marginal zone B cell lymphoma, splenic marginal zone B cell lymphoma), primary mediastinal B cell lymphoma, Burkitt lymphoma, lymphoplasmacytic lymphoma (e.g., Waldenström's macroglobulinemia), hairy cell leukemia (HCL), immunoblastic large cell lymphoma, precursor B lymphoblastic lymphoma and primary central nervous system (CNS) lymphoma; and T cell NHL such as precursor T lymphoblastic lymphoma/leukemia, peripheral T cell lymphoma (PTCL) (e.g., cutaneous T cell lymphoma (CTCL) (e.g., mycosis fungoides, Sezary syndrome), angioimmunoblastic T cell lymphoma, extranodal natural killer T cell lymphoma, enteropathy type T cell lymphoma, subcutaneous panniculitis like T cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CIVIL), chronic neutrophilic leukemia (CNL), hypereosinophilic syndrome (HES); neuroblastoma; neurofibroma (e.g., neurofibromatosis (NF) type 1 or type 2, schwannomatosis); neuroendocrine cancer (e.g., gastroenteropancreatic neuroendocrine tumor (GEP NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

"Carrier": As used herein, "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Chemotherapeutic Agent": As used herein, the term "chemotherapeutic agent" (e.g., anti-cancer drug) has its art-understood meaning referring to one or more pro-apoptotic, cytostatic and/or cytotoxic agents, for example, specifically including agents utilized and/or recommended for use in treating one or more diseases, disorders or conditions associated with undesirable cell proliferation. In many embodiments, chemotherapeutic agents are useful in the treatment of cancer. In some embodiments, a chemotherapeutic agent may be or comprise one or more alkylating agents, one or more anthracyclines, one or more cytoskeletal disruptors (e.g., microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more vinca alkaloids, and/or one or more analogs of one or more of the following (i.e., that share a relevant anti-proliferative activity). In some particular embodiments, a chemotherapeutic agent may be or comprise one or more of Actinomycin, all-trans retinoic acid, an Auristatin, Azacitidine, Azathioprine, Bleomycin, Bortezomib, Carboplatin, Capecitabine, Cisplatin, Chlorambucil, Cyclophosphamide, curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g., DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-

SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine. In some embodiments, a chemotherapeutic agent may be or comprise one or more of farnesyl-thiosalicylic acid (FTS), 4-(4-Chloro-2-methylphenoxy)-N-hydroxybutanamide (CMH), estradiol (E2), tetramethoxystilbene (TMS), δ-tocatrienol, salinomycin, or curcumin.

"Combination Therapy": As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

"Peptide" or "Polypeptide": The term "peptide" or "polypeptide" refers to a string of at least two (e.g., at least three) amino acids linked together by peptide bonds. In certain embodiments, a polypeptide comprises naturally-occurring amino acids; alternatively or additionally, in certain embodiments, a polypeptide comprises one or more non-natural amino acids (i.e., compounds that do not occur in nature but that can be incorporated into a polypeptide chain; see, for example, http://www.cco.caltech.edu/~dadgrp/Unnatstruct-.gif, which displays structures of non-natural amino acids that have been successfully incorporated into functional ion channels) and/or amino acid analogs as are known in the art may alternatively be employed). In certain embodiments, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc.

"Radiolabel": As used herein, "radiolabel" refers to a moiety comprising a radioactive isotope of at least one element. Exemplary suitable radiolabels include but are not limited to those described herein. In certain embodiments, a radiolabel is one used in positron emission tomography (PET). In certain embodiments, a radiolabel is one used in single-photon emission computed tomography (SPECT). In certain embodiments, radioisotopes comprise $^{99m}$Tc, $^{111}$In, $^{64}$Cu, $^{186}$Re, $^{188}$Re, $^{153}$Sm, $^{177}$Lu, $^{67}$Cu, $^{123}$I, $^{124}$I, $^{125}$I, $^{11}$C, $^{13}$N, $^{15}$O, $^{18}$F, $^{186}$Re, $^{188}$Re, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, $^{89}$Zr, $^{225}$Ac, and $^{192}$Ir.

"Subject": As used herein, the term "subject" includes humans and mammals (e.g., mice, rats, pigs, cats, dogs, and horses). In many embodiments, subjects are mammals, particularly primates, especially humans. In certain embodiments, subjects are livestock such as cattle, sheep, goats, cows, swine, and the like; poultry such as chickens, ducks, geese, turkeys, and the like; and domesticated animals particularly pets such as dogs and cats. In certain embodiments (e.g., particularly in research contexts) subject mammals will be, for example, rodents (e.g., mice, rats, hamsters), rabbits, primates, or swine such as inbred pigs and the like.

"Substantially": As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Therapeutic agent": As used herein, the phrase "therapeutic agent" refers to any agent that has a therapeutic effect and/or elicits a desired biological and/or pharmacological effect, when administered to a subject.

"Treatment": As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In certain embodiments, treatment may be of a subject who has been diagnosed as suffering from the relevant disease, disorder, and/or condition. In certain embodiments, treatment may be of a subject known to have one or more susceptibility factors that are statistically correlated with increased risk of development of the relevant disease, disorder, and/or condition.

Drawings are presented herein for illustration purposes, not for limitation.

BRIEF DESCRIPTION OF DRAWINGS

The foregoing and other objects, aspects, features, and advantages of the present disclosure will become more apparent and better understood by referring to the following description taken in conduction with the accompanying drawings, in which:

FIG. 1A shows that exemplary α-MSH-PEG-C' dots are ultrasmall, 6 nm diameter silica-based particles with a fluorescent (e.g., Cy5 encapsulated) core and polyethylene glycol (PEG) coating and alpha melanocyte-stimulating hormone (αMSH)-modified exterior.

FIG. 1B shows that α-MSH-PEG-C' dots localize to lysosomal networks in cells. M21 melanoma cells expressing LAMP1-GFP (were treated with α-MSH-PEG-C' dots (15 μM) for 24 hours. Note that colocalization between nanoparticles (Cy5 fluorescence, pseudo-colored and LAMP1-GFP are merged in image. Bar=10 μm.

FIGS. 1C-1E show that α-MSH-PEG-C' dots are well-tolerated in nutrient-replete media and that M21 cells treated with the indicated α-MSH-PEG-C' dots concentrations and cultured for 40 hours. Nanoparticles had no significant effect on cell survival (FIG. 1D) or cell proliferation (FIG. 1E). Bars indicate mean+/−standard error of the mean. N=3 biological experiments, with five independent fields of view for each. See FIGS. 10A and 10B for individual experimental values. Scale error bars indicate S.D. Bar=10 µM.

FIGS. 1F-1H show that autophagy and lysosome function in nanoparticle-treated cells are unperturbed. Blot shows LC3-I and -II in cells treated with increasing doses of α-MSH-PEG-C' dots for 24 hours compared to untreated and amino acid-starved (AA-st) cells, in the presence (+) and absence (−) of the lysosome inhibitor concanamycin A (ConA, 1 hour at 100 nM). Levels of LC3-II (FIG. 1G) are unaltered by nanoparticle treatment, and ConA-inducible LC3-II accumulation (FIG. 1H), a measure of autophagy turnover, is similar between treated and control cells. SEM bars indicate mean+/−standard error of the mean. N=3 for each group. See FIGS. 10C and 10D for individual experimental values.

FIGS. 1I-1J show that nanoparticle treatment induces cell death of M21 cells cultured in amino acid-free media. Images show live control cells and dead (Sytox green-positive nanoparticle-treated cells in AA-st conditions. Scale bar=10 µm.

FIG. 1I shows percent Sytox green-positive cells in full media (Full) or AA-st conditions after 50 hours, as determined by time lapse microscopy (FIG. 1J). Bars indicate mean+/−standard deviation. N=4 for each group. Each replicate is from one biological experiment, quantified with five independent fields of view.

FIG. 1K shows M21 cells treated with 15 µM α-MSH-PEG-C' dots in full media in culture for 72 hours prior to create xenografts in immunodeficient (SCID/Beige) mice demonstrate growth inhibition (inverted triangles) relative to untreated cells (circles). Schematic shows workflow, comprising (1) particle-loading M21 melanoma cells in culture and (2) injecting particle-loaded M21 cells into mice to assay xenograft tumor growth versus control cells. Data show mean tumor volume over 22 days of growth from three tumors per group. Bars indicate mean+/−standard error of the mean. Particle-treated M21 cells showed statistically significant (p<0.001) growth inhibition compared with controls over the study interval. P-value is from a Wald test in a regression model estimated by generalized estimating equations to take into account the longitudinal nature of the data.

FIG. 2A shows MCF10A human mammary epithelial cells cultured in the absence of amino acids with 15 µM α-MSH-PEG-C' dots undergo cell death after 30 hours with necrotic features. Insets show a dying cell indicated by an arrow. Fluorescence images show Sytox green-labeling of dead cell nuclei. Bar=10 µM.

FIGS. 2B-2F show quantification of cell death (Sytox green+) in MCF10A and mouse embryo fibroblast (MEF) cultures in full media or amino acid-starved (AA-st) conditions in the presence or absence of 15 µM α-MSH-PEG-C' dots, and after 40 hours (MCF10A) (FIG. 2B) or 45 hours (MEF) (FIG. 2C), as determined by time-lapse microscopy. Bars indicate mean+/−standard deviation. N=5 per group. Each replicate is from one biological experiment, quantified with five independent fields of view.

FIGS. 2D-2F show cell death assays (similar as the assays shown in FIGS. 2B-2C) indicate that inhibition of apoptosis by Bcl2 overexpression in MCF10A (FIG. 2D), quantified after a 38 hour time-lapse experiment, or deletion of Bax and Bak in MEF (FIG. 2E), quantified after 45 hours, or inhibition of necroptosis by deletion of ripk3 in in MEF (FIG. 2F) quantified after 45 hours, or inhibition of autophagy by knockout of Atg5 in MEF after 45 hours (FIG. 2F) does not inhibit cell death induced by amino acid starvation and treatment with 15 µM α-MSH-PEG-C' dots. Bars indicate mean+/−standard deviation. N=5 per group. Each replicate is from one biological experiment, quantified with five independent fields of view.

FIGS. 3A-3G show ferroptosis is the underlying mechanisms of α-MSH particle-induced cell death.

FIGS. 3A-3C show quantification of cell death (Sytox green+) in MCF10A cells cultured in full media (Full) or amino acid-starved (AA-st) conditions in the presence or absence of 15 µM α-MSH-PEG-C' dots and (FIG. 3A) 1 µM Ferrostatin-1 (Fer-1) after 40 hours, (FIG. 3B) 100 µM deferoxamine (DFO) after 38 hours, and (FIG. 3C) 50 µM butylated hydroxyanisole (BHA), 200 µM ascorbic acid (AA), 100 µM Trolox, 10 mM N-acetylcysteine (NAC), or 5 mM glutathione (GSH), after 40 hours. Bars indicate mean+/−standard deviation. N=5 per group. Each replicate is from one biological experiment, quantified with five independent fields of view.

FIGS. 3D and 3E show images from time-lapse analysis of MCF10A undergoing ferroptosis in amino acid-starved conditions with 15 µM α-MSH-PEG-C' dots. Note that death (Sytox green positivity) spreads cell-to-cell from the left side of the image to the right. Scale bar=10 µM.

FIGS. 3F-3G show lipid ROS accumulate prior to death in cells treated with 15 µM α-MSH-PEG-C' dots and amino acid withdrawal.

FIG. 3F shows treated cells cultured in the presence of C11-BODIPY that detects lipid ROS. Note that the fluorescence intensity of C11-BODIPY increases several hours before cell death (times indicated on each image prior to cell death in bottom image).

FIG. 3G shows quantification of C11-BODIPY fluorescence in particle-treated and amino acid-starved cells (dotted line), or erastin-treated cells (black line). Mean intensities out of five cells+/−standard deviation are shown from one biological experiment. Time zero indicates the time of cell death determined by DIC microscopy. Note that C11-BODIPY staining increases in intensity between three and four hours prior to cell death.

FIGS. 4A-4F show quantification of cell death (Sytox green+) in (FIGS. 4A-4B) BxPC3 pancreatic carcinoma cells after 40 hours, (FIGS. 4C-4D) H1650 lung carcinoma cells after 45 hours, and (FIGS. 4E-4F) HT1080 fibrosarcoma cells after 65 hours in full media (Full) or amino acid-free media (AA-st), in the presence or absence of 15 µM α-MSH-PEG-C' dots. Bars indicate mean+/−standard deviation. N=5 per group. Each replicate is from one biological experiment, quantified with five independent fields of view. Scale bars=10 µM.

FIG. 4G shows an exemplary model for α-MSH-PEG-C' dot nanoparticle-induced ferroptosis. Amino acid deprivation (I) and nanoparticle ingestion into lysosomes (II) both lead to depletion of glutathione (see FIGS. 7D-7E), contributing together to induce ferroptosis that is dependent on lysosomal iron, a known inducer of reactive oxygen species (ROS), and lipid peroxidation that is blocked by Ferrostatin-1 and liporoxstatin-1.

FIGS. 5A-5K show that α-MSH-PEG-C' dots inhibit tumor growth in HT1080 and 786-0 xenograft models.

FIGS. 5A, 5B, and 5K each show a graphical summary of 786-0 (FIG. 5K) and HT1080 (FIG. 5B) average tumor volume measurements in α-MSH-PEG-C' dot-treated (T; n=5) and saline-treated (C; n=3) mice; error bars indicate standard deviation. Three, high-dose α-MSH-PEG-C' dot (or control vehicle) treatments were i.v.-injected (a; arrows) over a 10-day period. Individual HT-1080 tumor volume measurements from part (FIG. 5A) are shown in FIG. 5B. Relative to control tumor volumes, data show marked inhibition of tumor growth and partial tumor regression after particle treatments (HT-1080: p<0.001; 786-OL P<0.01). P-values are from a Wald test in a regression model estimated by generalized estimating equations to take into account the longitudinal nature of the data.

FIG. 5C shows representative whole body Cy5 fluorescent imaging of a representative H1080 tumor xenograft.

FIG. 5D shows a low-power view of H&E-stained tissue sections from representative control and treated tumors reveal control specimens to be disproportionately larger in size than the corresponding treated ones.

FIGS. 5E-5H show immunohistochemical staining of tumor sections with Mac-2 shows scattered macrophages (arrow) surrounding control tumor sections (T) on (FIG. 5E) low and (FIG. 5G) high power views, while corresponding (FIG. 5F) low and (FIG. 5H) high power views of Mac-2 stained treated sections show large numbers of Mac-2 positive cells circumscribing the tumor at similar locations (boxes, d, f; arrows). Small numbers of intratumoral Mac-2 positive cells are also noted.

FIG. 5I shows graphical summary of individual HT1080 tumor volume measurements in mice undergoing combined inhibitor and particle treatment (T+L; n=3) versus particle treatment alone (T; n=3). Three high-dose α-MSH-PEG-C' dot treatments (with and without i.p.-injected inhibitor) over a 10-day period. Relative to particle treatment alone, marked progression of tumor growth is seen following combined inhibitor and particle treatment (p<0.001).

FIG. 5J shows representative particle-exposed tumors reveal specimens to be disproportionately larger in size when additionally treated with Liproxstatin-1 (right tumor). Scale bars: 1 mm (FIG. 5D, FIG. 5E, and FIG. 5F); 50 μm (FIG. 5G, FIG. 5H); 1 cm (FIG. 5J).

FIGS. 6C-6E show quantification of cell death (Sytox green+) in amino acid-starved 786-0 renal cancer cells in the presence or absence of 15 μM α-MSH-PEG-C' dots. Bars indicate mean+/−standard deviation. N=5 per group. Each replicate is from one biological experiment, quantified with five independent fields of view. Scale bar=10 μm. Necrotic cell deaths were determined by morphology and rapid Sytox green positivity (FIG. 6D), as compared to apoptotic deaths (FIG. 6E).

FIGS. 7A-7K show that nanoparticles affect iron uptake and glutathione levels.

FIGS. 7A-7C show MCF10A cells treated with 15 μM α-MSH-PEG-C' dots in full media for 24 hours were examined by flow cytometry for levels of cytosolic ROS using 25 μM HDCFDA (FIG. 7B) and lipid peroxidation using 2 μM C11-BODIPY (581/591) (FIG. 7C). FIG. 7A shows Cy5 fluorescence of particle-treated cells (blue population).

FIG. 7D shows quantification of reduced glutathione (GSH) levels in MCF10A cells cultured in full media (Full) or amino acid-free media (AA-st) for 24 hours, in the presence or absence of 15 μM α-MSH-PEG-C' dots or 400 μM buthionine sulphoximine (BSO), an inhibitor of γ-glutamylcysteine synthetase, the rate-limiting enzyme for glutathione. Note that nanoparticle treatment and amino acid deprivation reduce glutathione levels alone and in combination, similar to treatment with BSO. Bars indicate mean+/−standard error of the mean, out of three independent experiments. See FIG. 12D for individual experimental values.

FIG. 7E shows total glutathione levels are reduced in nanoparticle-treated cells and relative levels of total glutathione in amino acid-starved cells, nanoparticle-treated cells (αMSH), and cells treated with the inhibitor of glutathione production BSO, after 24 hours.

FIG. 7F shows quantification of cell death (Sytox green+) of MCF10A cells cultured in AA-st conditions in the presence of 15 μM α-MSH-PEG-C' dots (white bars) or PEG-C' dots lacking the αMSH peptide (shaded bars) at 40 hours and 68 hours. Bars indicate mean+/−standard deviation. N=5 per group. Each replicate is from one biological experiment, quantified with five independent fields of view.

FIG. 7G shows that α-MSH-PEG-C' dots bind iron and treated cells have increased iron levels. Data shows iron concentrations determined from αMSH nanoparticle stock samples and untreated cells (both are "Controls", below the limit of detection), α-MSH-PEG-C' dots purified from culture media (NP+ Media), and cells treated with nanoparticles (NP+ Cells). Iron concentration standards are shown as red data points. All measurements are means from one biological experiment performed in triplicate. Raw data are shown in Table 1.

FIG. 7H shows ferritin heavy chain expression is increased in amino acid-starved (AA-st) cells by treatment with 15 μM α-MSH-PEG-C' dots or by treatment with ferric ammonium citrate (FAC), and is decreased by treatment with DFO. Western blot shows ferritin heavy chain (FTH1) expression compared to actin loading control, 24 hours after treatment with the indicated reagents.

FIG. 7I shows treatment of cells with iron (FAC) is sufficient to mimic α-MSH-PEG-C' dot-induced death in amino acid-starvation (AA-st) conditions. Graph shows quantification of percent cell death (Sytox green+) for cells treated as indicated.

FIG. 7J shows that pre-treatment with erastin sensitizes to nanoparticle-induced ferroptosis. Graph shows percent HT-1080 cell death (Sytox green+ cells) 18 hours (white bars) or 24 hours (shaded bars) after the indicated treatments. Pre-treatment with erastin for 4 hours is indicated as '−' or '+'. Note that erastin-pre-treatment does not induce cell death on its own ('No treat'), but sensitizes to both continued erastin treatment ('Erastin'), and the combination of α-MSH-PEG-C' dots (15 μM) and amino acid starvation ('AA-st+αMSH'), as pre-treated cultures ('+') undergo more cell death at 18 and 24 hours. Bars indicate mean+/−standard deviation. N=5 per group. Each replicate is from one biological experiment, quantified with five independent fields of view.

FIG. 7K shows GPX4 activity is not inhibited by particle treatment. Data show specific activity of GPX4 from cell lysates collected after the indicated treatments. Data are from three independent biological experiments; bars represent mean+/−standard error of the mean.

FIG. 8A shows MCF10A cells cultured in amino acid-free media and treated with 100 nM concanamycin A (ConA) undergo cell death with morphologic features of apoptosis involving cell blebbing and fragmentation.

FIG. 8B shows quantification of cell death (Sytox green+) in MCF10A cells cultured in full media (Full) or amino acid-starved (AA-st) conditions, in the presence or absence of Bcl2 overexpression and treatment with ConA. Note Bcl2 inhibits apoptosis induced by ConA treatment in AA-st conditions. Bars indicate mean+/−standard deviation. N=5 per group. Each replicate is from one biological experiment, quantified with five independent fields of view.

FIG. 8C shows knockout of RIPK3 inhibits necroptosis. Graph shows percent cell death (Sytox green+) of wild-type (wt) and RIPK3−/−MEFs treated with a combination of 100 ng/ml TNFα, 1 µg/ml cycloheximide (CHX) and 20 µM zVAD to induce necroptosis. Note RIPK3−/−MEFs do not undergo cell death, similar to wt cells treated with 30 µM necrostatin-1 (Nec-1), a necroptosis inhibitor. Bars indicate mean+/−standard deviation. N=5 per group. Each replicate is from one biological experiment, quantified with five independent fields of view.

FIG. 8D shows MCF10A cells undergoing apoptosis in response to treatment with 50 µg/ml cycloheximide exhibit an asynchronous pattern of cell death. Left image shows image from time-lapse microscopy of cells that have undergone apoptosis (bright=Sytox green). Right image shows Sytox green-positive nuclei from left image, pseudocolored to represent the timing of individual cell deaths. The temporal pattern of cell death here is asynchronous compared to FIGS. 3D and 3E. All scale bars=10 µm.

FIG. 8E shows M21 cells cultured in full media in the absence (left) and presence (right) of 15 µM α-MSH-PEG-C' dots for 72 hours (particle fluorescence is shown in cyan).

FIG. 8F shows percent cell death (Sytox green+ cells) for control and particle-treated cells, at 3 days and 10 days after 72 hours of particle treatment in full media. Note that particle treatment in full media conditions does not inhibit cell viability. Bars indicate mean+/−standard deviation. N=5 per group. Each replicate is from one biological experiment, quantified with five independent fields of view.

FIG. 8G shows that liproxstatin-1 treatment inhibits particle-induced cell death. Quantification of cell death (Sytox green+) in MCF10A cells cultured in amino acid-starved (AA-st) conditions in the presence or absence of 15 µM α-MSH-PEG-C' dots and 1 µM Liproxstatin-1 after 40 hours. Bars indicate mean+/−standard deviation. N=5 per group. Each replicate is from one biological experiment, quantified with five independent fields of view.

FIG. 9A shows cell death measurements in HT-1080 cells treated with differently sized PEG-C' dots. Quantification of HT-1080 cell death (Sytox green+) cultured in full media or AA-st conditions for 48 hours in the absence or presence of 15 µM PEG-C' dots, 6 nm or 10 nm, lacking the αMSH peptide. Error bars represent S.D. Bars indicate mean+/− standard deviation. N=5 per group.

FIG. 9B shows that HT-1080 tumors are well vascularized. Images show a representative HT-1080 xenograft specimen, harvested 10 days after particle injection, and stained by immunohistochemistry for the endothelial marker CD31. Low magnification (4×) microscopic image of whole tumor (top image) and high magnification (40×) image of tumor region (bottom image). Note the presence of blood vessels throughout the tumor. Scale bars=500 µm (low power); 50 µm (high power).

FIG. 9C shows α-MSH-PEG-C' dot-treated 786-0 tumor shows large number of recruited macrophages. Low (top image) and high (bottom image) power views of Mac-2 stained treated sections show marked Mac-2 positive cells circumscribing the tumor at similar locations (box).

FIG. 10A shows data from the cell survival graph (on left) in FIG. 1C are shown. N=3 biological experiments, each data point represents the mean from five independent fields of view.

FIG. 10B shows data from the cell proliferation graph (on right) in FIG. 1C are shown. N=3 biological experiments, each data point represents the mean from five independent fields of view.

FIG. 10C shows individual LC3-II/actin values are shown from FIG. 1D, left graph. N=3 western blots for each group. Note that the 15 µm condition has two values plotted at 0.79.

FIG. 10D shows individual LC3-II turnover values are shown from FIG. 1D, right graph. N=3 western blots for each group.

FIG. 10E shows data from the cell death graph in FIG. 1E are shown. N=4 biological experiments, each data point represents the mean from five independent fields of view.

FIG. 10F shows data from the cell death graph on the left in FIG. 2B are shown for N=5 for each group. Each replicate is an independent field of view of the same biological experiment.

FIG. 10G shows data from the cell death graph on the right in FIG. 2B are shown for N=5 for each group. Each replicate is an independent field of view of the same biological experiment.

FIG. 10H shows data from the cell death graph in FIG. 2C are shown for N=5 for each group. Each replicate is an independent field of view of the same biological experiment.

FIG. 10I shows data from the cell death graph in FIG. 2D are shown for N=5 for each group. Each replicate is an independent field of view of the same biological experiment.

FIG. 10J shows data from the cell death graph in FIG. 2E are shown for N=5 for each group. Each replicate is an independent field of view of the same biological experiment.

FIG. 11A shows data from the cell death graph in FIG. 3A are shown. N=3 biological experiments, each data point represents the mean from five independent fields of view.

FIG. 11B shows data from the cell death graph in FIG. 3C are shown. N=5 for each group. Each replicate is an independent field of view of the same biological experiment.

FIG. 11C shows data from the cell death graph in FIG. 3B are shown. N=3 biological experiments, each data point represents the mean from five independent fields of view.

FIG. 11D shows data from the cell death graph in FIG. 4A are shown. N=5 for each group. Each replicate is an independent field of view of the same biological experiment.

FIG. 11E shows data from the cell death graph in FIG. 4B are shown. N=5 for each group. Each replicate is an independent field of view of the same biological experiment.

FIG. 11F shows data from the cell death graph in FIG. 4C are shown. N=3 biological experiments, each data point represents the mean from five independent fields of view.

FIG. 11G shows data from the cell death graph in FIG. 8B are shown. N=5 for each group. Each replicate is an independent field of view of the same biological experiment.

FIG. 11H shows data from the cell death graph in FIG. 8C are shown. N=5 for each group. Each replicate is an independent field of view of the same biological experiment.

FIG. 11I shows data from the cell death graph in FIG. 8F are shown. N=5 for each group. Each replicate is an independent field of view of the same biological experiment.

FIG. 12A shows data from the cell death graph in FIG. 6B are shown. N=5 for each group. Each replicate is an independent field of view of the same biological experiment.

FIG. 12B shows data from the cell death graph in FIG. 7C are shown. N=5 for each group. Each replicate is an independent field of view of the same biological experiment.

FIG. 12C shows data from the cell death graph in FIG. 7F are shown. N=5 for each group. Each replicate is an independent field of view of the same biological experiment.

FIG. 12D shows data for the glutathione quantifications from FIG. 7B (top graph) are shown. N=3 independent biological experiments.

FIG. 12E shows data from the cell death graph in FIG. 7G are shown. N=5 for each group. Each replicate is an independent field of view of the same biological experiment.

DETAILED DESCRIPTION

Figure 1A:
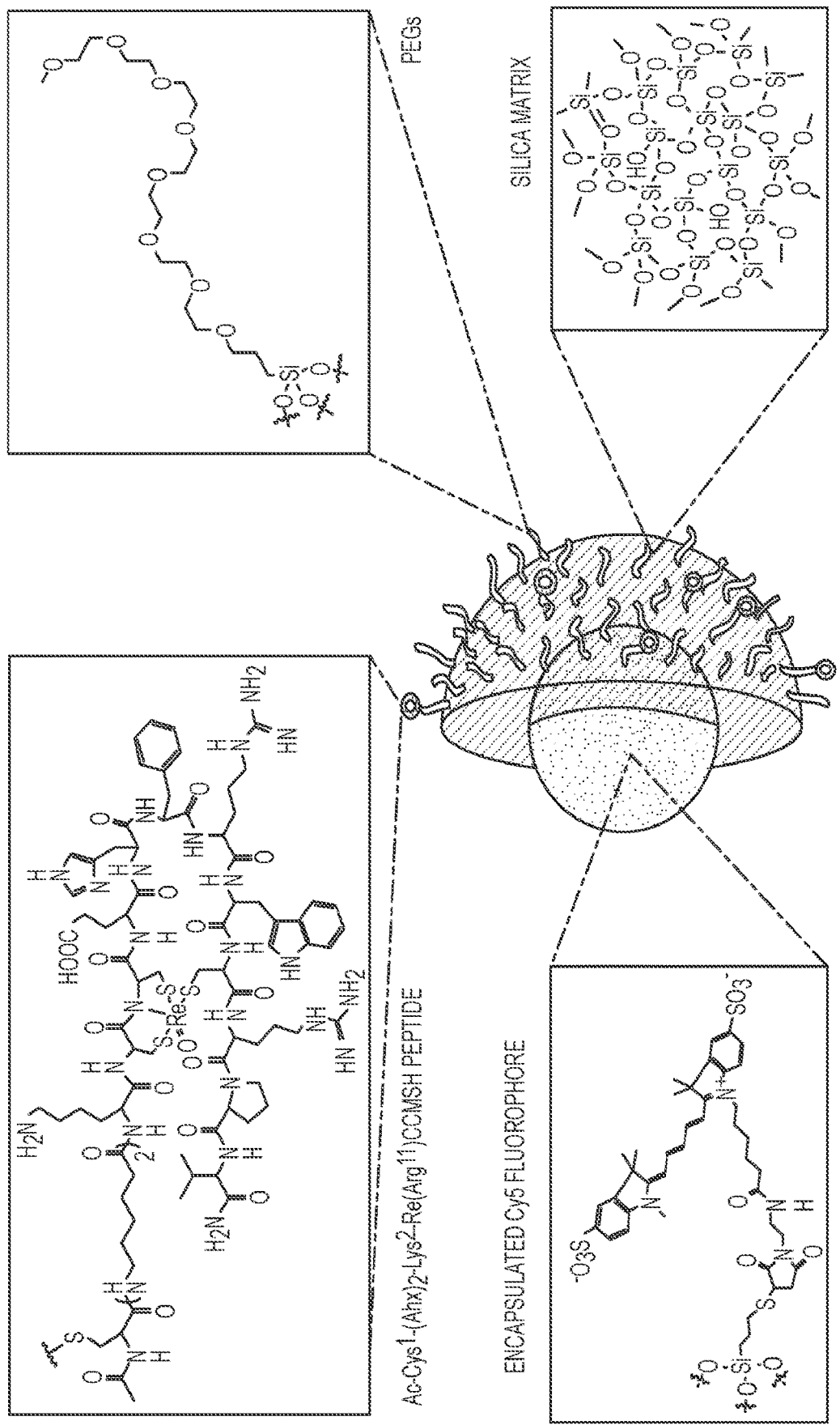
FIGS. 1A-1K show silica-based and ultrasmall α-MSH-PEG-C' dot particles induce cell death in amino acid-deprived conditions.

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Various embodiments described herein utilize ultrasmall FDA-IND approved nanoparticles, such as C and C' dots. Various embodiments described herein demonstrate their adaptation for drug delivery applications and detail cell biological analyses examining (1) how cells and xenograft models respond to melanoma-targeting C' dot (e.g., α-MSH-PEG-C' dots) treatment over a range of concentrations and times (e.g., days to weeks), and (2) whether cellular pathways are affected by particle ingestion were performed.

Described herein is how a combination of treatment of cells with α-MSH-PEG-C' dots and starvation of amino acids synergize to induce the cell death program ferroptosis. Moreover, it is demonstrated herein that concentration- and time-dependent treatment effects on cells using sub-10 nm diameter fluorescent (Cy5 dye-containing) silica nanoparticles, (e.g., C' dots) adapted with melanoma-targeting peptides. The present disclosure describes how high concentrations of ultrasmall nanoparticles (e.g., less than 10 nm in diameter, e.g., C dots or C' dots) induce cell death by the mechanism ferroptosis, which involves iron, reactive oxygen species, and a synchronous mode of cell death execution. In certain embodiments, the high concentration is a local concentration within a range from 0.18 μM to 1.8 μM in tumor tissue of a subject (wherein this range is an estimate based on the mouse studies described herein). In certain embodiments, the high concentration is a local concentration in the tumor tissue of at least 0.18 μM, at least 0.3 μM, at least 0.4 μM, at least 0.5 μM, or at least 0.6 μM; e.g., wherein the nanoparticles are silica-based, e.g., wherein the nanoparticles are C dots or C' dots. In certain embodiments, the local concentration is dependent on tumor type and/or the subject.

The present disclosure describes that high concentrations of these particles were generally well tolerated in both non-cancer and cancer cells cultured in nutrient-replete media. The combination of particle treatment and metabolic (e.g., amino acid) deprivation synergized to kill cancer cells at high rates. Without having to be bound by theory, ingested nanoparticles localize to lysosome networks, but do not inhibit lysosome function, and nanoparticle-induced death occurs independently of the autophagy pathway.

To determine whether these effects extended to nutrient depleted conditions in vivo, xenografts were generated from particle-exposed cancer cells or treated intravenously using a particle multi-dosing strategy. To this end, concentration-dependent sustained growth inhibition was observed, and suppression of tumor growth kinetics coupled with a partial tumor regression occurred. Thus, these data demonstrated that ultrasmall, surface-functionalized silica-based nanoparticles, employed under high concentration and nutrient-deprived conditions, induced cell death by the mechanism ferroptosis.

In certain embodiments, the nanoparticle comprises silica, polymer (e.g., poly(lactic-co-glycolic acid) (PLGA)), biologics (e.g., protein carriers), and/or metal (e.g., gold, iron). In certain embodiments, the nanoparticle is a "C dot" as described in U.S. Publication No. 2013/0039848 A1 by Bradbury et al., which is hereby incorporated by reference.

In certain embodiments, the nanoparticle is spherical. In certain embodiments, the nanoparticle is non-spherical. In certain embodiments, the nanoparticle is or comprises a material selected from the group consisting of metal/semi-metal/non-metals, metal/semi-metal/non-metal-oxides, -sulfides, -carbides, -nitrides, liposomes, semiconductors, and/or combinations thereof. In certain embodiments, the metal is selected from the group consisting of gold, silver, copper, and/or combinations thereof.

The nanoparticle may comprise metal/semi-metal/non-metal oxides including silica ($SiO_2$), titania ($TiO_2$), alumina ($Al_2O_3$), zirconia ($Z_rO_2$), germania ($GeO_2$), tantalum pentoxide ($Ta_2O_5$), $NbO_2$, etc., and/or non-oxides including metal/semi-metal/non-metal borides, carbides, sulfide and nitrides, such as titanium and its combinations (Ti, $TiB_2$, TiC, TiN, etc.).

The nanoparticle may comprise one or more polymers, e.g., one or more polymers that have been approved for use in humans by the U.S. Food and Drug Administration (FDA) under 21 C.F.R. § 177.2600, including, but not limited to, polyesters (e.g., polylactic acid, poly(lactic-co-glycolic acid), polycaprolactone, polyvalerolactone, poly(1,3-dioxan-2-one)); polyanhydrides (e.g., poly(sebacic anhydride)); polyethers (e.g., polyethylene glycol); polyurethanes; polymethacrylates; polyacrylates; polycyanoacrylates; copolymers of PEG and poly(ethylene oxide) (PEO).

The nanoparticle may comprise one or more degradable polymers, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly (glycolic acid) (PGA), poly(caprolactone) (PCL), poly(lactide-co-glycolide) (PLG), poly(lactide-co-caprolactone) (PLC), and poly(glycolide-co-caprolactone) (PGC). Another exemplary degradable polymer is poly (beta-amino esters), which may be suitable for use in accordance with the present application.

In certain embodiments, a nanoparticle can have or be modified to have one or more functional groups. Such functional groups (within or on the surface of a nanoparticle) can be used for association with any agents (e.g., detectable entities, targeting entities, therapeutic entities, or PEG). In addition to changing the surface charge by introducing or modifying surface functionality, the introduction of different functional groups allows the conjugation of linkers (e.g., (cleavable or (bio-)degradable) polymers such as, but not limited to, polyethylene glycol, polypropylene glycol, PLGA, etc.), targeting/homing agents, and/or combinations thereof.

In certain embodiments, the nanoparticle comprises one or more targeting ligands (or moieties) (e.g., attached thereto), such as, but not limited to, small molecules (e.g., folates, dyes, etc), aptamers (e.g., A10, AS1411), polysaccharides, small biomolecules (e.g., folic acid, galactose, bisphosphonate, biotin), oligonucleotides, and/or proteins (e.g., (poly)peptides (e.g., αMSH, RGD, octreotide, AP peptide, epidermal growth factor, chlorotoxin, transferrin, etc), antibodies, antibody fragments, proteins, etc.). In certain embodiments, the nanoparticle comprises one or more contrast/imaging agents (e.g., fluorescent dyes, (chelated) radioisotopes (SPECT, PET), MR-active agents, CT-agents), and/or therapeutic agents (e.g., small molecule drugs, therapeutic (poly)peptides, therapeutic antibodies, (chelated) radioisotopes, etc).

In certain embodiments, PET (Positron Emission Tomography) tracers are used as imaging agents. In certain embodiments, PET tracers comprise $^{89}$Zr, $^{64}$Cu, [$^{18}$F] fluorodeoxyglucose. In certain embodiments, the nanoparticle includes these and/or other radiolabels. In certain embodiments, the one or more targeting ligands (or moieties) can be of the same type, or can be different species.

In certain embodiments, the nanoparticle comprises one or more fluorophores. Fluorophores comprise fluorochromes, fluorochrome quencher molecules, any organic or inorganic dyes, metal chelates, or any fluorescent enzyme substrates, including protease activatable enzyme substrates. In certain embodiments, fluorophores comprise long chain carbophilic cyanines. In other embodiments, fluorophores comprise DiI, DiR, DiD, and the like. Fluorochromes comprise far red, and near infrared fluorochromes (NIRF). Fluorochromes include but are not limited to a carbocyanine and indocyanine fluorochromes. In certain embodiments, imaging agents comprise commercially available fluorochromes including, but not limited to Cy5.5, Cy5 and Cy7 (GE Healthcare); AlexaFlour660, AlexaFlour680, AlexaFluor750, and AlexaFluor790 (Invitrogen); VivoTag680, VivoTag-S680, and VivoTag-S750 (VisEn Medical); Dy677, Dy682, Dy752 and Dy780 (Dyomics); DyLight547, DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); and ADS780WS, ADS830WS, and ADS832WS (American Dye Source) and Kodak X-SIGHT 650, Kodak X-SIGHT 691, Kodak X-SIGHT 751 (Carestream Health).

In certain embodiments, the nanoparticle comprises (e.g., has attached) one or more targeting ligands, e.g., for targeting cancer tissue/cells of interest.

Cancers that may be treated include, for example, prostate cancer, breast cancer, testicular cancer, cervical cancer, lung cancer, colon cancer, bone cancer, glioma, glioblastoma, multiple myeloma, sarcoma, small cell carcinoma, melanoma, renal cancer, liver cancer, head and neck cancer, esophageal cancer, thyroid cancer, lymphoma, pancreatic (e.g., BxPC3), lung (e.g., H1650), and/or leukemia.

In certain embodiments, the nanoparticle comprises a therapeutic agent, e.g., a drug (e.g., a chemotherapy drug) and/or a therapeutic radioisotope. As used herein, "therapeutic agent" refers to any agent that has a therapeutic effect and/or elicits a desired biological and/or pharmacological effect, when administered to a subject.

In certain embodiments, e.g., where combinational therapy is used, an embodiment therapeutic method includes administration of the nanoparticle and administration of one or more drugs (e.g., either separately, or conjugated to the nanoparticle), e.g., one or more chemotherapy drugs, such as sorafenib, paclitaxel, docetaxel, MEK162, etoposide, lapatinib, nilotinib, crizotinib, fulvestrant, vemurafenib, bexorotene, and/or camptotecin.

The surface chemistry, uniformity of coating (where there is a coating), surface charge, composition, concentration, frequency of administration, shape, and/or size of the nanoparticle can be adjusted to produce a desired therapeutic effect, e.g., ferroptosis of cancer cells.

In certain embodiments, nanoparticle drug conjugates (NDCs) are used for drug delivery applications. Detail on NDCs are described, for example, in International publication WO 2015/183882 A1, the contents of which is hereby incorporated by reference it its entirety.

EXAMPLES

Figure 1B:
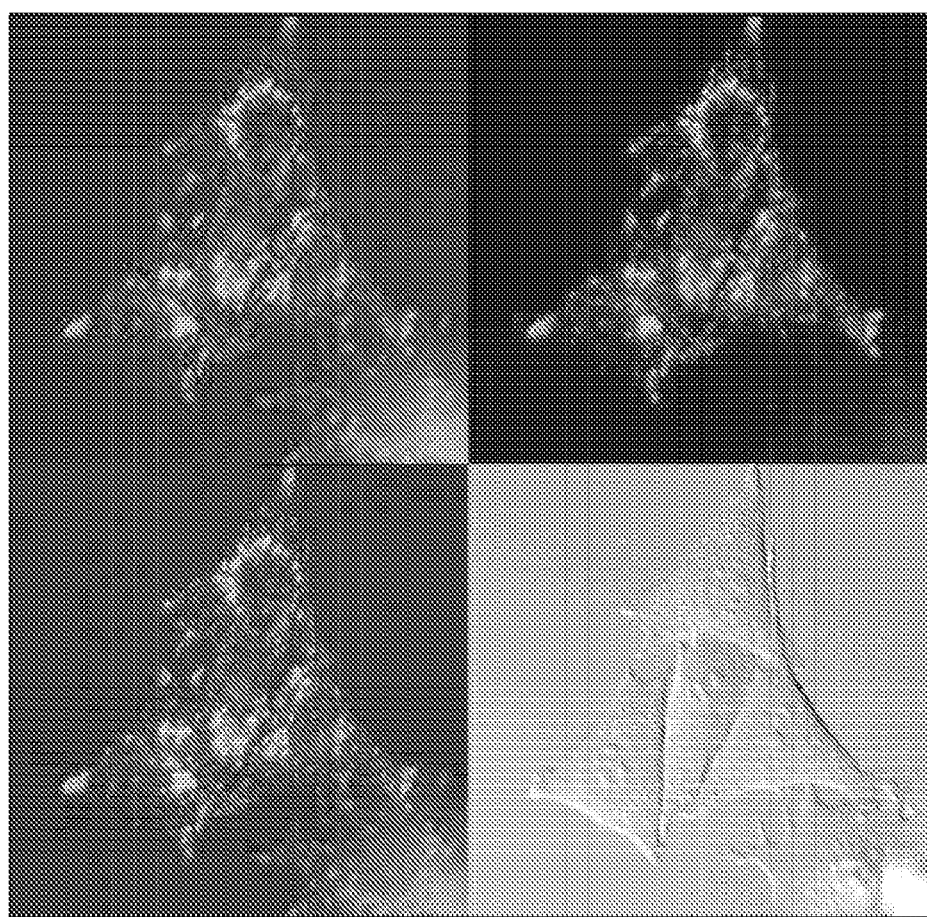
Figure 1C:
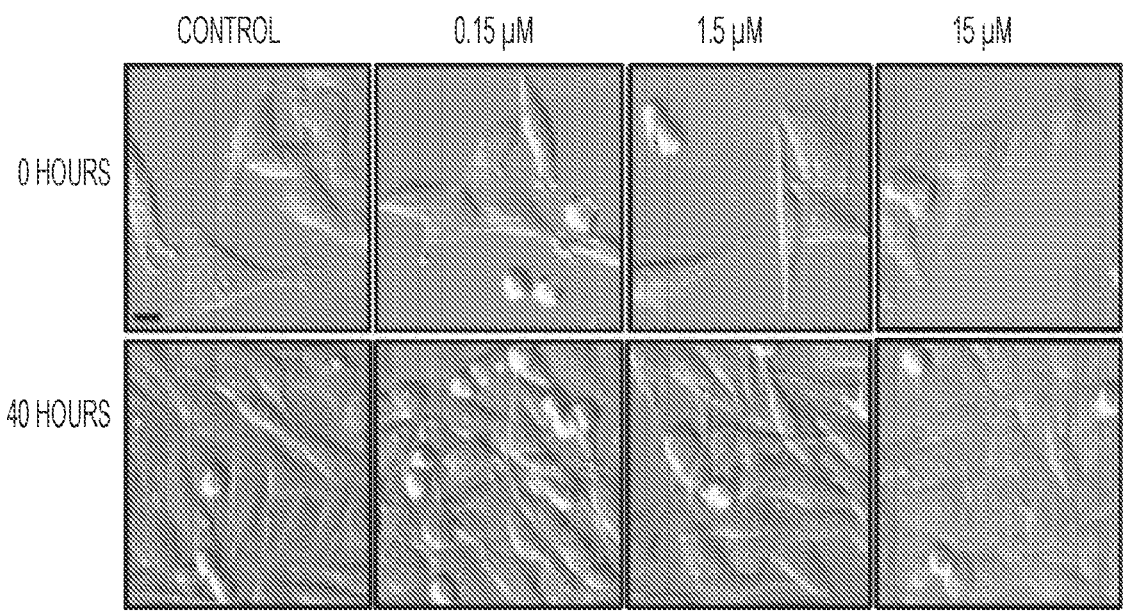
Figures 1D, 1E:
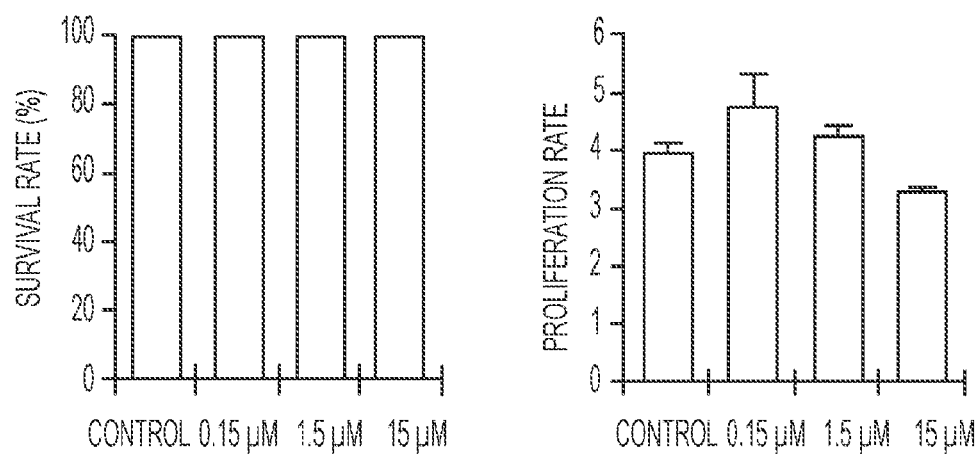
Figure 1F:
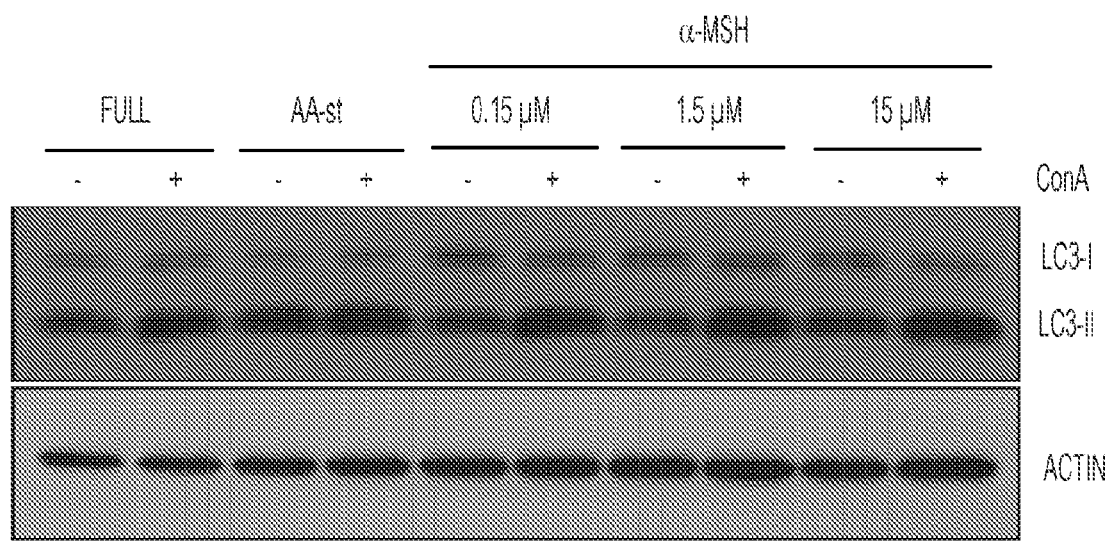
Figures 1G, 1H:
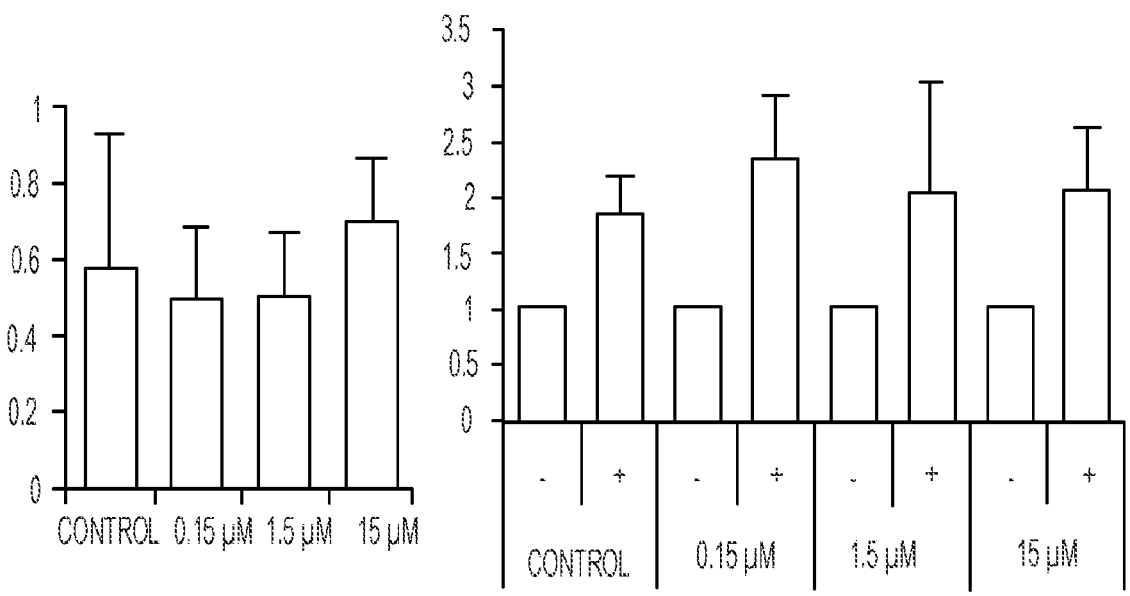

As described herein, MC1-R-targeting C' dots were used to enhance cellular uptake (FIG. 1A). Live imaging of MC1-R expressing human melanoma cells (M21) cells treated with particles for 24 hours revealed colocalization of α-MSH-PEG-C' dots with lysosomes. Colocalization was visualized by expression of a GFP-tagged lysosomal-associated membrane protein 1 (LAMP1) to indicate that ingested particles resided in lysosomal or late endosomal networks (FIG. 1B). M21 cells treated with increasing concentrations of α-MSH-PEG-C' dot particles up to 15 μM showed similar survival and proliferation rates to the rates observed in control cells (FIGS. 1C-1E). These results demonstrated that incubation with high concentrations of these nanoparticles are well-tolerated by cells. It was next examined if lysosomes were functioning properly within cells treated with α-MSH-PEG-C' dots. To determine this, the autophagy pathway, which targets intracellular substrates for lysosomal degradation, was examined. Autophagy was examined by quantifying the basal levels and turnover rates of the autophagy protein microtubule-associated protein 1 light chain 3 (LC3), which is lipidated onto autophagosomal membranes and becomes degraded following the fusion of autophagosomes with lysosomes. The accumulation of the autophagosome-associated, lipidated form of LC3 (called LC3-II) was quantified as a measure of flux through lysosomes or ameasure of autophagy induction versus the cytosolic, non-lipidated form (called LC3-I) by western blotting (FIGS. 1F-1H).

The turnover of LC3-II that occurs in a lysosome-dependent manner can also be measured as a readout of lysosome function. When lysosomes are functioning properly, treatment with lysosomal inhibitors such as concanamycin A (ConA), which inhibits the lysosomal vacuolar-type H+-ATPase (V-ATPase), leads to accumulation of LC3-II due to a lack of degradation. In contrast, if lysosomes are dysfunctional, treatment with ConA will not change LC3-II levels. Cells treated with increasing concentrations of α-MSH-PEG-C' dots for 24 hours, from 0.15 μM to 15 μM, had similar relative LC3-II levels compared to control cells, suggesting that autophagy is not induced or perturbed by nanoparticle treatment. The treatment of cells with a lysosomal inhibitor ConA, which inhibits lysosome function by increasing pH and blocks autophagosome degradation, resulted in a similar accumulation of LC3-II in particle-treated cells as compared to controls demonstrating that lysosomes are functioning properly even when cells are loaded with high concentrations of α-MSH-PEG-C' dots (FIGS. 1F-1H).

Figure 1I:
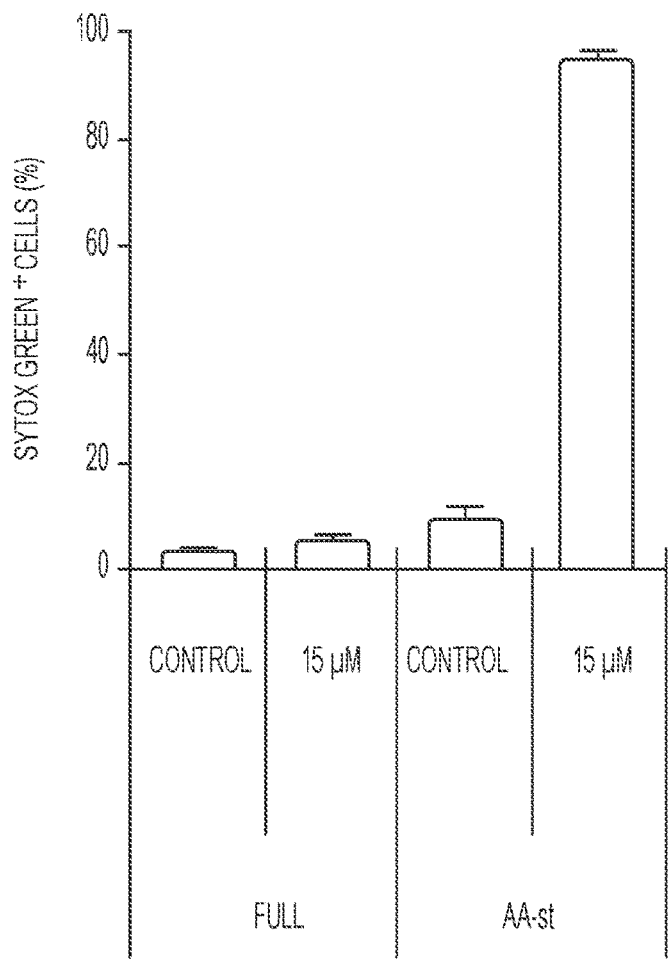
Figure 1J:
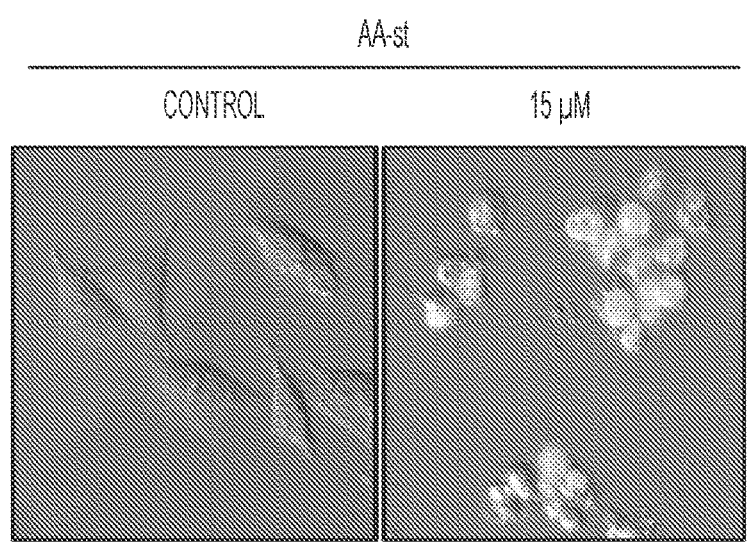
Figure 1K:
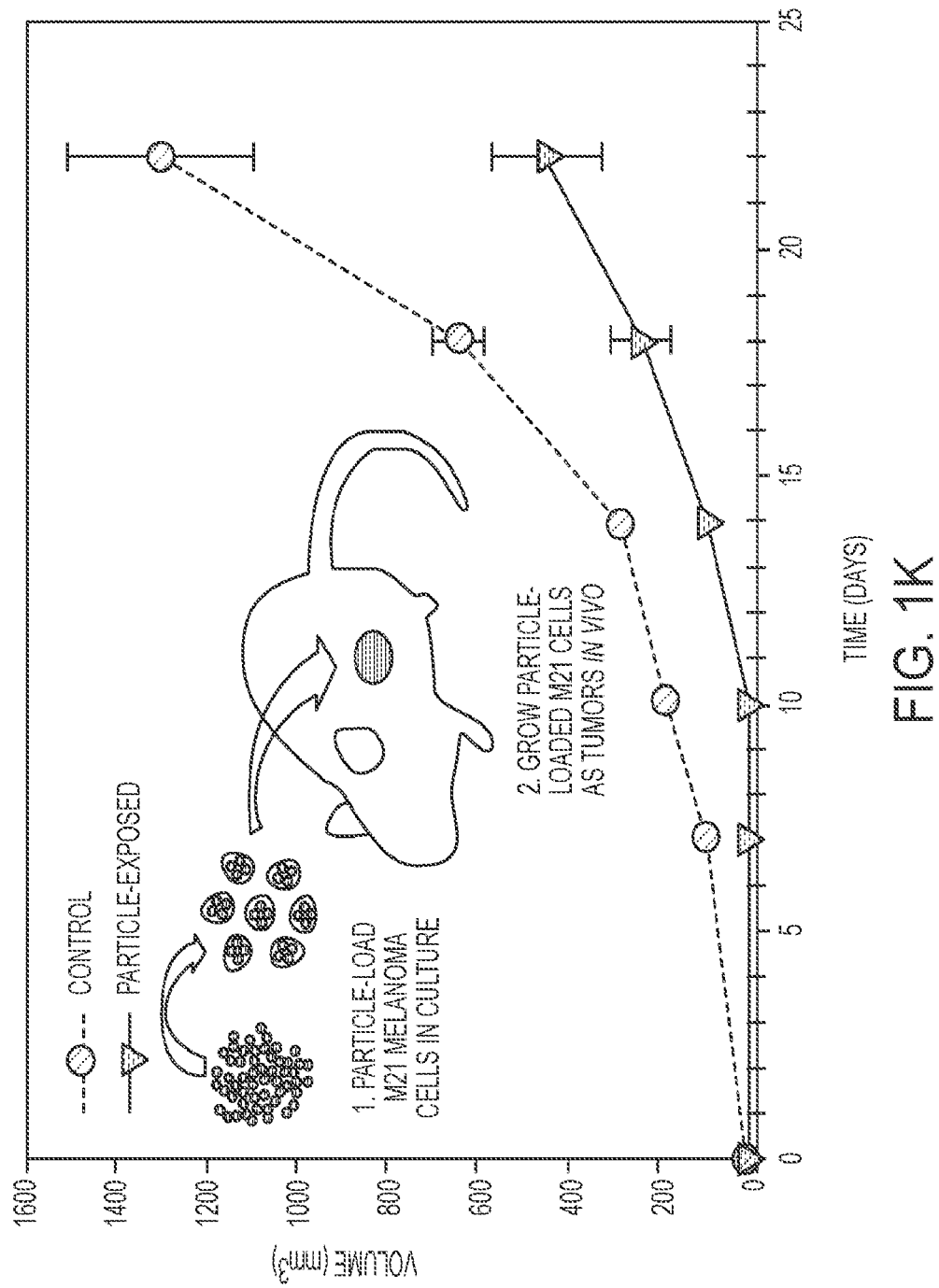

Next, nanoparticles were administered to cells cultured under nutrient-deprived conditions to induce autophagy. Cells cultured in amino acid-free media were treated with α-MSH-PEG-C' dots and examined by time lapse imaging. While amino acid deprivation was well-tolerated by M21 cells in the absence of particles, the treatment of amino acid-deprived cells with 15 μM α-MSH-PEG-C' dots, which had no effect on cells in nutrient-replete media, led to cell death at high rates. Cell death was detected by the uptake of Sytox Green, a membrane-impermeable nucleic acid dye that labels cells with ruptured plasma membranes (FIG. 1I-1J). This demonstrates that while α-MSH-PEG-C' dots are generally well-tolerated, nutrient-deprived cancer cells are sensitive to treatment. To determine whether this finding could have consequences for tumor growth in vivo, M21 melanoma cells were incubated with α-MSH-PEG-C' dots in culture under nutrient-replete conditions, which had no effect on cell viability (FIGS. 1C-1E and FIGS. 8E-8F), and then injected particle-exposed cells, as well as particle-unexposed cells, into mice as flank tumor xenografts to promote a nutrient-deprived state. M21 melanoma cells loaded with αMSH-PEG-C' dots demonstrated statistically significant growth-inhibition (p<0.001) relative to non-particle exposed cells. No measurable tumor growth occurred from particle-exposed cells up to 10 days following cell injection. Without having to be bound by theory, these findings suggested that treatment with high concentrations of α-MSH-PEG-C' dots may induce cell death under conditions of nutrient deprivation in culture and in vivo.

Figure 2A:
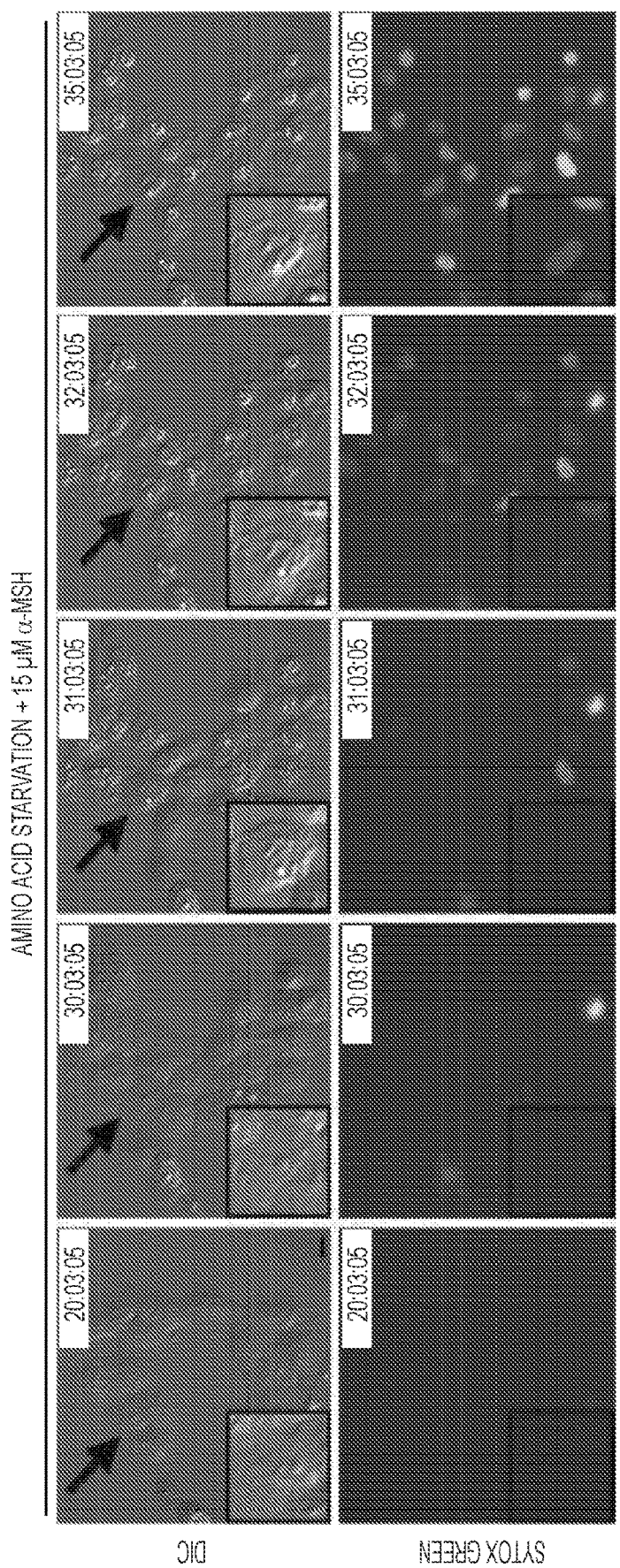
FIGS. 2A-2F show α-MSH-PEG-C' dot particle-induced cell death is not apoptosis, necroptosis or autosis.
Figures 2B, 2C:
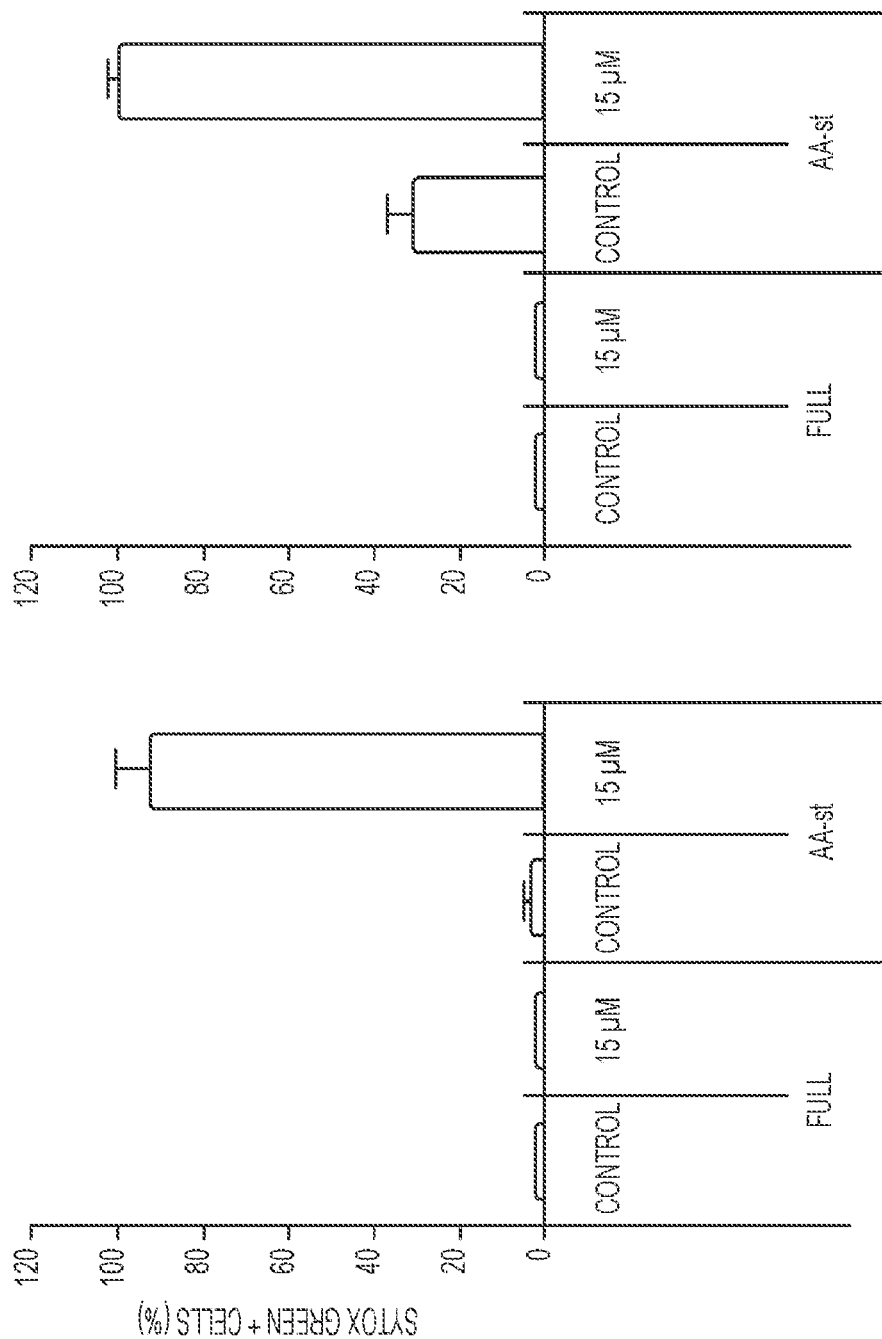
Figure 2D:
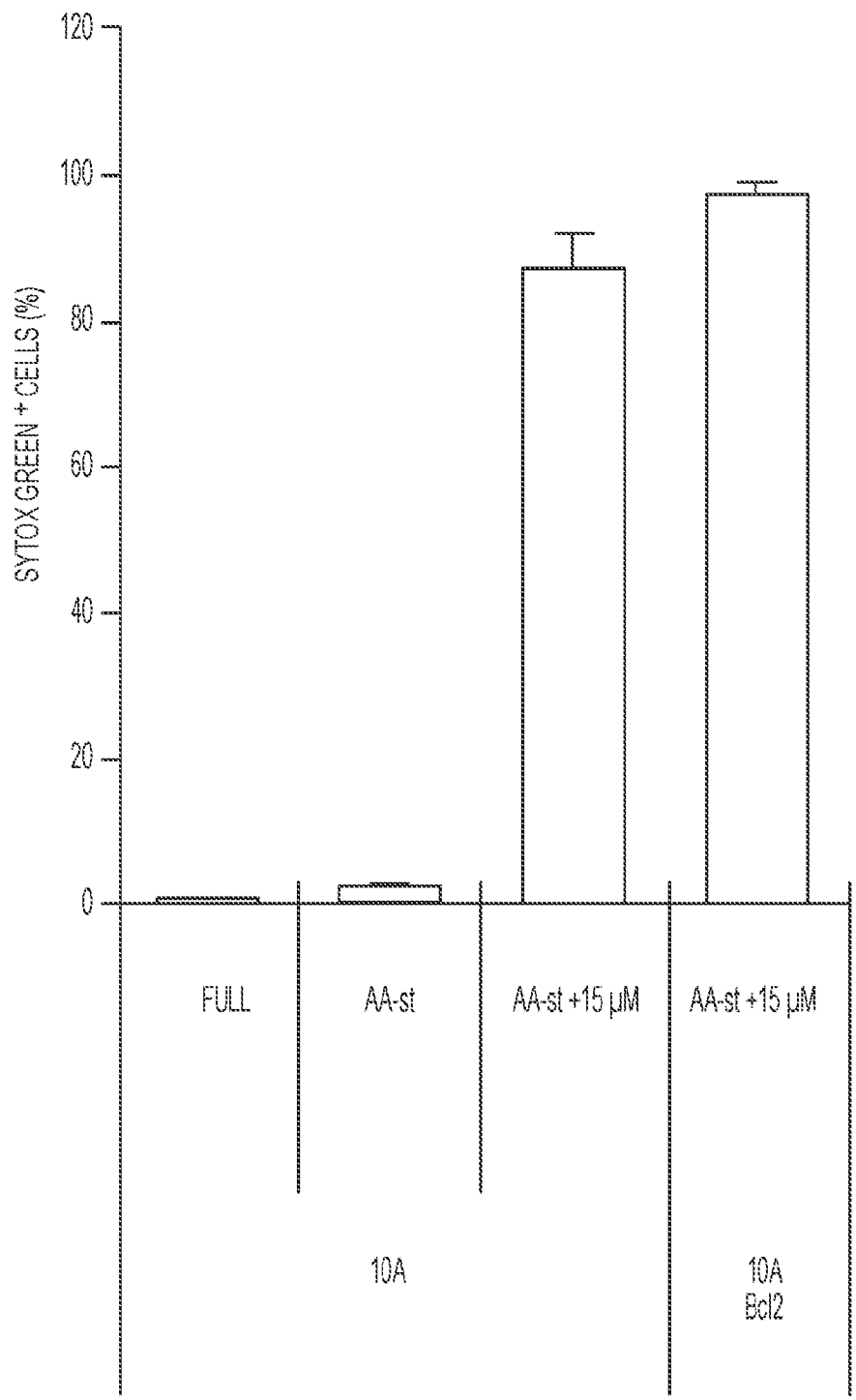
Figure 2E:
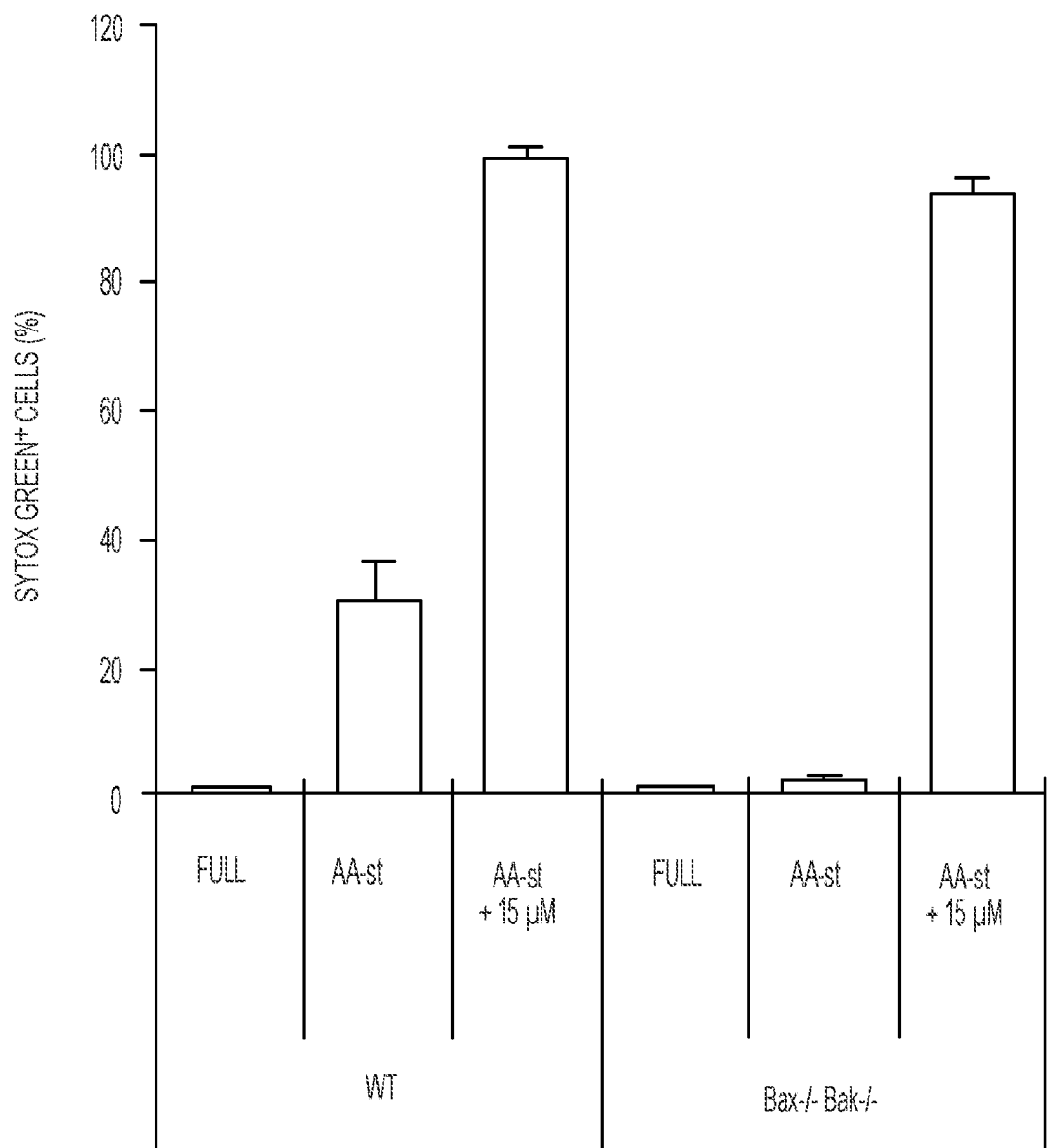
Figure 8A:
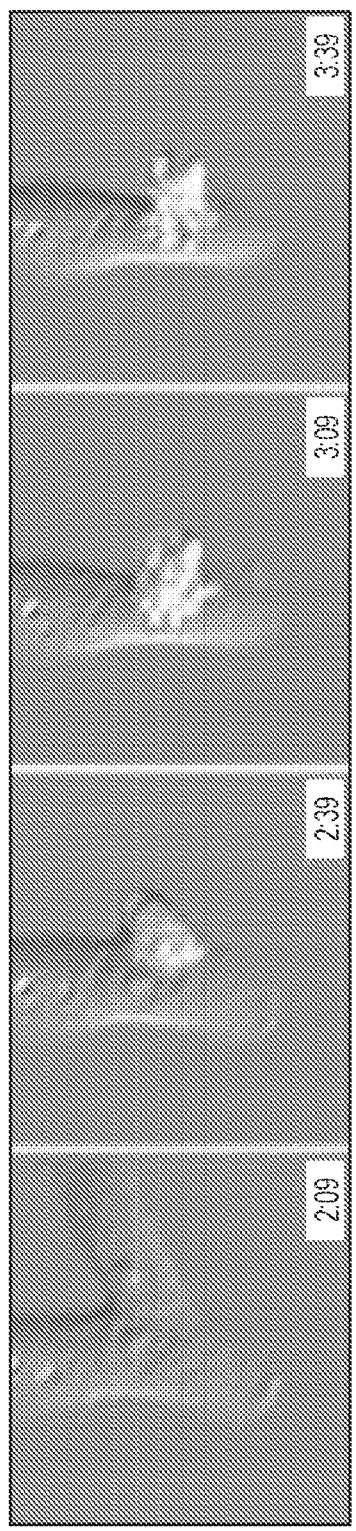
FIGS. 8A-8G show control assays for apoptosis and necroptosis-inhibited cells and Liproxstatin-1.
Figure 8B:
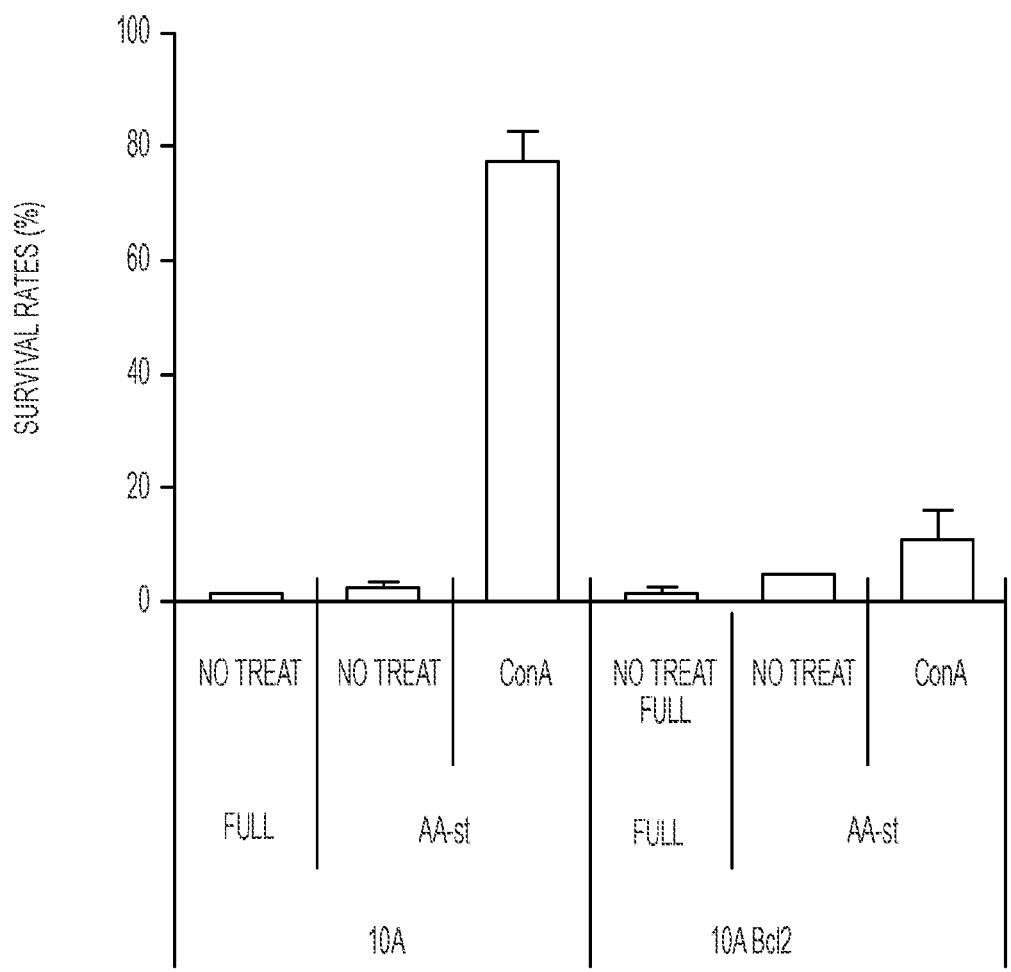

Next, the mechanism of how cells treated with α-MSH-PEG-C' dots undergo cell death under nutrient-deprived conditions was investigated. Without having to be bound by theory, inspection of the morphology of dying cells suggested a form of necrosis, causing the cells to swell and the plasma membrane to rupture without cell blebbing and fragmentation that is typically observed during apoptosis (FIG. 2A and FIG. 8A). In order to more definitively identify the mechanism of cell death, two non-tumor cell lines, MCF10A human mammary epithelial cells and mouse embryo fibroblasts (MEF) were utilized and also observed to die at high rates when cultured in amino acid-free media in the presence of α-MSH-PEG-C' dots (FIGS. 2B-2C). Cells rendered resistant to apoptosis, by overexpression of the anti-apoptotic protein Bcl-2 (MCF10A-Bcl2) (FIG. 8B) or by genetic deletion of Bax and Bak (Bax/Bak-/-MEFs) underwent cell death at rates similar to rates of control cells, suggesting that α-MSH-PEG-C' dot-induced cell death does not occur by apoptosis (FIG. 2D and FIG. 2E).

Figure 2F:
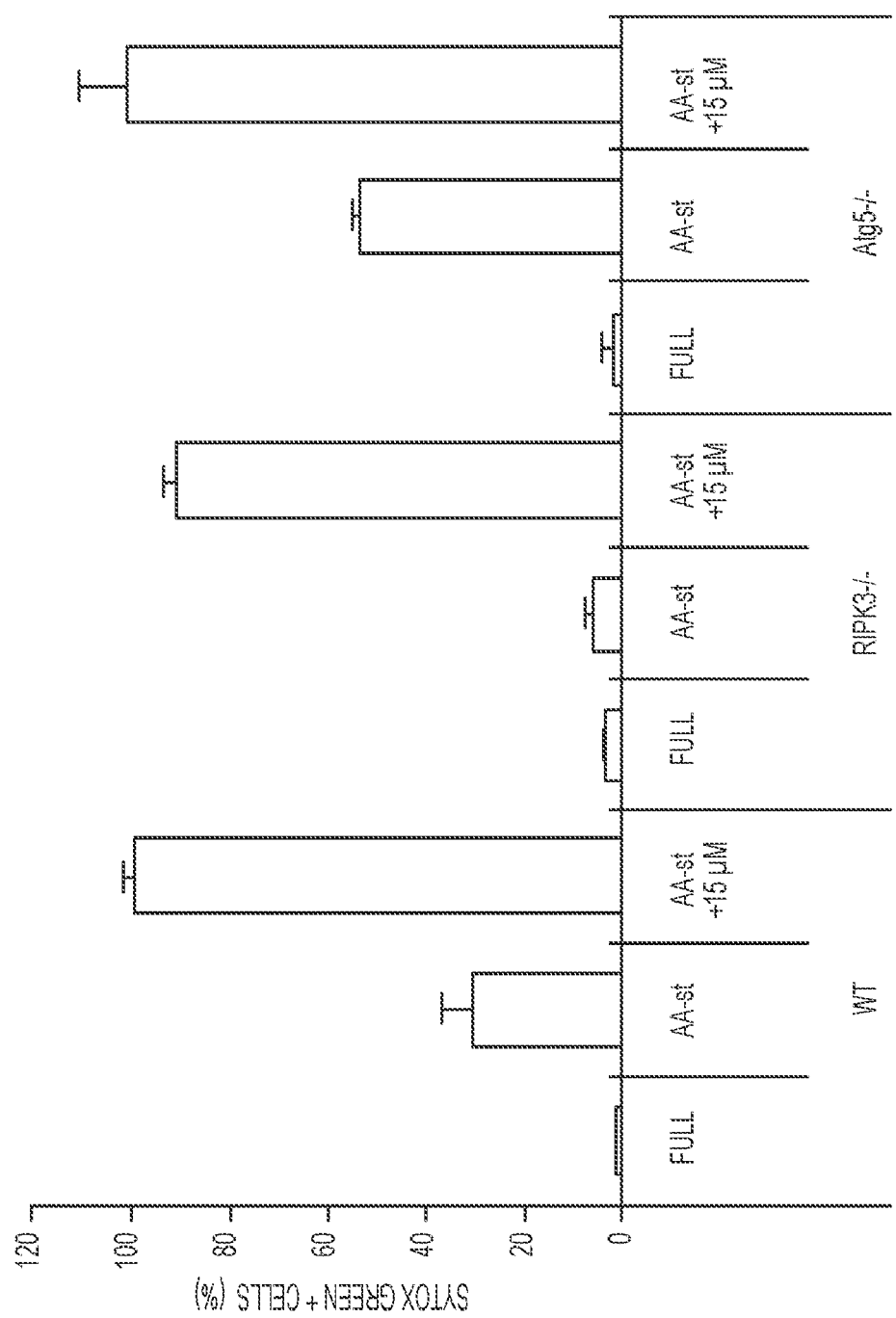
Figure 8C:
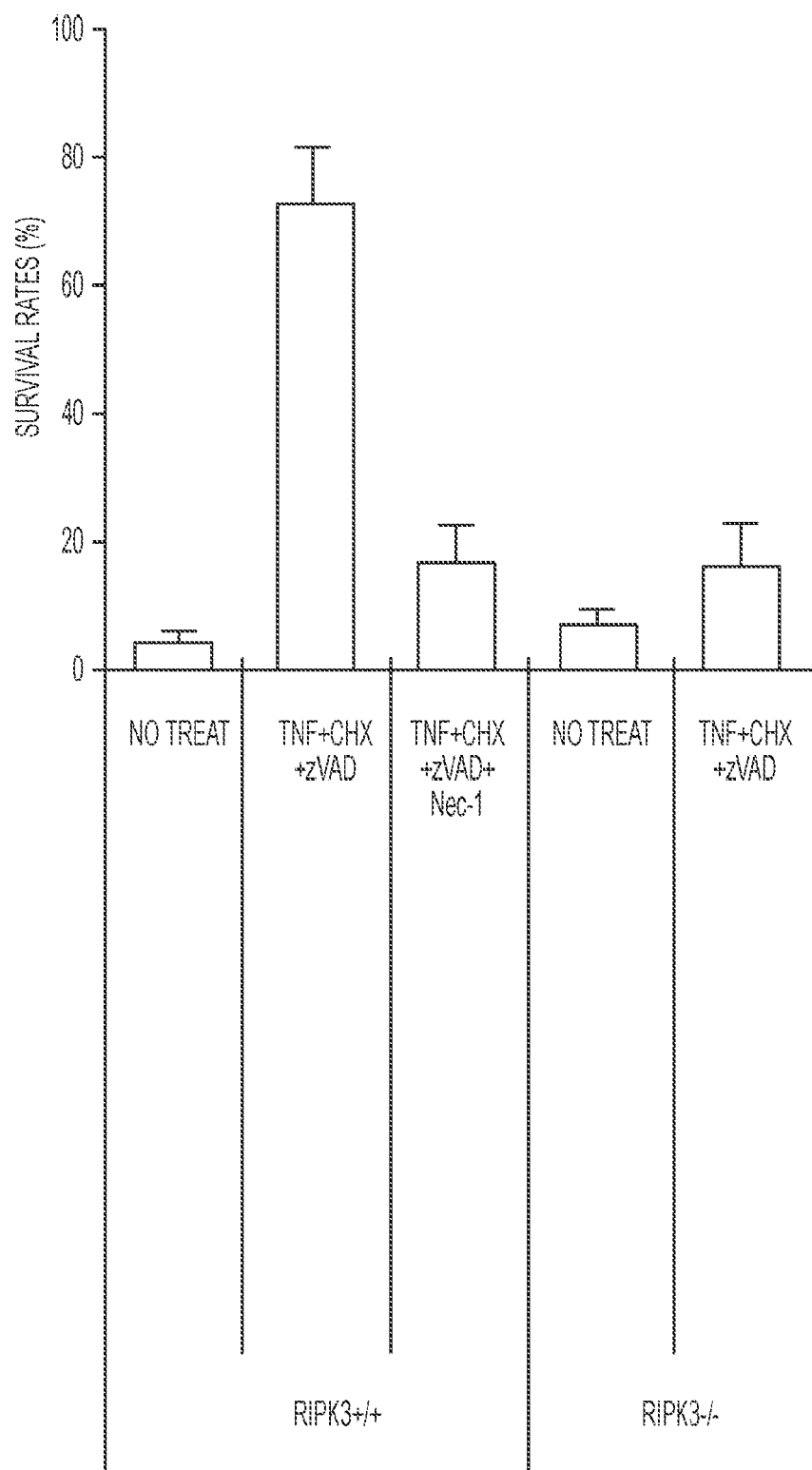

Next, it was determined if cell death was occurring by necroptosis, a programmed form of necrosis that requires the RIPK3 kinase. Similar to the Bax/Bak-/-MEFs, Ripk3-/-knockout MEFs, which are resistant to necroptosis (FIG. 8C), also underwent cell death at similar rates compared to controls. Without having to be bound by theory, this result suggested that nanoparticle treatment does not induce necroptosis (FIG. 2F).

Next, it was determined if a recently-described form of cell death involving the autophagy pathway, called autosis, may be involved by treating autophagy-related gene 5 knockout MEFs (Atg5-/-MEFs) that are completely deficient for autophagy with α-MSH-PEG-C' dots in the absence of amino acids. Atg5-/-MEFs underwent cell death at similar rates to control cells, demonstrating that α-MSH-PEG-C' dot-induced cell death does not involve autophagy, and is not autosis (FIG. 2F). Together, these data demonstrated that cell death induced by a combination of α-MSH-PEG-C' dot treatment and amino acid deprivation occurs independently of apoptosis, necroptosis, and autosis.

Figure 3A:
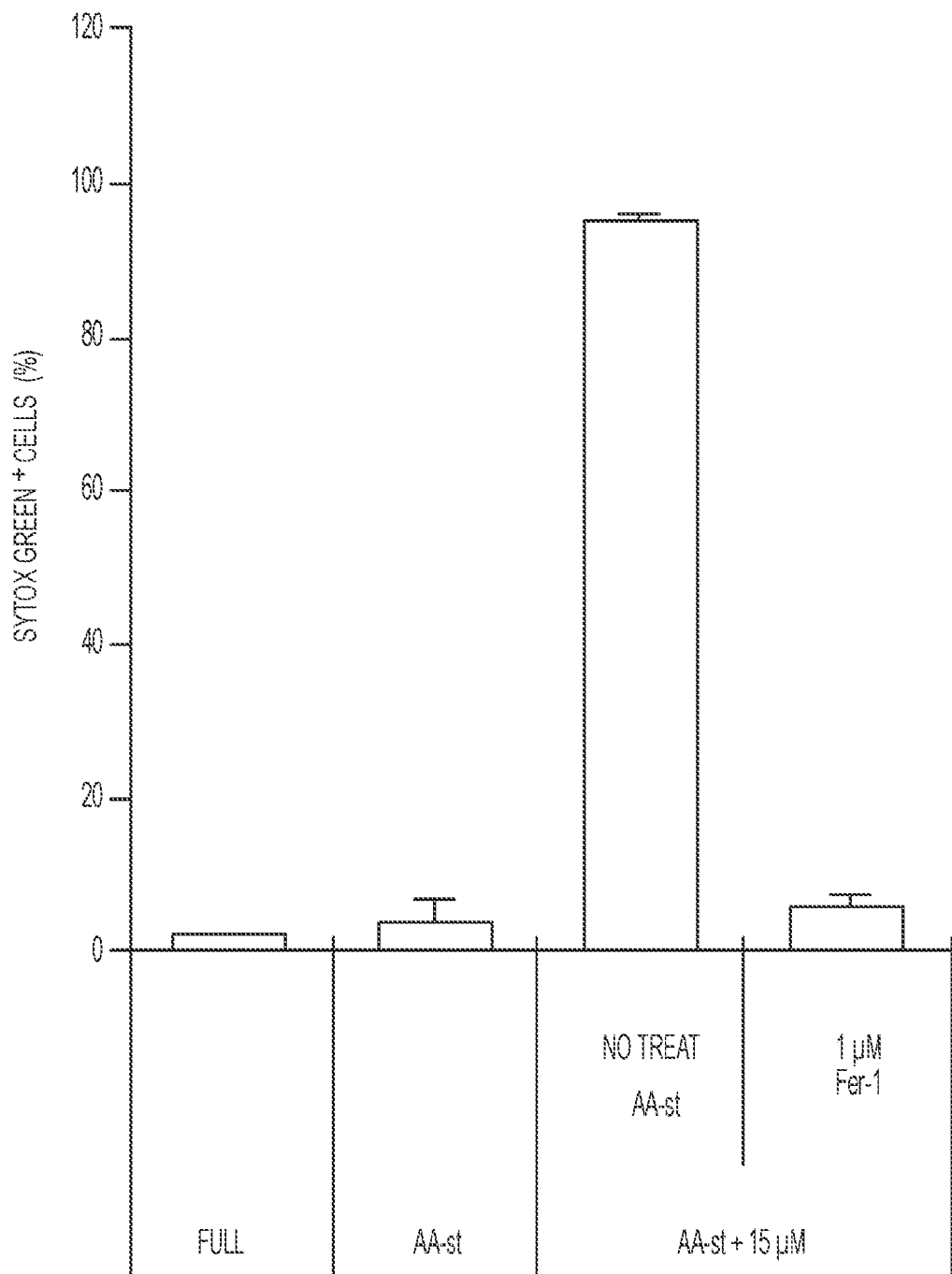
Figure 8D:
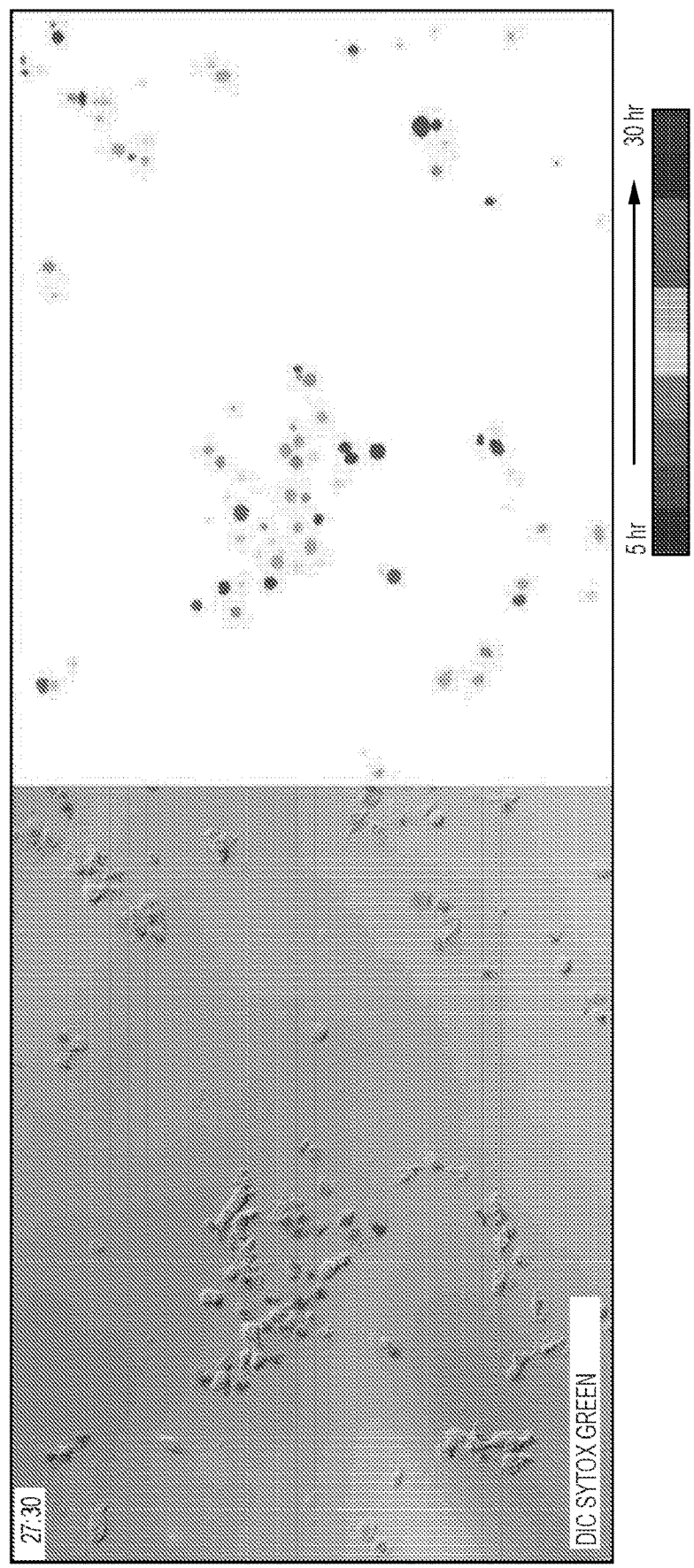
Figure 8E:
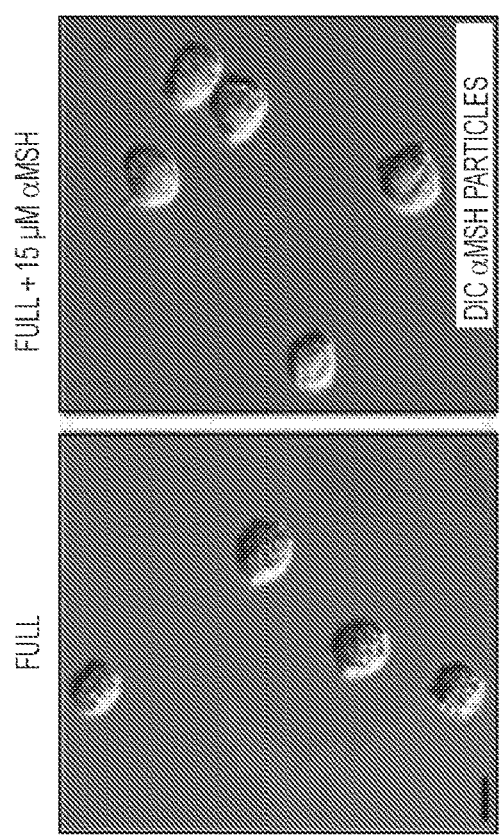
Figure 8F:
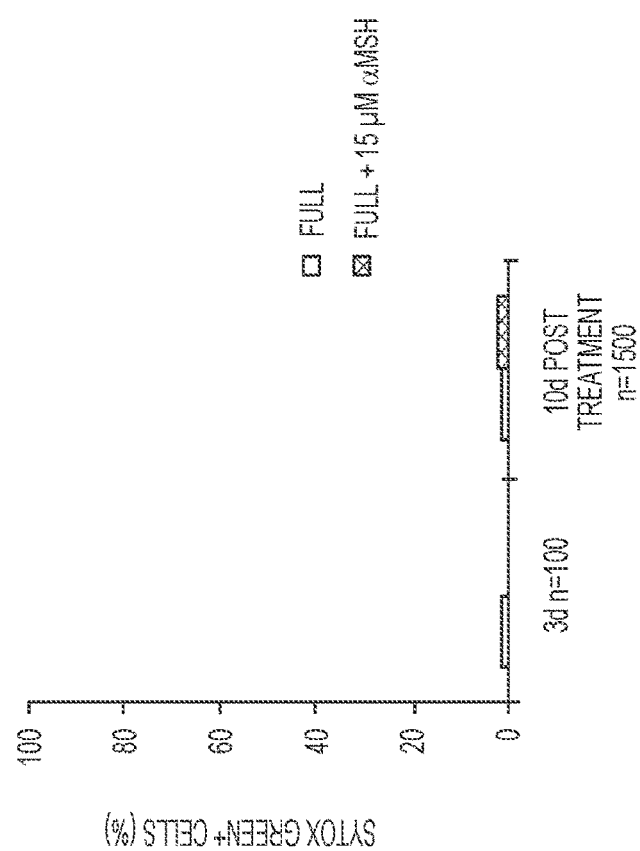
Figure 8G:
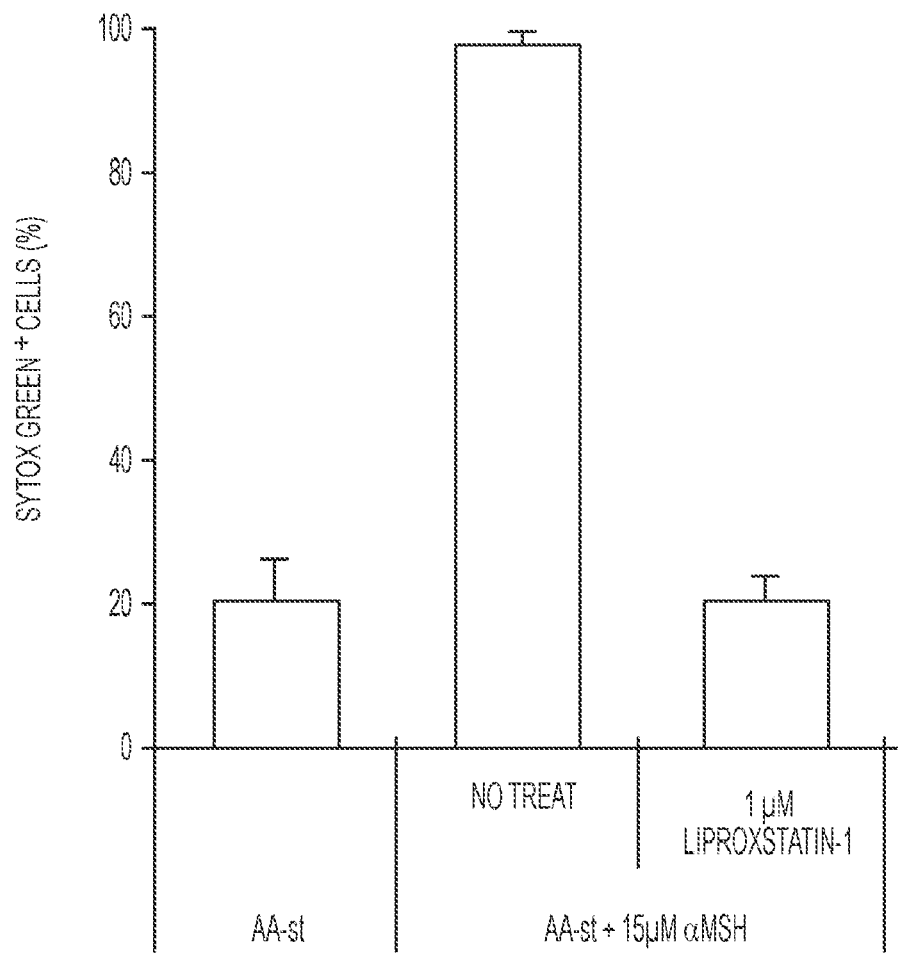

It was next determined if ferroptosis, a recently described cell death mechanism that occurs via an iron- and lipid reactive oxygen species (ROS)-dependent process, is induced by glutathione depletion and involved in α-MSH-PEG-C' dot-induced cell death. It was first determined if ferrostatin-1 and liproxstatin-1, pharmacological inhibitors of ferroptosis that are scavengers of lipid ROS, can block cell death in this context. Treatment with either ferrostatin-1 or liproxstatin-1 rescued cell viability, reducing cell death to the level that occurs under amino acid-deprived conditions in the absence of nanoparticles (FIG. 3A, FIG. 8G).

Figure 3B:
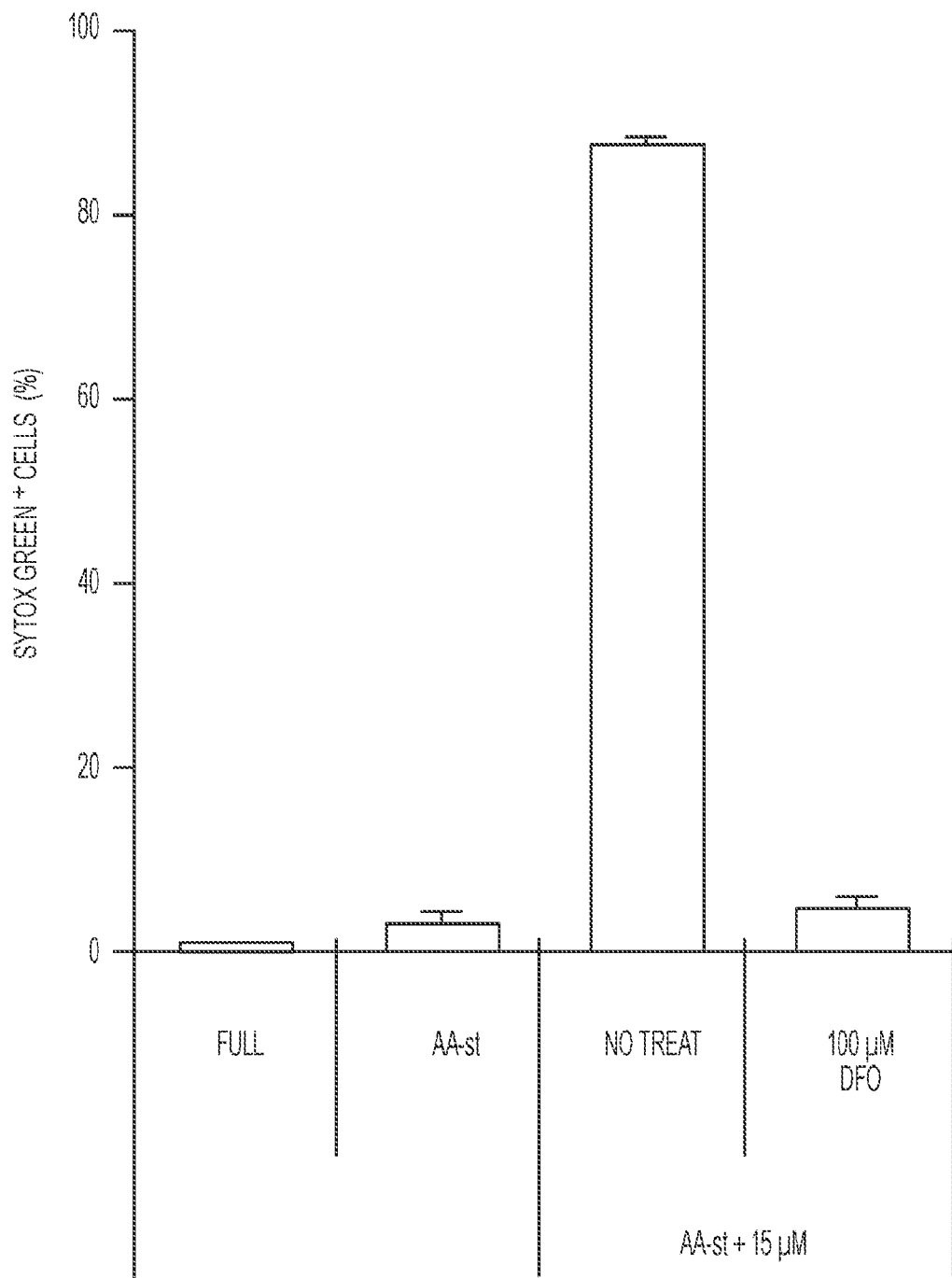
Figure 3C:
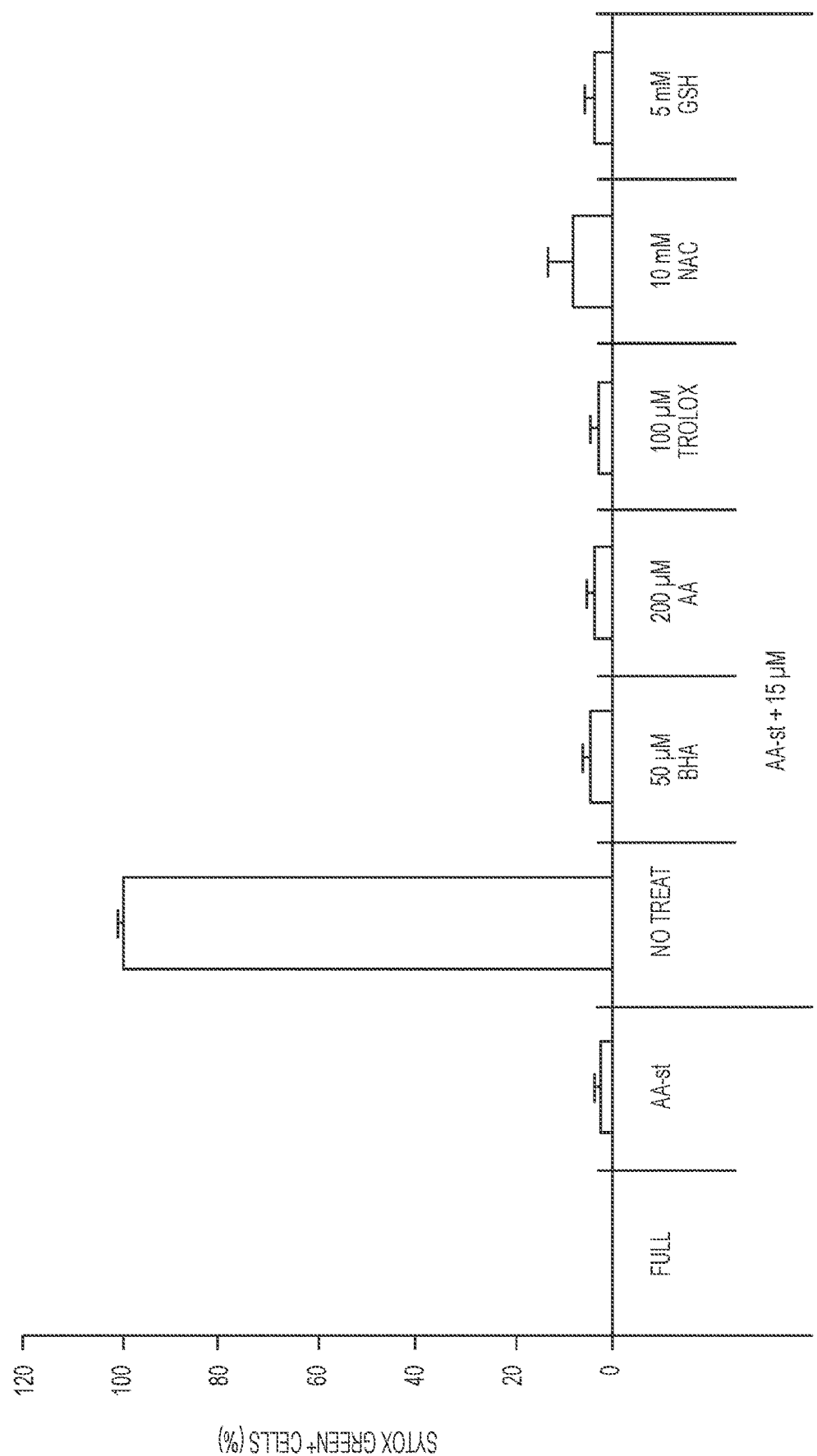
Figure 3D:
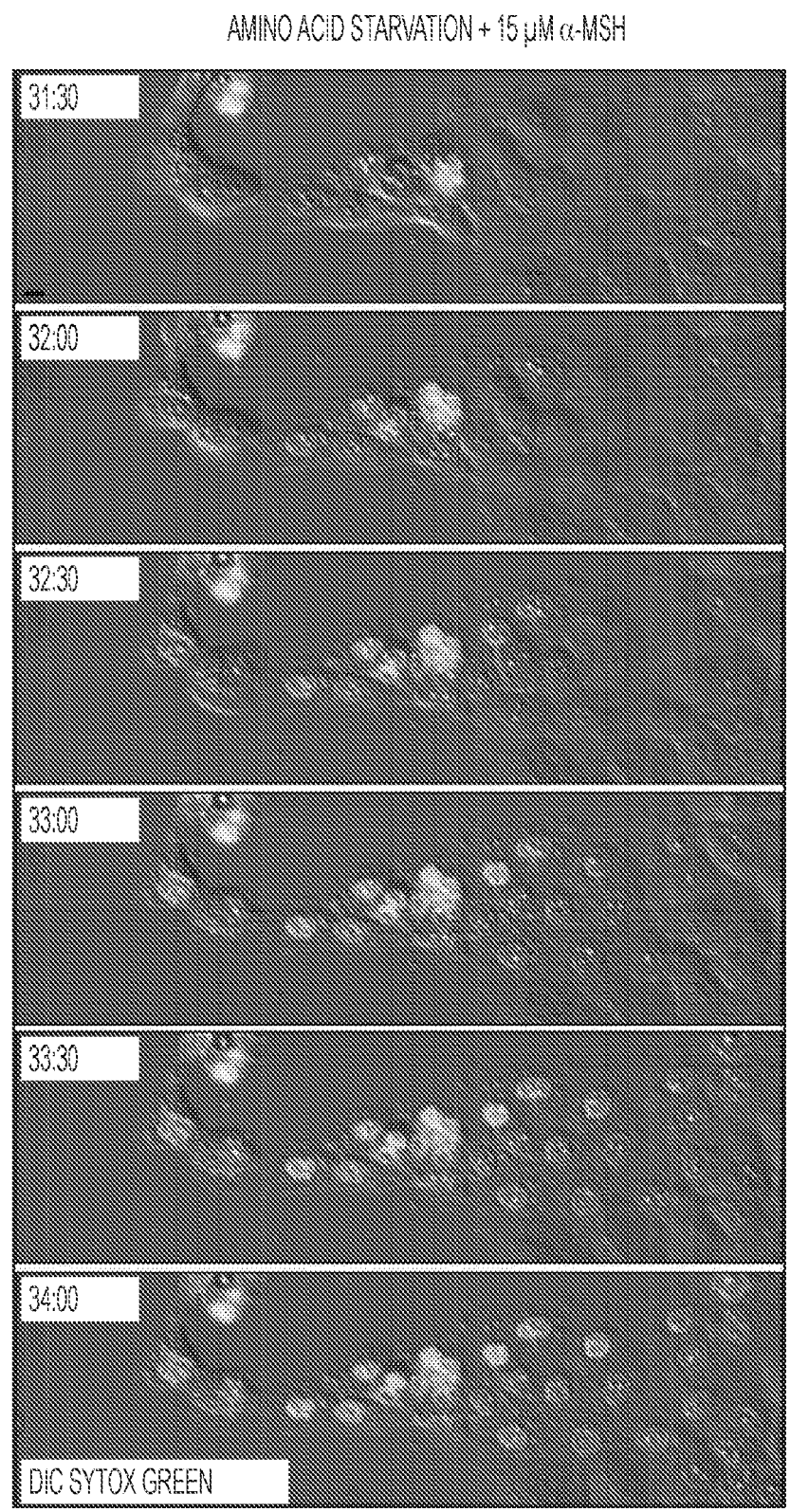
Figure 3E:
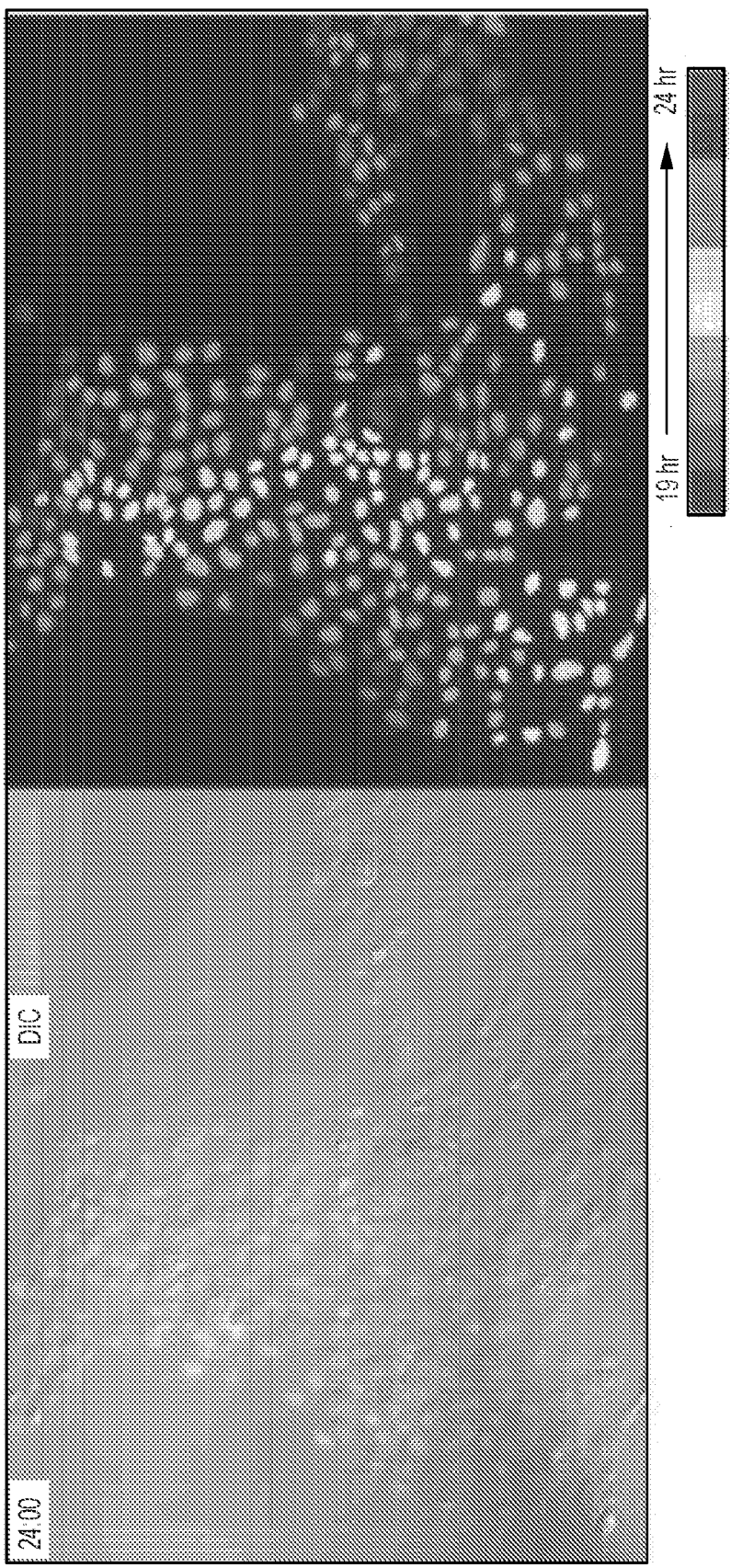
Figure 8H:
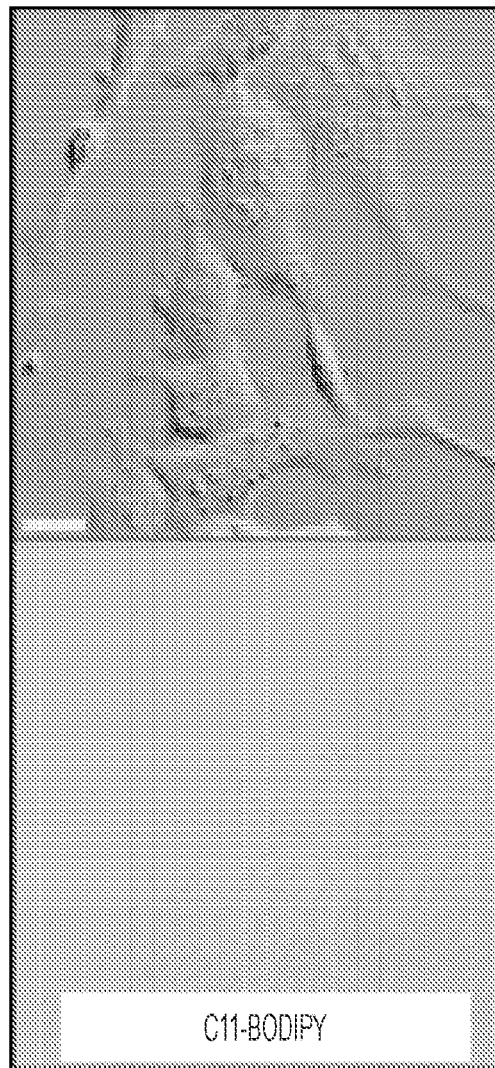
FIG. 8H shows that liproxstatin-1 treatment inhibits C11-BODIPY staining induced by erastin treatment. Image shows C11-BODIPY-incubated cells treated with erastin (5 µM), 6 hours after control cells underwent cell death as in FIGS. 3F-3G. Note the absence of C11-BODIPY staining in erastin+liproxtstatin-1-treated cells.

Nanoparticle-induced cell death was also inhibited by treatment with other antioxidants, including butylated hydroxyanisole (BHA), ascorbic acid (Asc Acid) and trolox, or, alternatively, by glutathione repletion through the addition of glutathione or N-acetylcysteine (NAC), a precursor of glutathione (FIGS. 2B-2C). To examine if lipid ROS accumulates during nanoparticle-induced cell death, particle-exposed cells were imaged in the presence of the lipid oxidation indicator C11-BODIPY. Increased staining prior to cell death was seen to occur in response to treatment with the known ferroptosis-inducing agent erastin, in a liproxstatin-1-inhibitable manner (FIGS. 3F-G, FIG. 8H). Like cell death induced by erastin treatment, lipid ROS detected by C11-BODIPY staining accumulated several hours prior to the induction of cell death by nanoparticle treatment under amino acid-free conditions (FIGS. 3F-3G). To further examine if nanoparticle-induced death is dependent on iron, a requirement for ferroptosis, it was found that cells treated with deferoxamine (DFO), an iron chelator used for treating iron overload and an agent reported to block ferroptosis, almost completely inhibited cell death (FIG. 3B). These data demonstrate that treatment of amino acid-starved cells with high α-MSH-PEG-C' dot concentrations induces ferroptosis (FIG. 3C). Notably, ferroptosis in this context was also observed to propagate from cell to cell in a wave-like manner (FIGS. 3D and 3E), unlike that found for cells undergoing other types of death such as apoptosis (FIG. 8D). Without having to be bound by theory, this suggested cell to cell communication of a death-inducing signal.

After determining that MCF10A cells and MEFs undergo cell death by ferroptosis, it was determined if cell death can be induced in this manner by amino acid deprivation and nanoparticle treatment in a wider panel of cancer cells. For example, MCF10A, MEF, and M21 cells, BxPC3 pancreatic carcinoma cells, H1650 lung carcinoma cells, HT1080 fibrosarcoma cells, and 786-0 renal carcinoma cells also underwent high rates of necrosis when treated with α-MSH-PEG-C' dots in the absence of amino acids. This data indicated that cell death can be induced by nanoparticles in the absence of amino acids in a variety of different cancer cell types (FIGS. 4A-4F, FIGS. 6C-6E).

Notably, HT-1080 cells underwent necrosis in response to nanoparticle treatment when cultured in full media (FIGS. 4E-4F) and in starvation media at 10-fold lower particle concentrations (FIG. 6B), suggesting that these cells are particularly sensitive to this form of cell death.

Figure 5A:
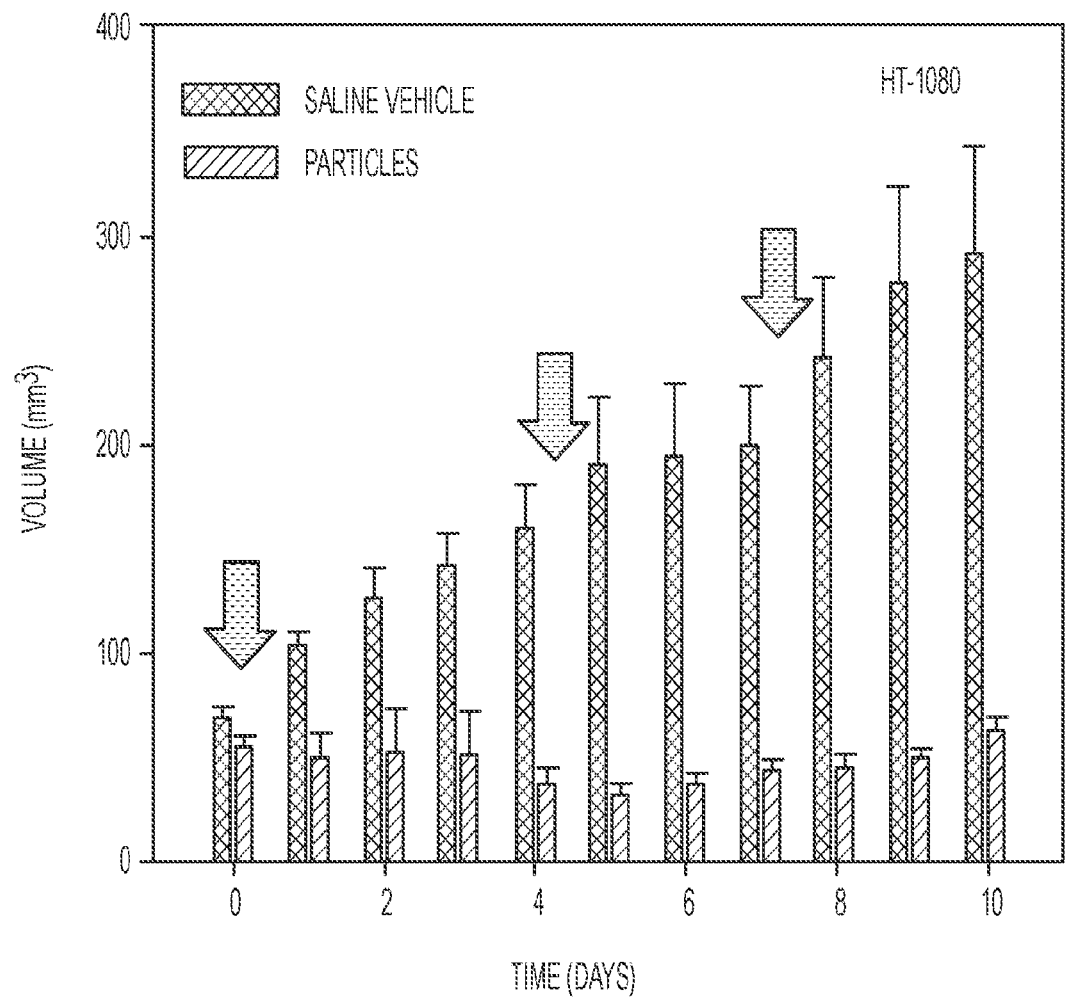
Figure 5B:
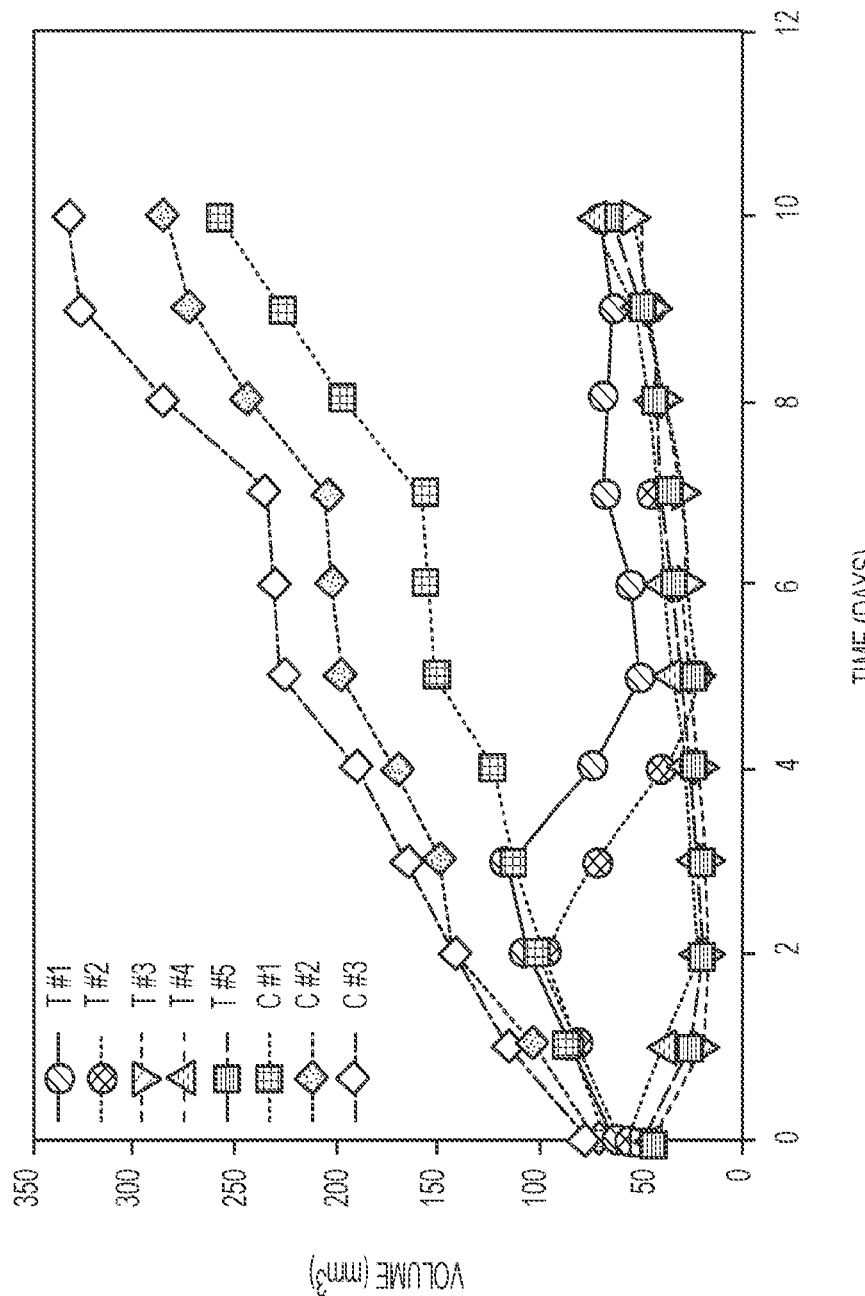

Based on these results, it was further determined if particle-induced treatment responses can be generated in 786-0 renal carcinoma and HT1080 fibrosarcoma xenograft models. Using a multi-dosing delivery scheme, tumor growth was assessed over a 10-day period after three high-dose intravenous (i.v.) treatments of either the targeted particle probe (n=5) or 0.9% saline solution (n=3) in immunosuppressed mice bearing flank 786-0 or HT-1080 tumors. Relative to the rapidly increasing tumor volumes with time measured after injection with saline vehicle, statistically significant inhibition of tumor growth was observed with multiple-dose particle treatments over the experiment interval for both tumor types (FIGS. 5A, 5B, 5I, 5K), but greater for HT-1080 xenografts. Notably, this was accompanied by partial tumor regression that exceeded 50% for all particle-treated HT-1080 tumors (e.g., range of partial tumor regression from 57%-78%; having a mean partial tumor regression of about 64%) within a 4 to 5 day interval after initial injection (FIG. 5B). Over the remainder of the experiment interval, particle-treated tumor volumes decreased. For example, by the end of the 10 day experiment period, treated HT-1080 tumor volumes showed statistically significant reductions of about 85% (p<0.001) relative to control volumes and treated 786-0 tumor volumes showed statistically significant reductions of about 73% (p<0.01) (FIGS. 5A, 5B). Representative whole-body optical imaging in mice bearing HT1080 flank xenografts demonstrated intense fluorescence signal at the site of tumor placement after initial αMSH-PEG-C' dot injections, suggesting localization of the intravenously injected particles (FIG. 5C).

Corresponding H&E-stained tissue sections from representative control (n=1) and treated (n=2) tumors (FIG. 5D) revealed a densely cellular and invasive neoplasm exhibiting multifocal necrosis. Control tumors were significantly larger on average than treated tumors without evident morphological differences. Immunohistochemical staining for the macrophage marker Mac-2 revealed large numbers of recruited macrophages surrounding treated tumors relative to that seen around control tumors, both at low and high magnification (FIGS. 5E-5H). Intratumor Mac-2 positive cells were present in similarly small numbers in all tumors.

Figure 5J:
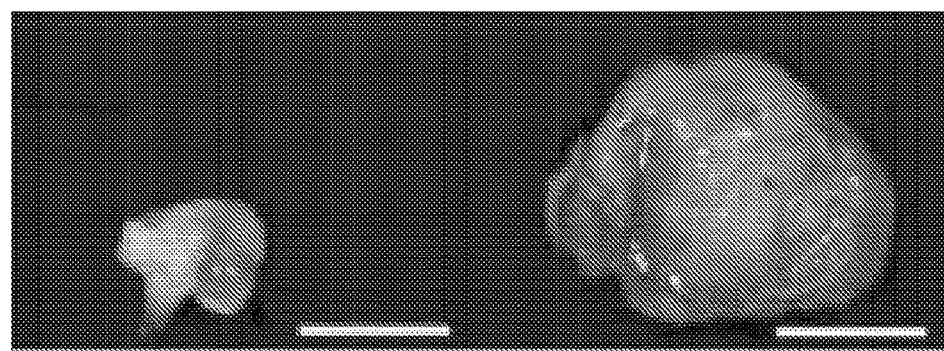
Figure 5K:
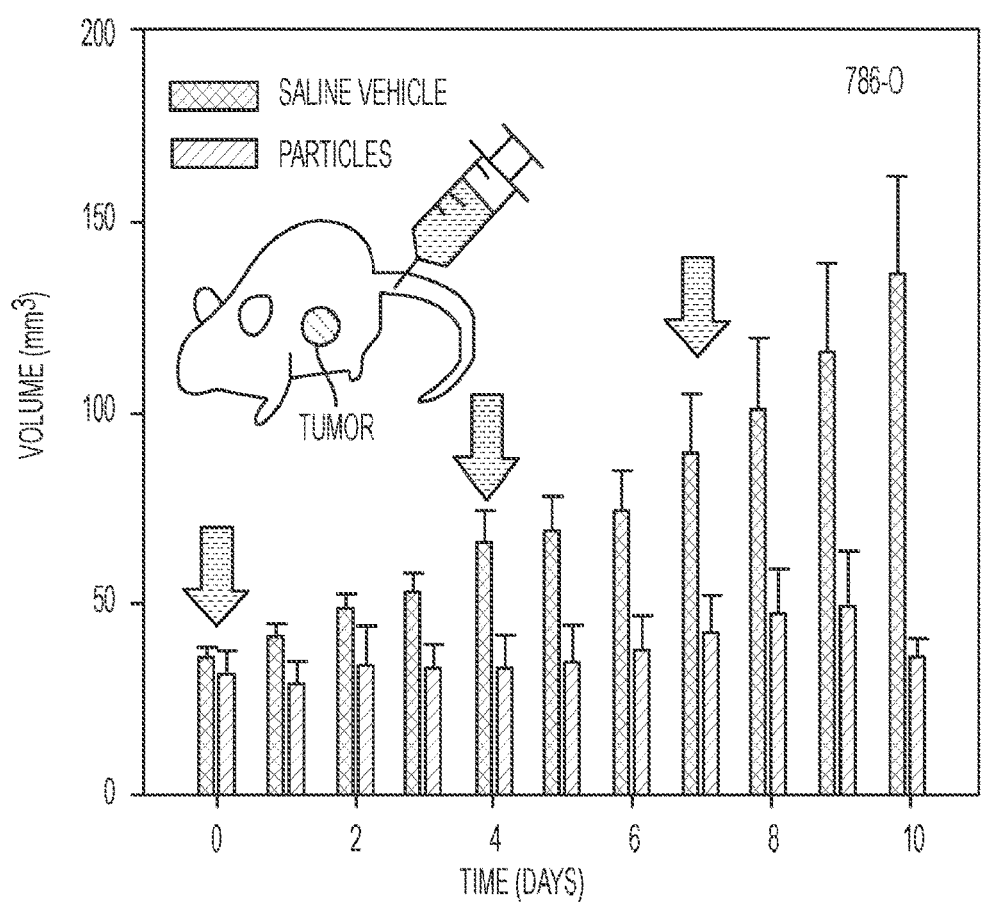

To further examine if the inhibition of tumor growth resulting from nanoparticle treatment could be related to ferroptosis, tumor-bearing mice were treated with daily intraperitoneal (i.p.) doses of liproxstatin-1 over a 10-day period to determine the effects on particle-induced tumor shrinkage. In HT1080 xenografted mice (n=3), subsequently administered three high-dose particle treatments liproxstatin-1 significantly reduced growth inhibition to levels nearly equivalent to those seen in tumors not exposed to particles (FIG. 5I). Average daily growth in particle-exposed tumors treated with liproxstatin-1 was 14.6 mm$^3$ (95% CI: 10.1-18.9), as compared with −0.87 mm$^3$ (95% CI: −1.06 to −0.69) for particle treatment alone, a difference of 15.3 mm$^3$ (CI: 13.1 to 17.6; p<0.001). Corresponding particle-exposed tumor specimens were significantly smaller on average than particle-treated tumors receiving daily liproxstatin-1 (FIG. 5J).

Combined treatment of cells with α-MSH-PEG-C' dots and amino acid starvation synergized to induce the cell death program ferroptosis and that high-dose delivery of nanoparticles can inhibit tumor growth and cause tumor regression; these effects can be reversed in the presence of liproxstatin-1. For example, the combined requirement of nutrient deprivation and nanoparticle treatment for ferroptosis induction in this context may engage tumor cells in vivo, while sparing normal cells (e.g., as tumor tissues are known to undergo metabolic stress and are nutrient-limited compared to normal tissues). Ultrasmall targeted silica nanoparticles themselves have also been shown to preferentially accumulate in tumor tissue more efficiently than non-tumor tissues when modified with ligands that promote targeting.

As described herein, the accumulation of nanoparticles within HT1080 xenografts after intravenous delivery was found to significantly inhibit tumor growth and induce partial tumor regression. Further addition of liproxstatin-1 reversed these effects to levels nearly equivalent to those seen in tumors not exposed to particles. These finding underscore the potential synergy between particle treatment and nutrient deprivation observed in select cancer types, and without having to be bound to theory, suggest that, by exploiting such a metabolic strategy, engagement of ferroptosis could hold therapeutic potential.

The significance of the marked increase in the number of macrophages about particle-treated tumors relative to that about control tumors is not entirely clear, although their role in disease protection and wound repair by engulfing cellular debris is well-established. It can be further acknowledged a high degree of macrophage plasticity can occur in response to local cues from the tumor microenvironment, and that, upon activation, macrophages can assume a spectrum of roles needed to maintain tissue homeostasis, including shifts in their function associated with tumor shrinkage. These data present a therapeutic application for molecularly-targeted C' dots, already in clinical trials for cancer imaging and detection, but, for example, without the need for surface-attached cytotoxic agents.

Figure 7D:
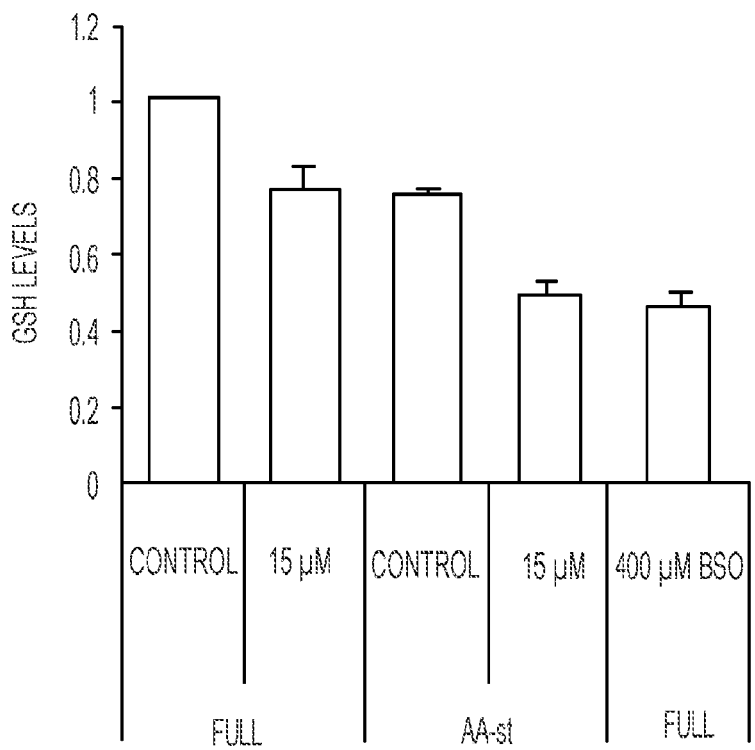
Figure 7E:
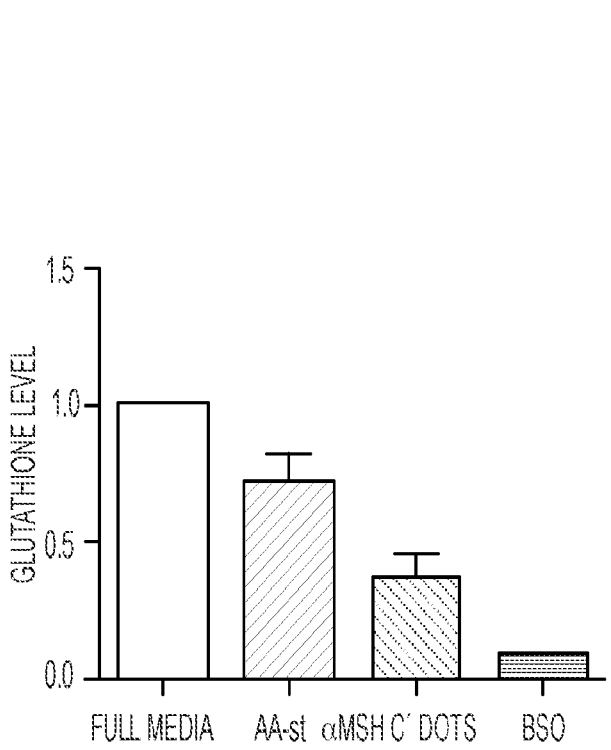
Figure 7F:
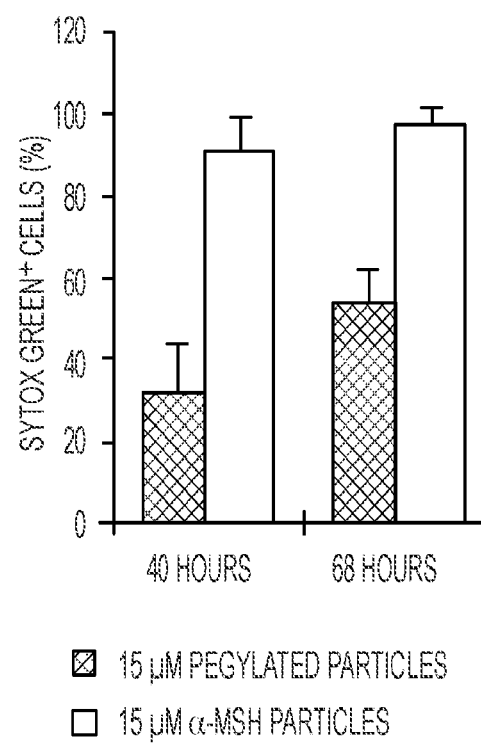

In certain embodiments, the nanoparticles described herein induce ferroptosis. Surface-modification of particles with αMSH peptides for targeting cancers enhances cellular internalization (data not shown). Particle surface modification with αMSH is not required for ferroptosis in the cell lines tested, as its induction has occurred, albeit at a slower rate, with PEG-coated C' dots unmodified with αMSH targeting ligands, which may reflect slower internalization of the base particles relative to α-MSH-modified platforms (FIG. 7F).

Figure 7G:
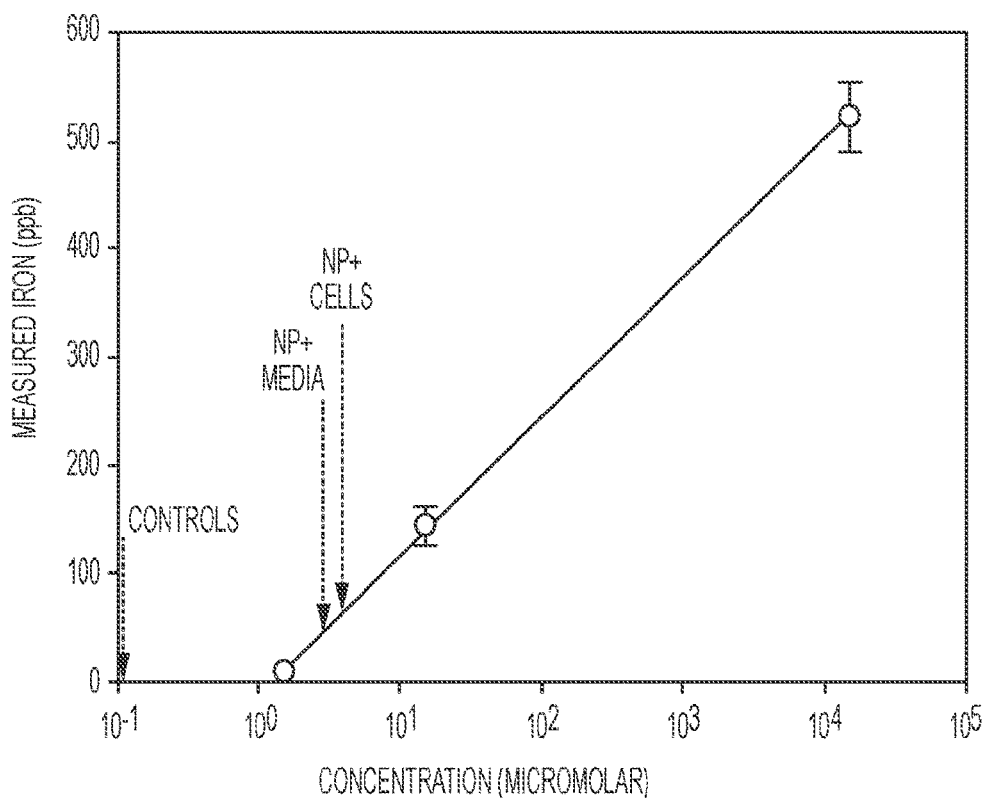
Figure 7H:
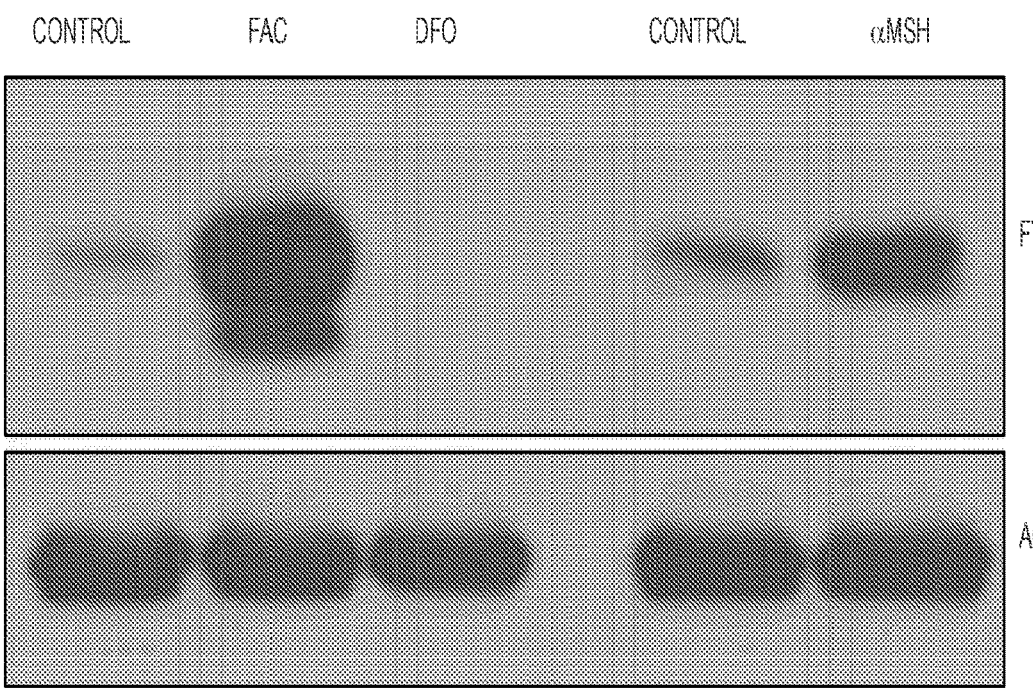
Figure 7I:
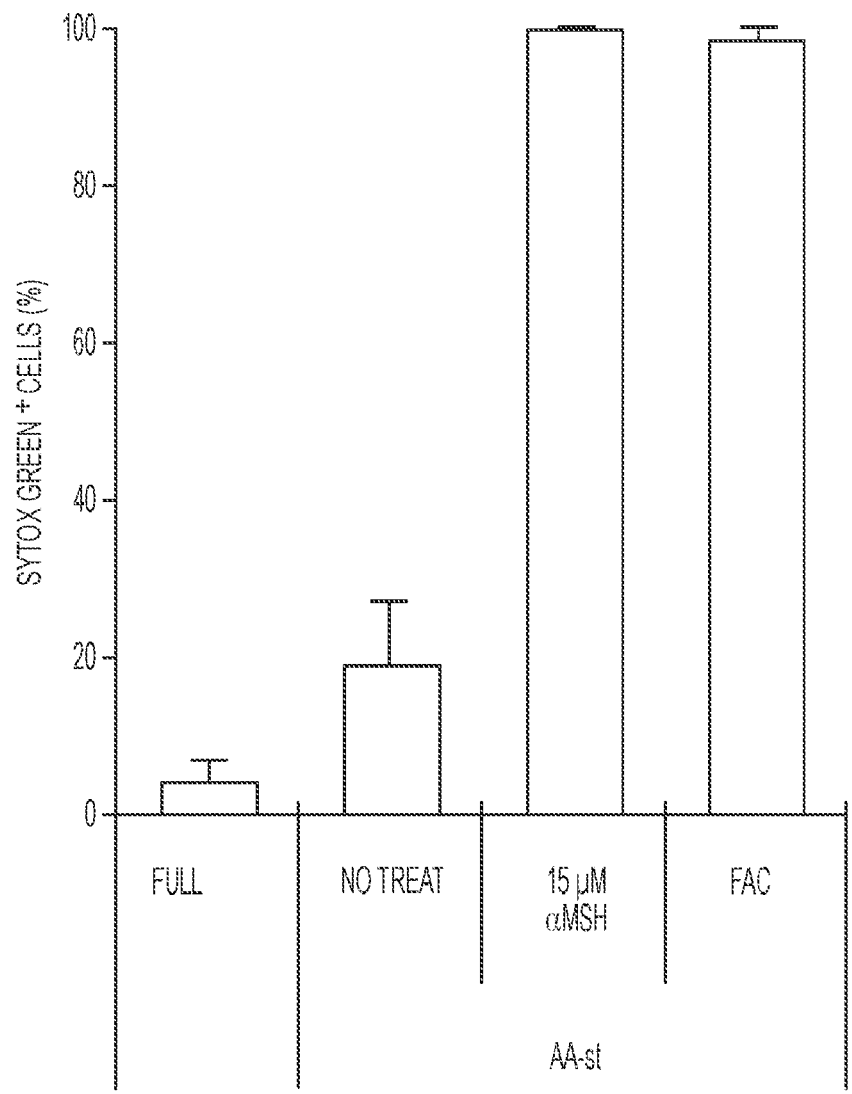
Figure 7J:
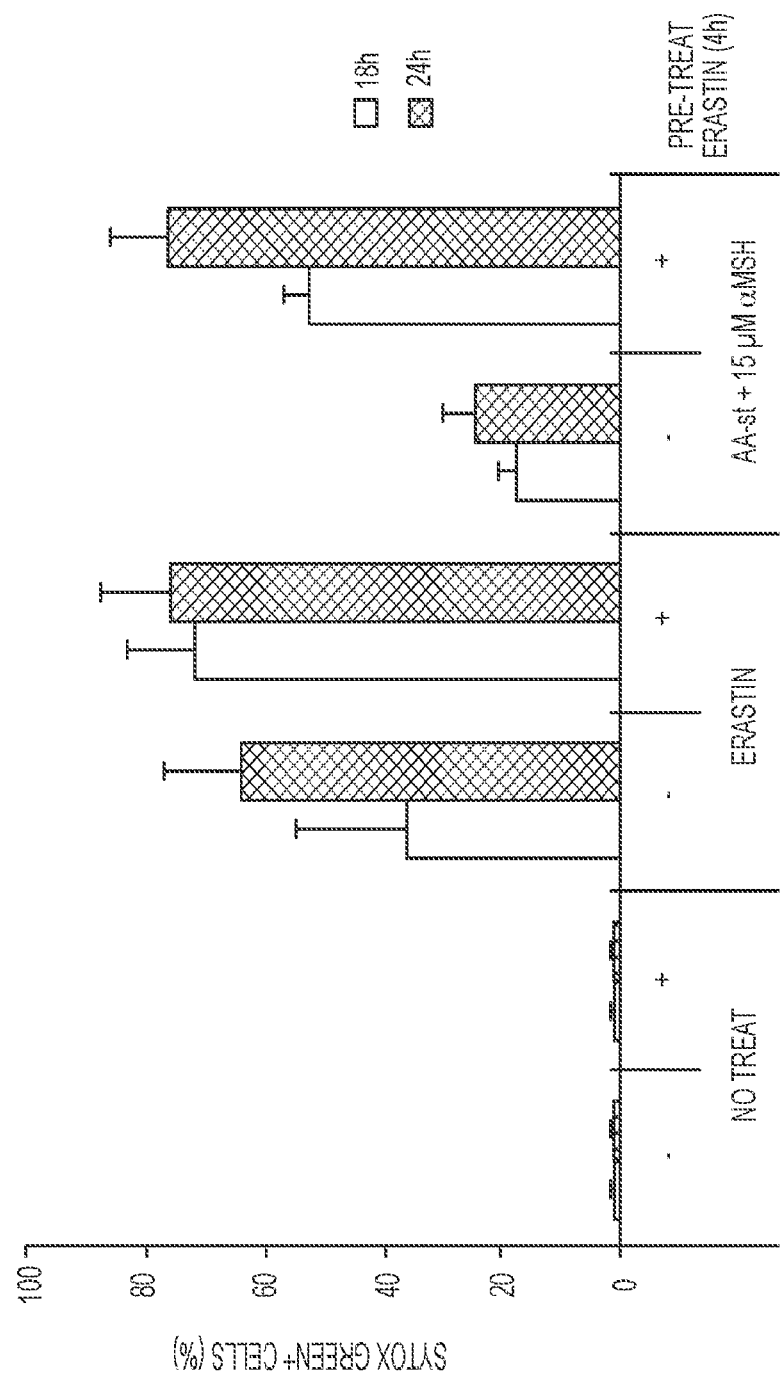

Therefore, in certain embodiments, the native silica particle itself has ferroptosis-inducing activity, as deprotonated surface silanol groups and/or fractal internal structure can lead to iron adsorption and/or incorporation within its structure. It was found that iron loading of α-MSH-PEG-C' dot nanoparticles incubated with culture media, as compared with doubly de-ionized water preparations (FIG. 7G, FIGS. 8A-8F). Increased iron loading occurred in a concentration-dependent manner when incubated with ferric oxide solutions, accompanied by a decrease in iron-loading capacity (FIGS. 8A-8F). Further, increased intracellular iron levels were found for α-MSH-PEG-C' dot nanoparticle-treated cells as compared to non-treated cells (FIG. 7G, Table 1). Also, particle-treated cells upregulate expression of the heavy chain of ferritin (FTH1) that binds cytosolic iron (FIG. 7H). It was also found that iron loading into cells by treatment with ferric ammonium citrate (FAC) is sufficient to mimic particle treatment and induce ferroptosis in amino acid-starved cells (FIG. 7I), suggesting that these silica-based nanoparticles may engage ferroptosis by loading iron into cells. Increased iron uptake can lead to the depletion of glutathione, conceivably due to increased ROS generation. It was found that glutathione levels are suppressed in particle-treated cells (FIGS. 7D-7E), and pre-treatment with erastin, which inhibits glutathione production by blocking cystine uptake, sensitizes cells to particle-induced ferroptosis, suggesting that glutathione depletion is rate-limiting for particle-induced death (FIG. 7J).

Table 1 shows iron concentrations measured by microwave plasma atomic emission spectroscopy (MP-AES).

TABLE 1

| Specimen | Iron-Containing Solution Concentrations (before purification) | Ψ Measured Iron Concentration (ppb) +/− S.D. (after purification) | Concentration of Iron in C' dots or Cells (μM) | Iron-loading Capacity |
|---|---|---|---|---|
| C' dots, diluted full media* | ~6.5 μM | 33.6 +/− 18.6 | 0.60 | 46.2% |
| C' dots, diluted AA-free media* | ~6.5 μM | 33.9 +/− 16.3 | 0.61 | 46.9% |
| C' dots, $Fe^{3+}$-doped solution | 1.5 μM | 8.32 +/− 12.9 | 0.15 | 50.0% |
| C' dots, $Fe^{3+}$-doped solution | 15.0 μM | 144.7 +/− 16.3 | 2.58 | 86.0% |
| C' dots, $Fe^{3+}$-doped solution | 1.5 mM | 522.6 +/− 32.6 | 9.33 | 3.1% |
| C' dots only | NA | BDL | BDL | NA |
| C' dot-exposed HT 1080 cells, AA-free media | ~8.6 μM | 37.6 +/− 7.8 | 0.67 | ~8.0% |
| HT1080 cells, AA-free media | ~8.6 μM | BDL | BDL | NA |

Figures 4A, 4B:
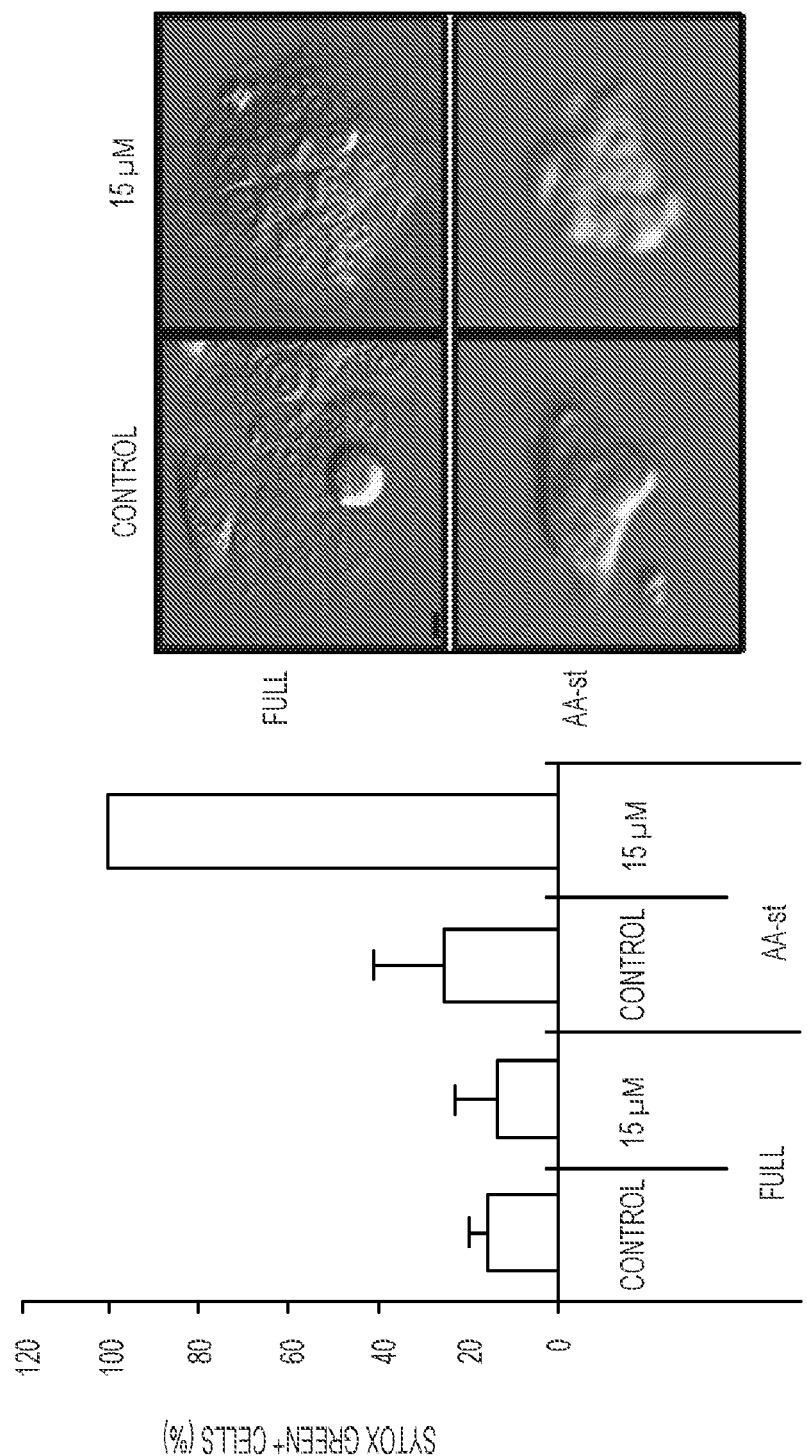
FIGS. 4A-4G show α-MSH-PEG-C' dots can induce cell death in different types of cancer cells.
Figures 4C, 4D:
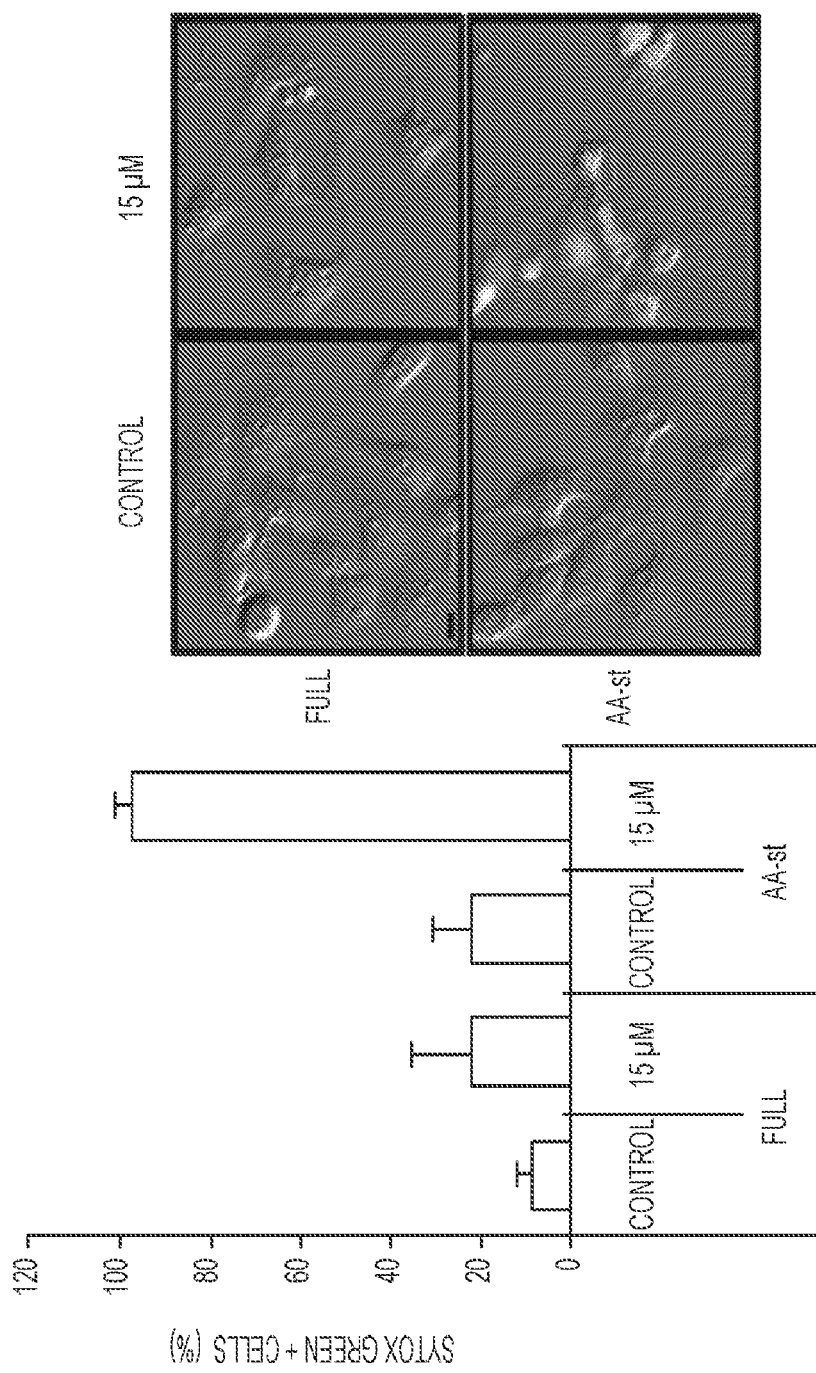
Figures 4E, 4F:
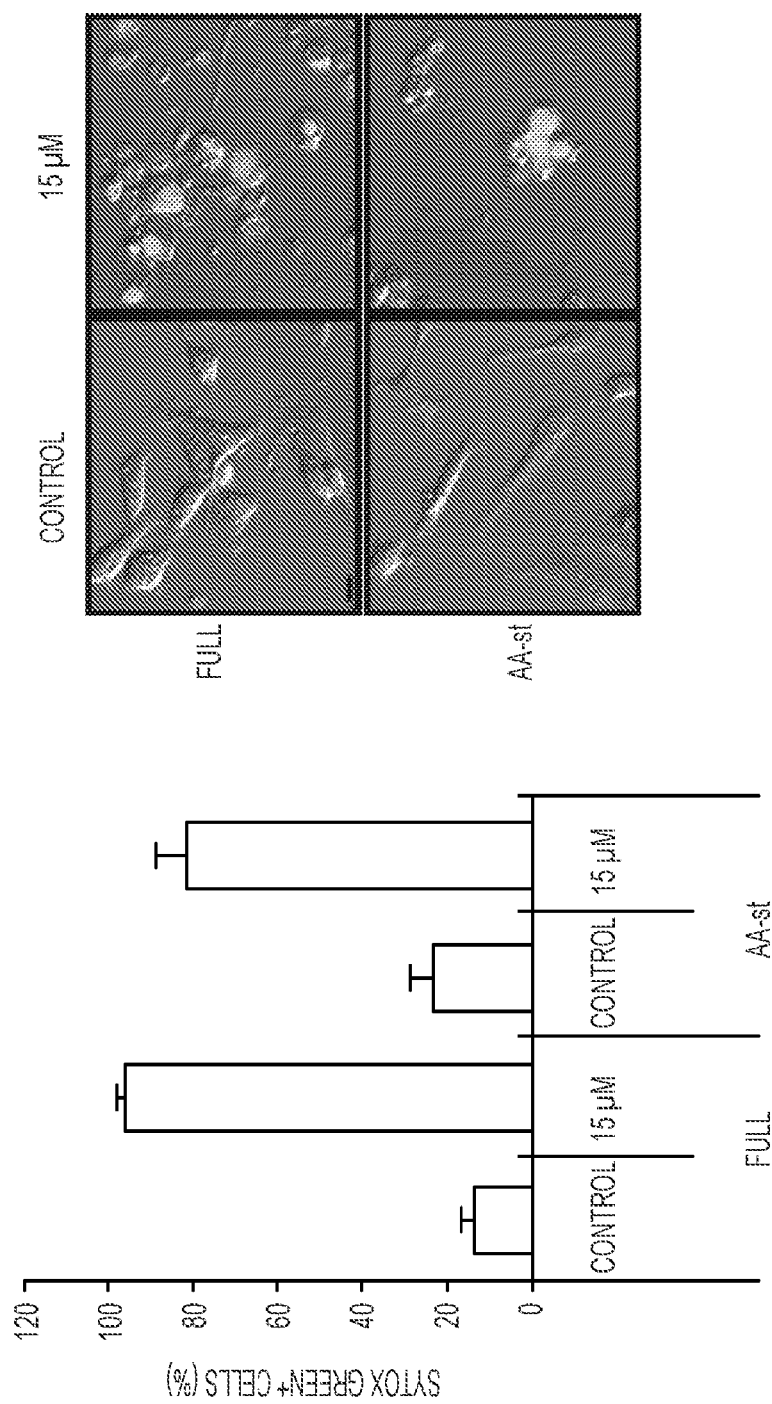
Figure 4G:
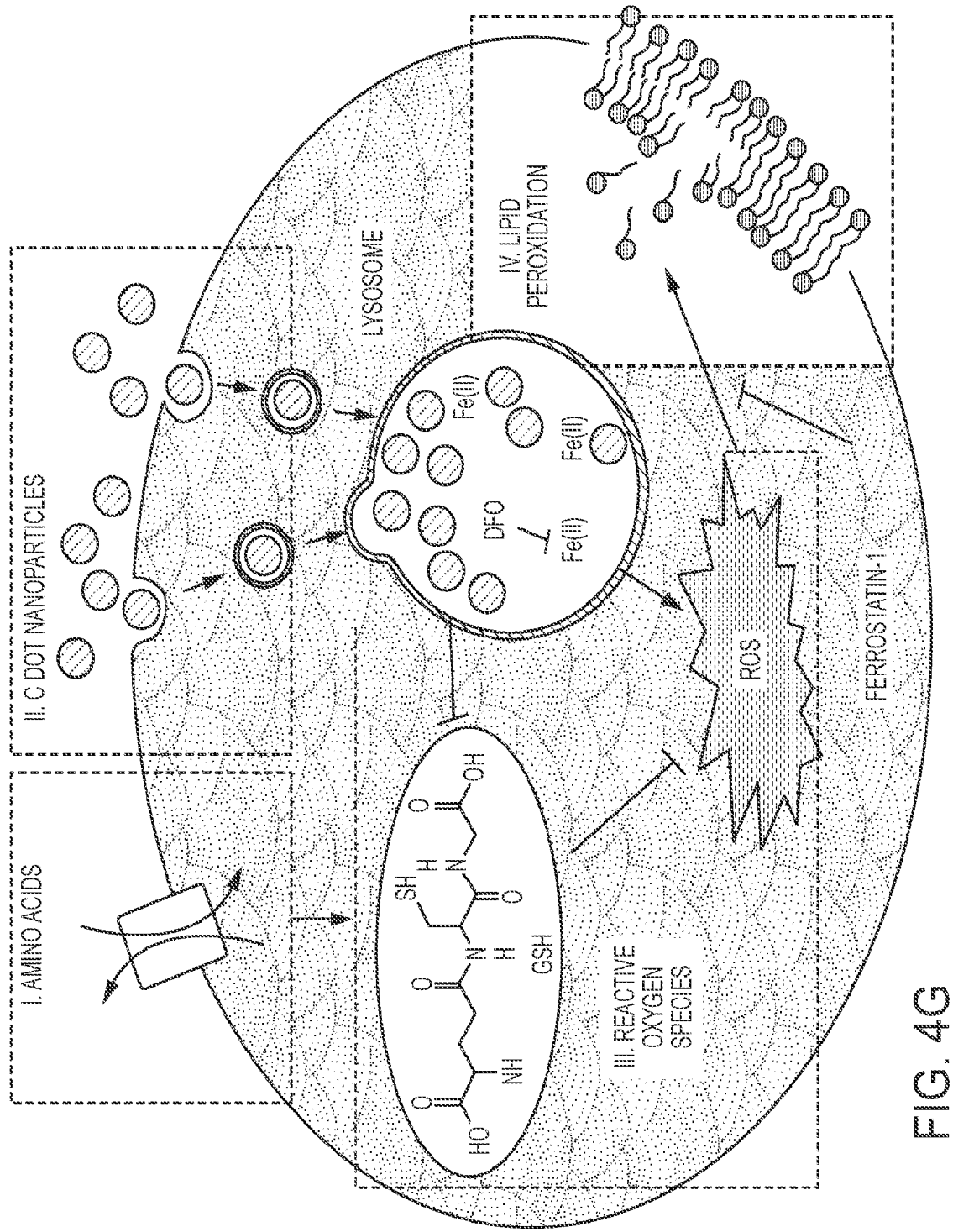
Figure 7K:
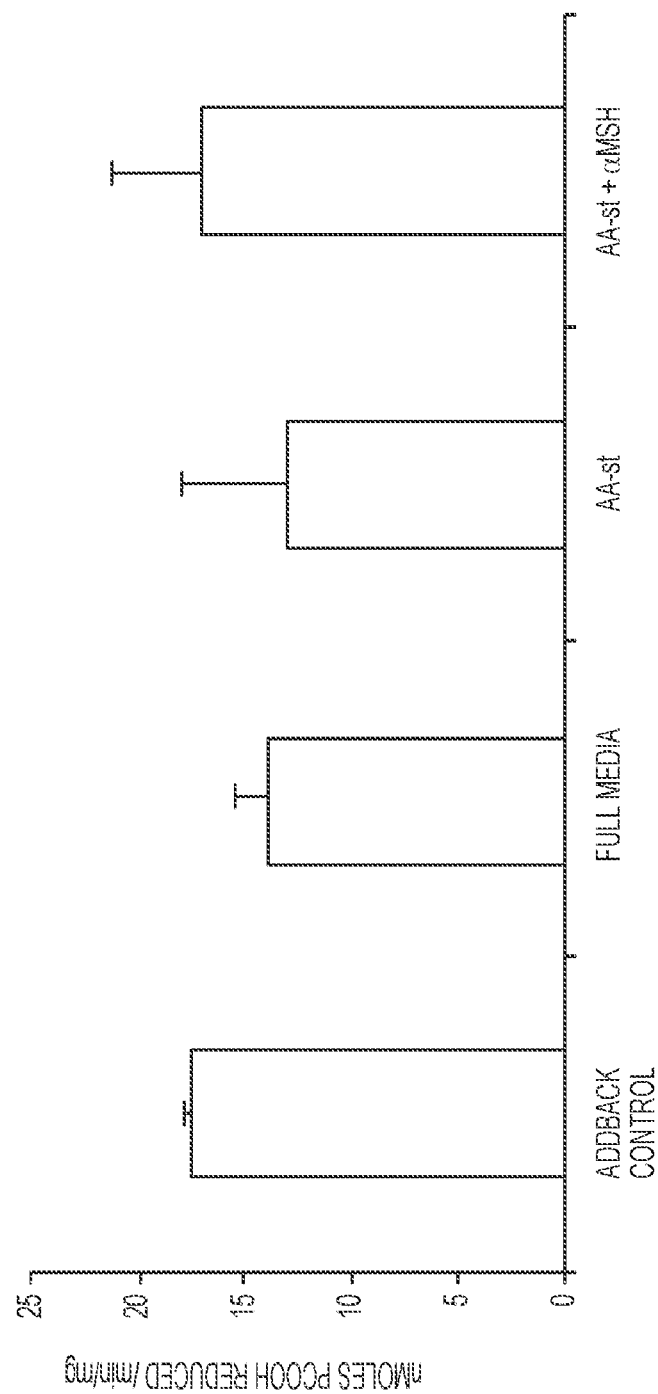

BDL, below detection limit;
NA not applicable
*iron present in undiluted full and AA-free media is 8.6 μM
Ψ re-suspended in water or phosphate buffer solution Taken together, the exemplary data described herein supports a model where ferroptosis induced by particle treatment involves iron uptake into cells leading to the suppression of glutathione and the accumulation of lipid ROS that execute ferroptosis (FIG. 4G). Lipid ROS can accumulate in glutathione-suppressed cells due to lowered activity of the glutathione peroxidase 4 (GPX4) enzyme that protects cells against lipid peroxidation and inhibits ferroptosis. It was not found that particle treatment inhibits GPX4 activity in an enzymatic assay from treated cell lysates (FIG. 7K). Likewise, it was not found that the model that particle treatment does not lead to lipid peroxidation by direct inhibition of GPX4.

Figure 6A:
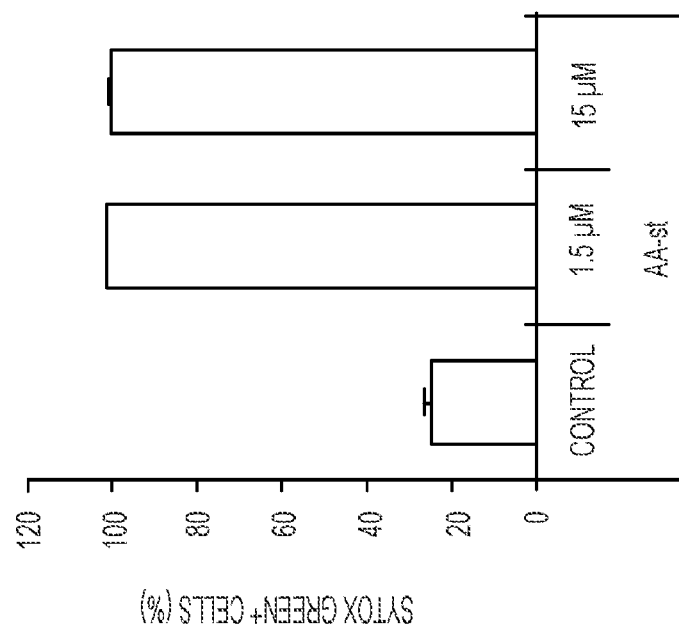
FIGS. 6A-6C show nanoparticle-induced cell death in 786-0 and HT-1080 cells, and vascularization of HT-1080 tumors. Quantification of cell death (Sytox green+) in (FIG. 6A) SKOV3 ovarian carcinoma cells after 50 hours and (FIG. 6B) HT1080 fibrosarcoma cells after 5 days. Cells were cultured in full media (Full) or amino acid-free media (AA-st) in the presence or absence of the indicated concentrations of α-MSH-PEG-C' dots. Bars indicate mean+/− standard deviation. N=5 per group.
Figure 6B:
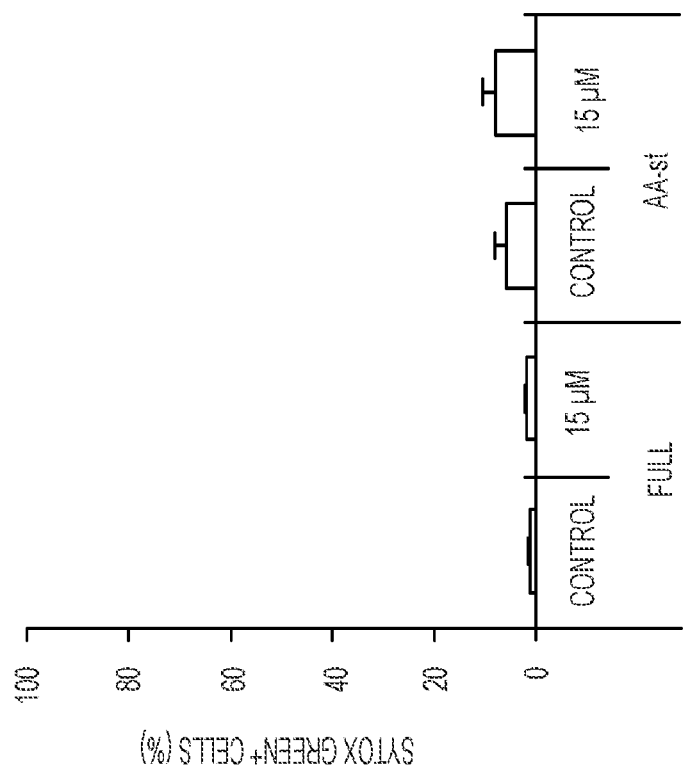
Figure 6D:
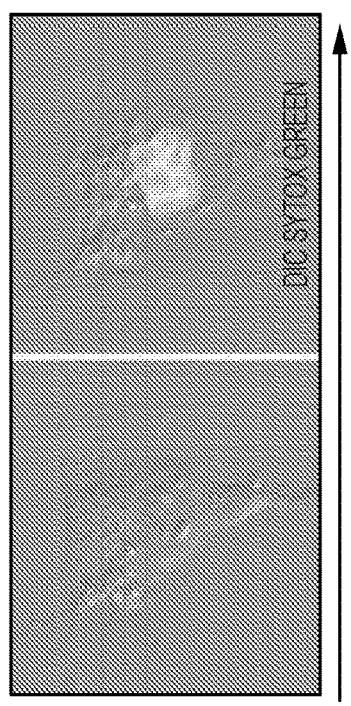
Figure 6E:
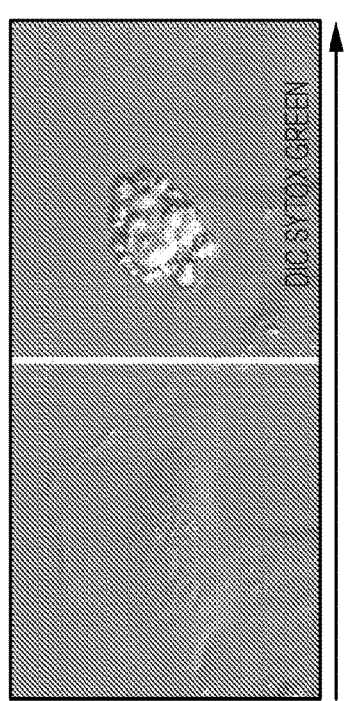
Figure 6C:
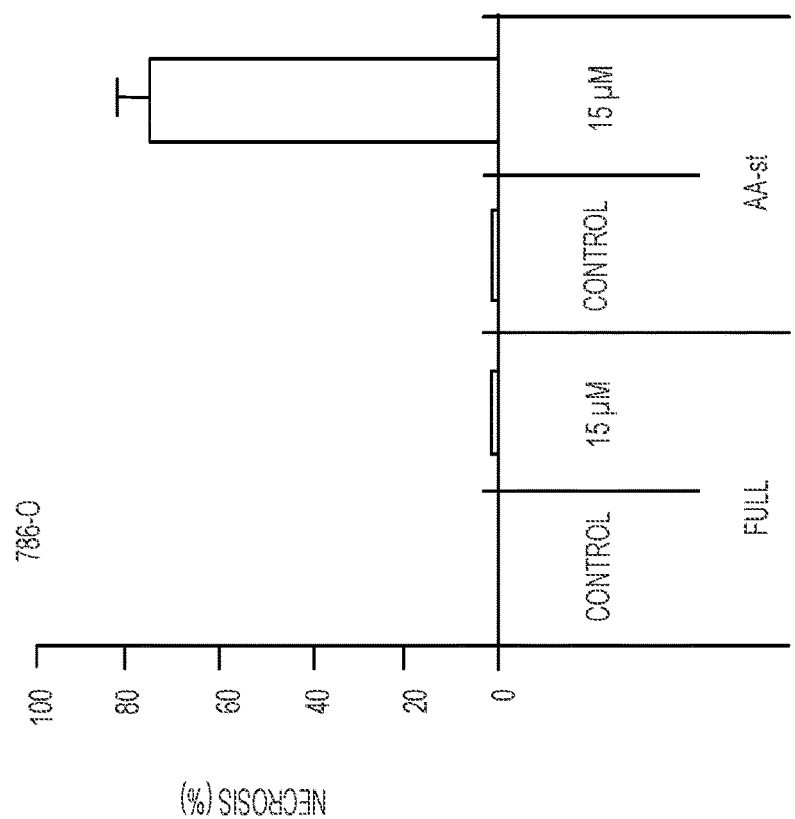

Some cancers (e.g., HT1080, 786-0) may also be particularly sensitive to this mechanism of cell death, which can lower the threshold of particle concentration needed to achieve an anti-tumor effect. It was found that HT-1080 cancer cells undergo α-MSH-PEG-C' dot-induced ferroptosis even under nutrient-replete conditions (FIGS. 4E-4F), and these cells are also killed in amino acid-deprived conditions with 10-fold lower nanoparticle concentration (FIG. 6B). HT-1080 tumors are well-vascularized (FIG. 9B), suggesting that the sensitivity of these cancer cells to particle-induced death, even under nutrient-replete conditions (FIGS. 4E-4F), may contribute to the strong anti-tumor effect that is observed following intravenous particle delivery.

While the concentration of nanoparticles used herein was selected to either induce in vitro cell death (e.g., 15 μM) or to inhibit in vivo tumor growth inhibition and regression (e.g., 60 μM) and is at least four orders of magnitude higher than what is used currently in human subjects for single-dose imaging-based analyses, local concentrations can be driven to much higher levels at tumor sites as part of a multi-dosing strategy, combinational treatment regimen, and/or by direct catheter infusion at the target site. Such a dosing schedule can be designed to yield maximum tumor-to-to-background ratios while reducing off-target toxicities and promoting efficient renal clearance. Notably, the leakiness of tumor vasculature may allow the accumulation of systemically injected nanoparticles in tumor tissues and also contributes to nutrient deprivation within tumors. Without having to be bound by theory, this further suggested that the synergism of nanoparticles and nutrient deprivation may be restricted to tumor sites in vivo. It was also found that different tumor cell lines apparently can differ in their sensitivity to the ferroptosis-inducing mechanism. For example, it was found that an ovarian cancer cell line, SKOV3, showed resistance to cell death by combined treatment of amino acid deprivation and α-MSH-PEG-C' dots (FIG. 6A). In contrast, HT1080 fibrosarcoma cells underwent α-MSH-PEG-C' dot nanoparticle-induced ferroptosis even under nutrient-replete conditions (FIGS. 4E-4F) and in amino acid-deprived conditions with 10-fold lower nanoparticle concentration (1.5 μM) (FIG. 6B). Targeted particle uptake into HT1080 cells, in this instance, presumably occurred via a non-specific endocytic route. As ferroptosis is an iron-dependent cell death, without having to be bound by theory, different susceptibilities may be due in part to the amount of iron that is available in cells. For example, iron is an essential component for cellular homeostasis but can also generate ROS that can damage organelles. Cells can regulate iron availability by uptake, export, or a shift from storage to the labile iron pool (LIP) and some of these processes are altered in cancer. The oncogenes c-myc and E1a reduce levels of ferritin, the main cytosolic iron storage protein, which can shift iron from storage to the metabolically active LIP, and repression of ferritin can stimulate Ras-dependent proliferation by activating DNA synthesis. Ferroptosis-inducing drugs were initially discovered in a screen of small molecules that confer selective killing of Ras-driven tumor cells. Moreover, among the tested cancer cell lines above, HT1080 is the only cell line harboring a Ras mutation. Therefore, it will be determined if cancer cells with mutant Ras are generally more sensitive to nanoparticle treatment.

Some nanomaterials (e.g., uncoated silica particles with diameters on the order of 63 nm (e.g., an order of magnitude larger than C' dots)) have been shown to induce ROS in cells. In contrast, increased levels of either cytosolic or lipid ROS in cells treated for 24 hours with sub 10-nm diameter α-MSH-PEG-C' dots were not detected (FIGS. 7A-7C). As described above, it was found that amino acid starvation and nanoparticle treatment both lower glutathione levels in cells, and also have an additive effect (FIGS. 7D-7E). Without having to be bound by theory, this data suggested that cell death in this context may be triggered at least in part by glutathione depletion similar to the ferroptosis-inducing agent erastin that inhibits glutathione production by limiting cysteine uptake.

Figure 9A:
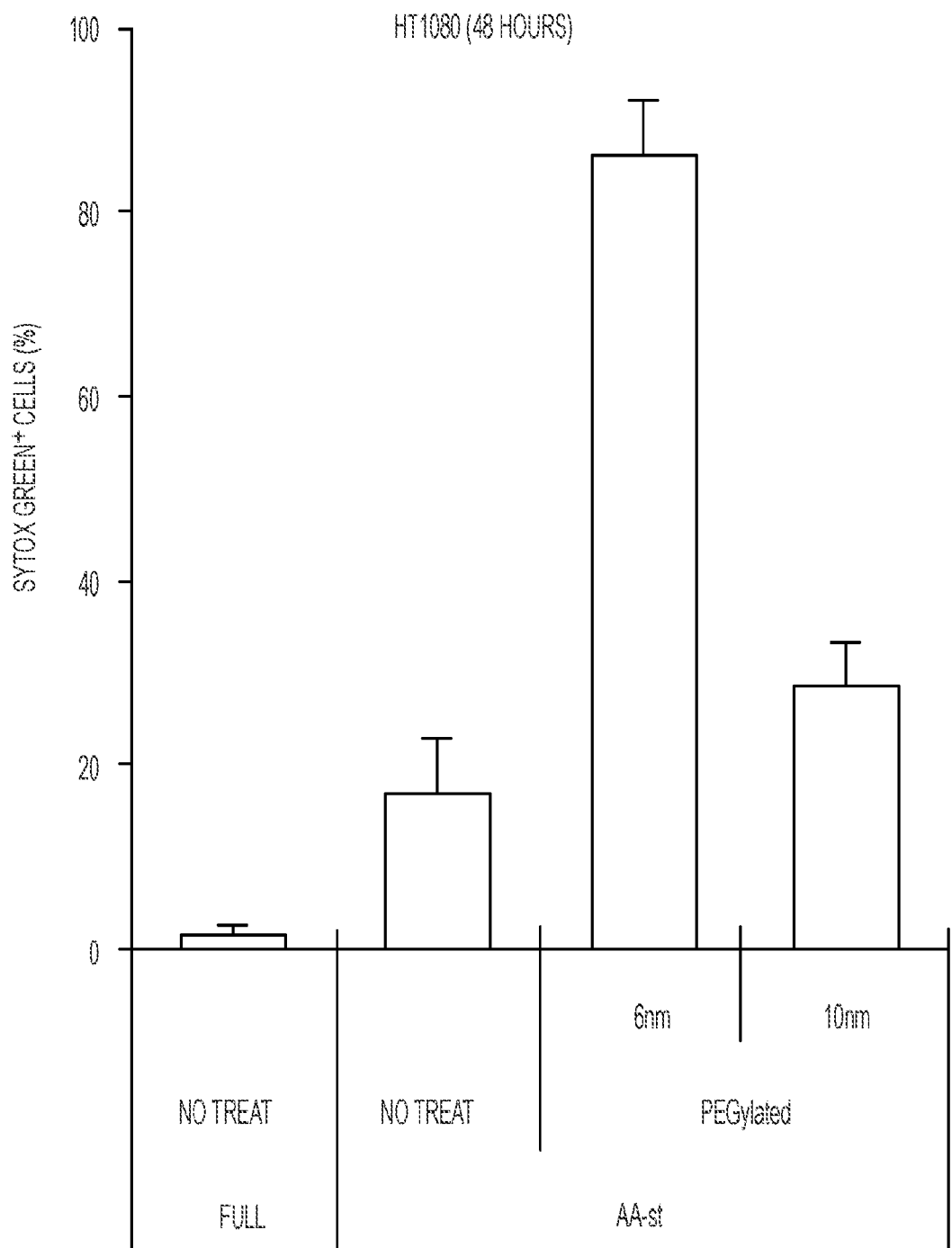
FIGS. 9A-9C show images of particle-treated tumors.
Figure 9B:
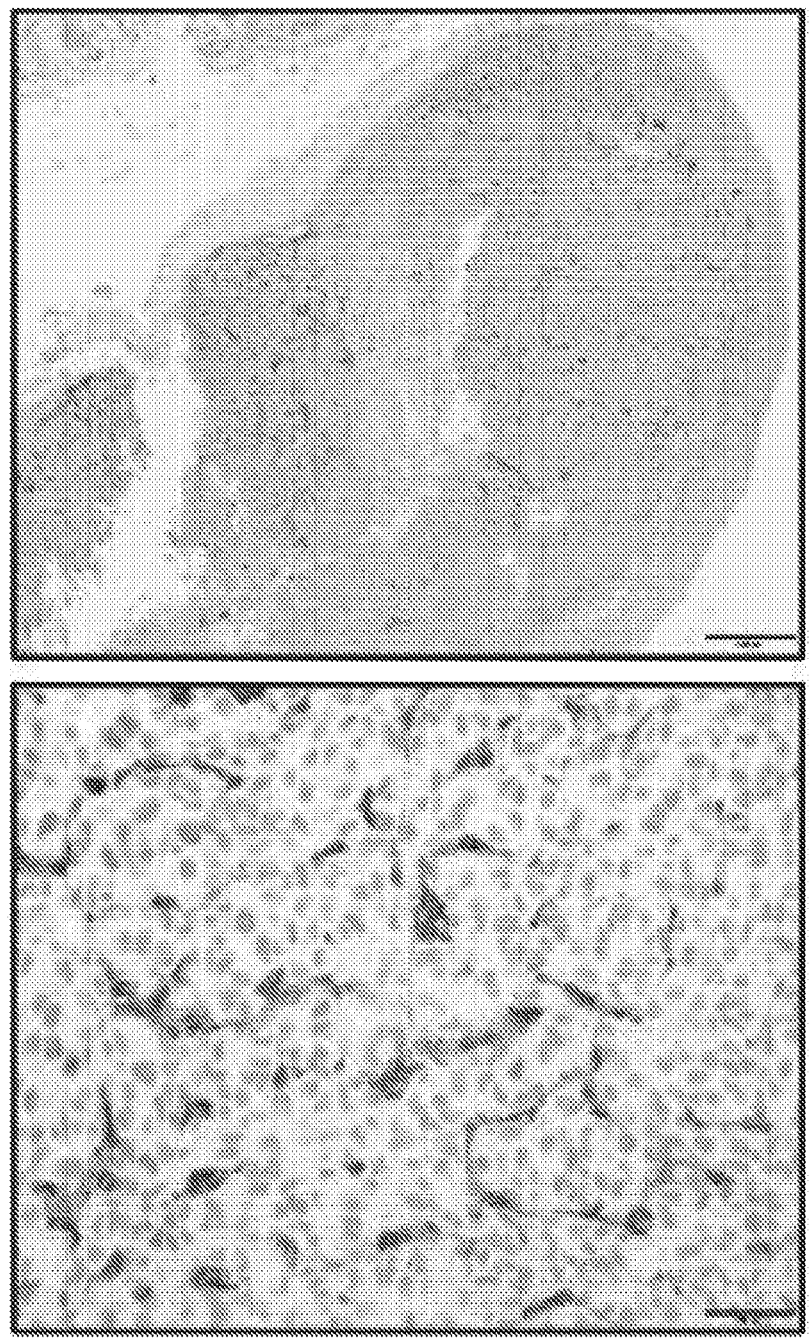
Figure 9C:
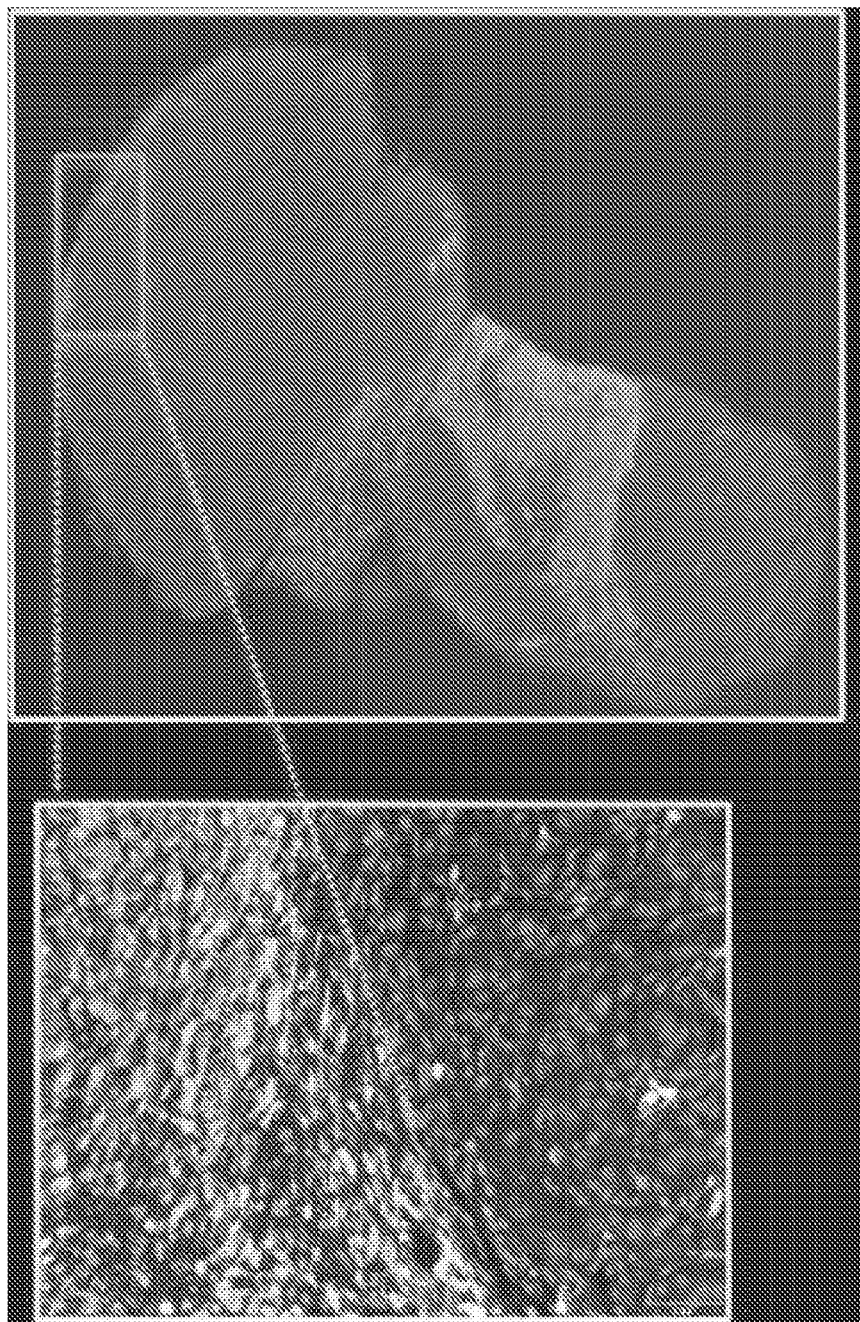
Figure 10A:
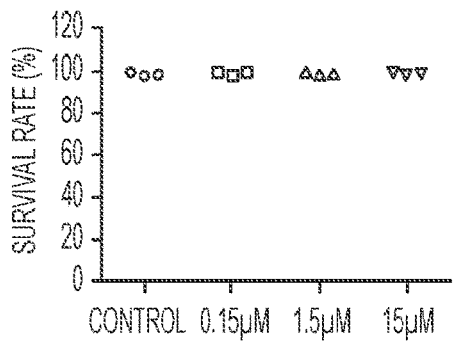
FIGS. 10A-10J show individual data points for graphs from FIGS. 1C-1F and FIGS. 2A-2E.
Figure 10B:
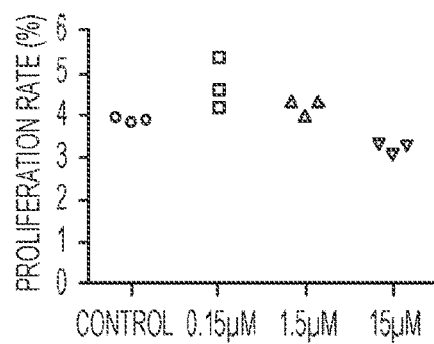
Figure 10C:
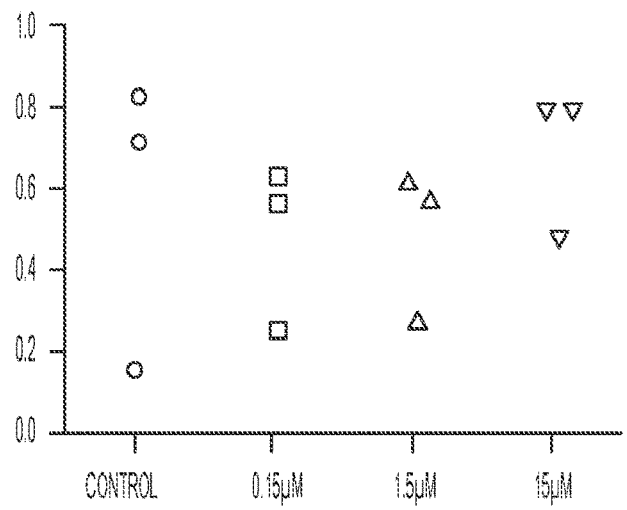
Figure 10D:
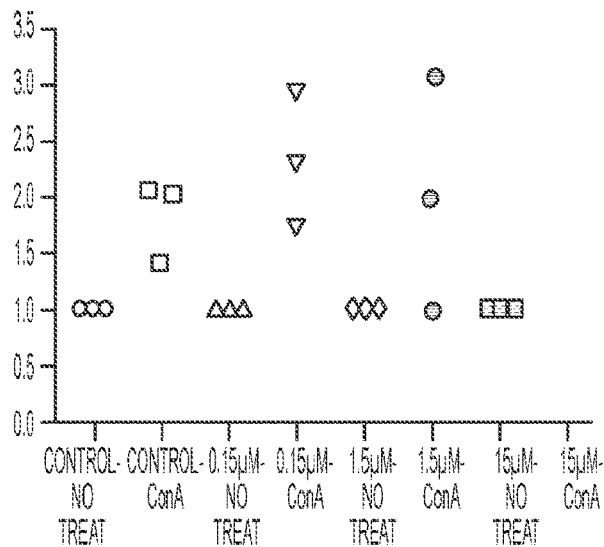
Figure 10E:
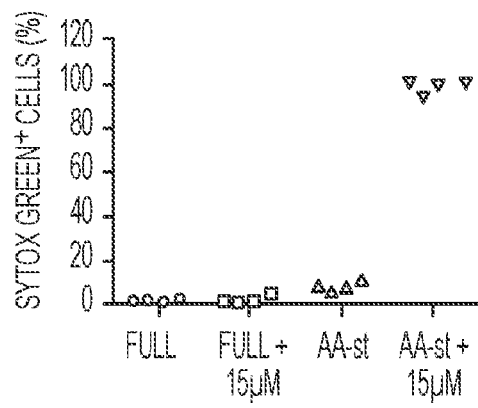
Figure 10F:
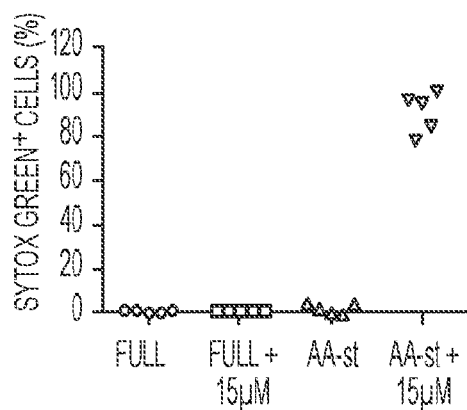
Figure 10G:
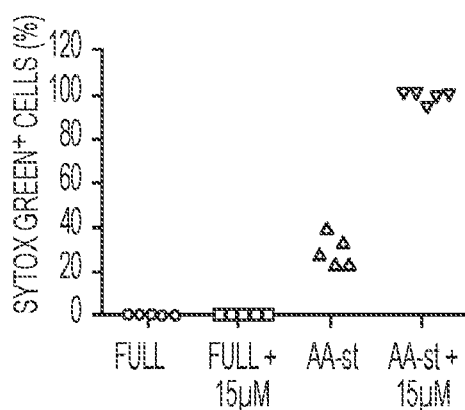
Figure 10H:
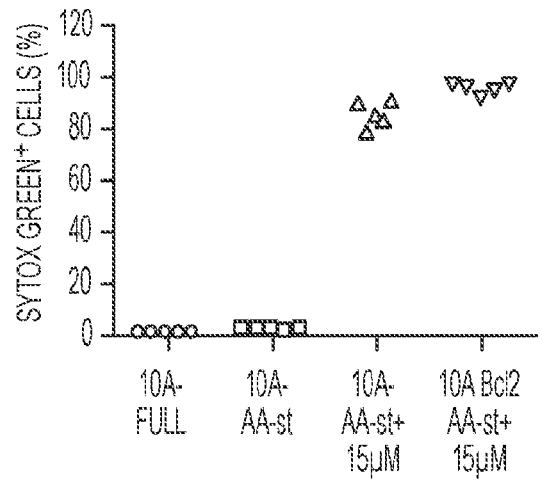
Figure 10I:
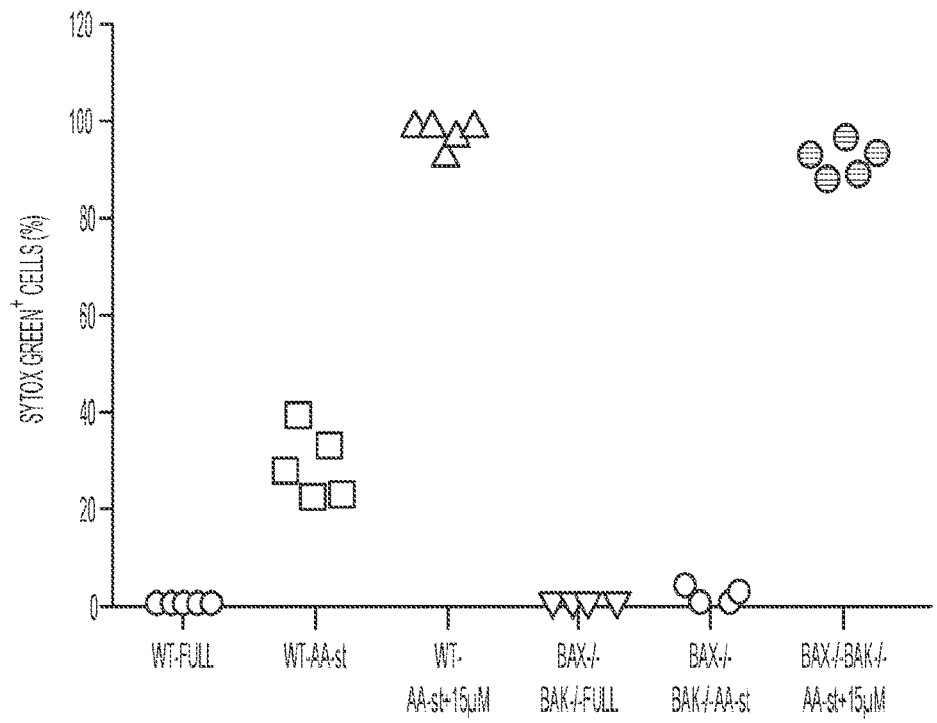
Figure 10J:
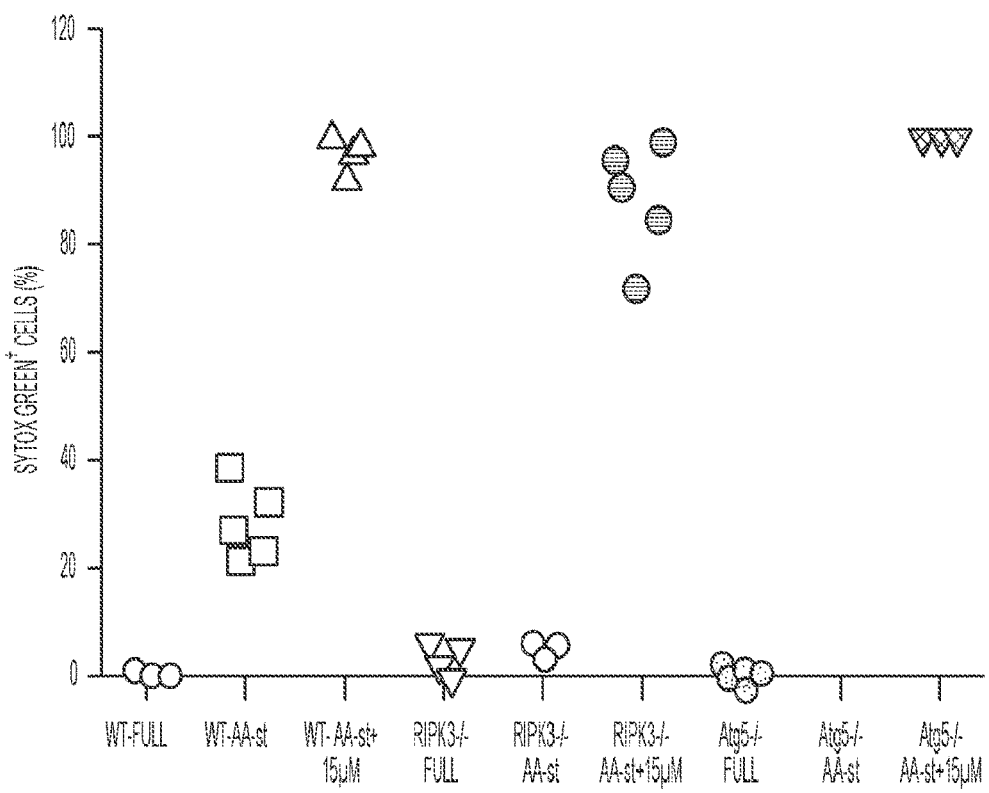
Figure 11A:
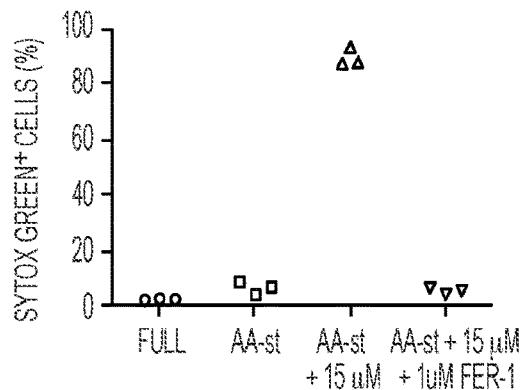
FIGS. 11A-11I show individual data points for graphs from FIGS. 3A-3F, 4A-4C and 8A-8G.
Figure 11D:
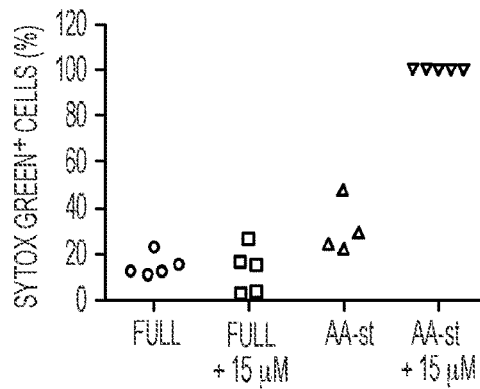
Figure 11B:
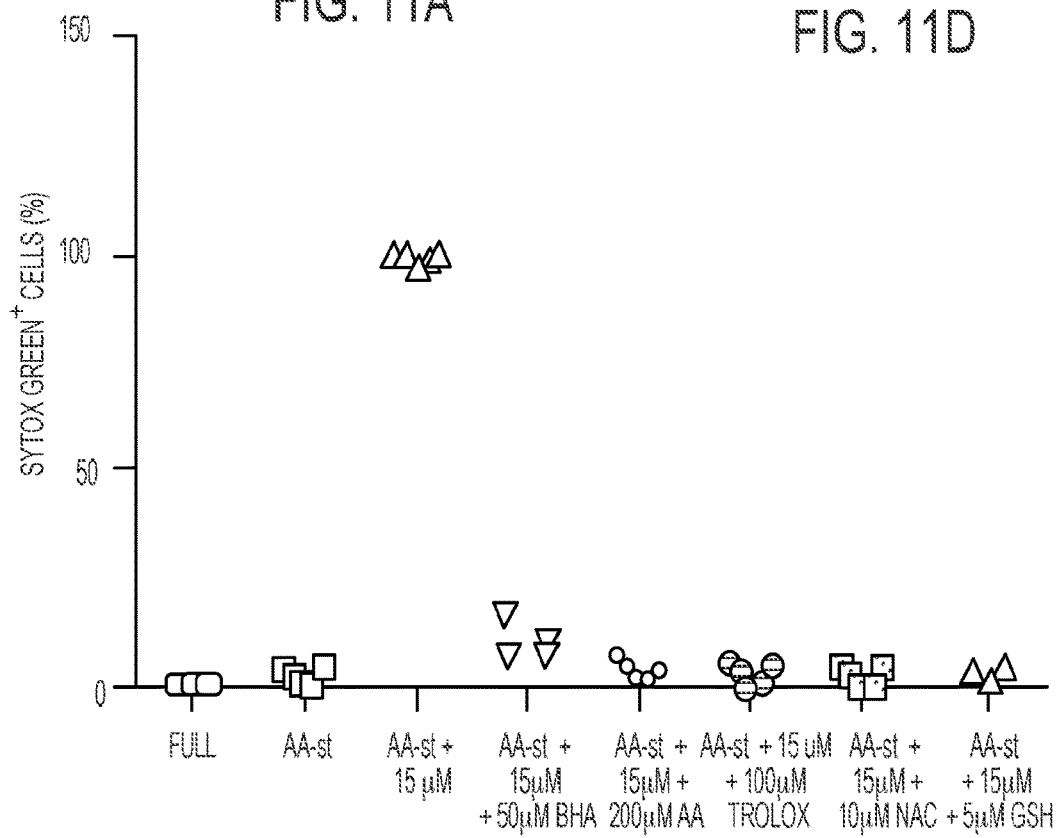
Figure 11C:
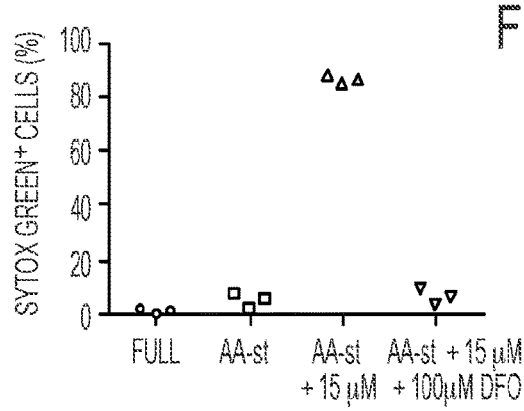
Figure 11E:
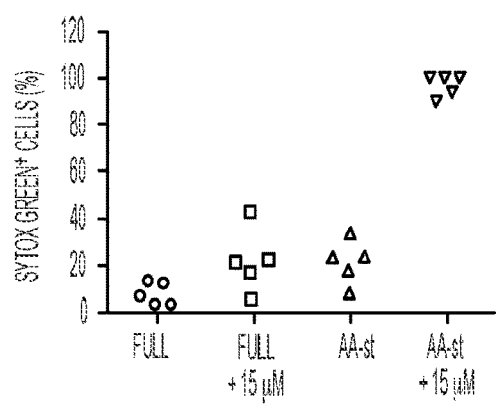
Figure 11F:
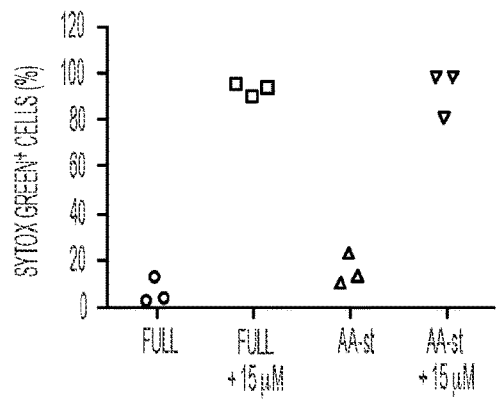
Figure 11G:
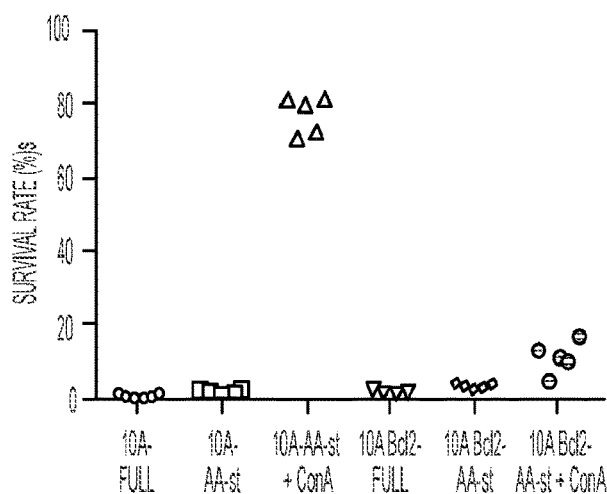
Figure 11I:
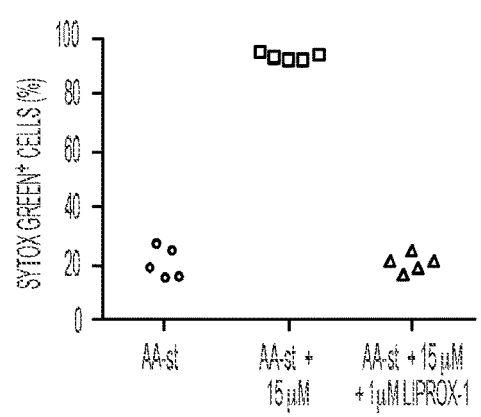
Figure 11H:
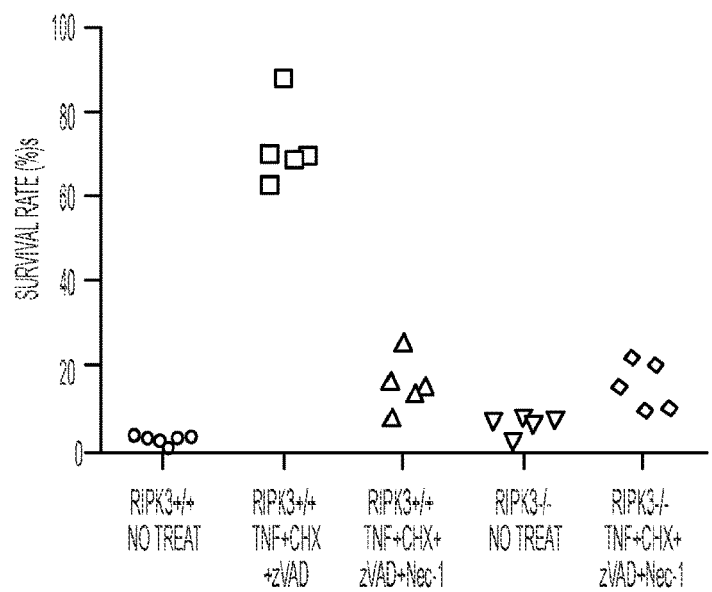
Figure 12A:
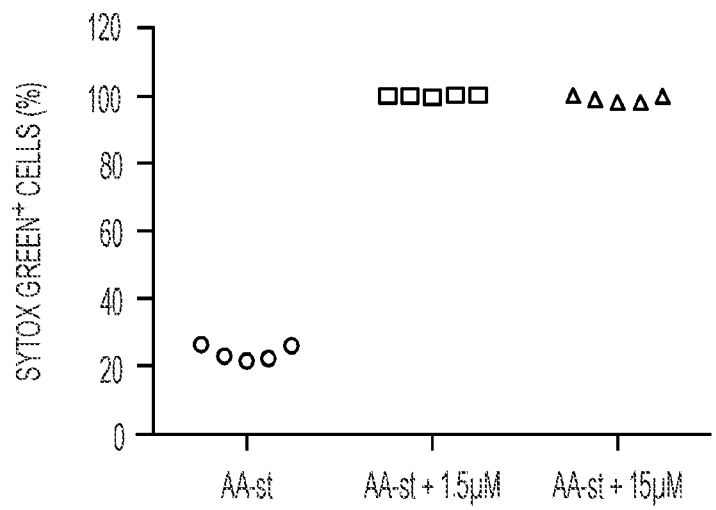
FIGS. 12A-12E show individual data points for graphs from FIGS. 6B-6C and 7B-7H.
Figure 12B:
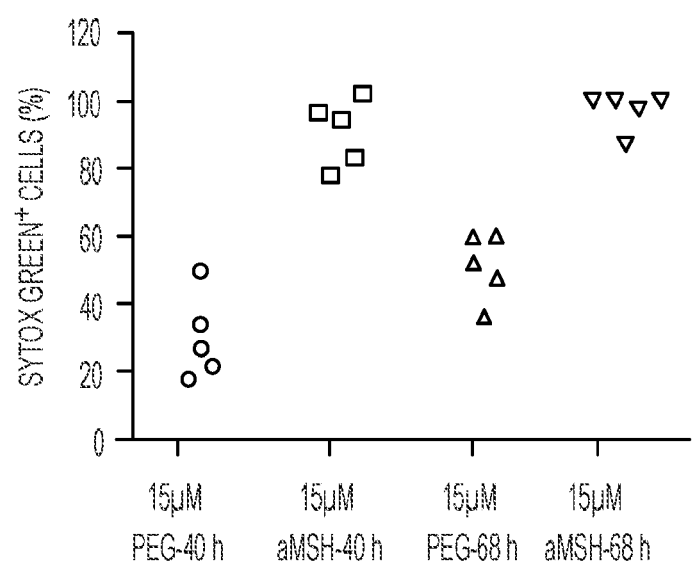
Figure 12C:
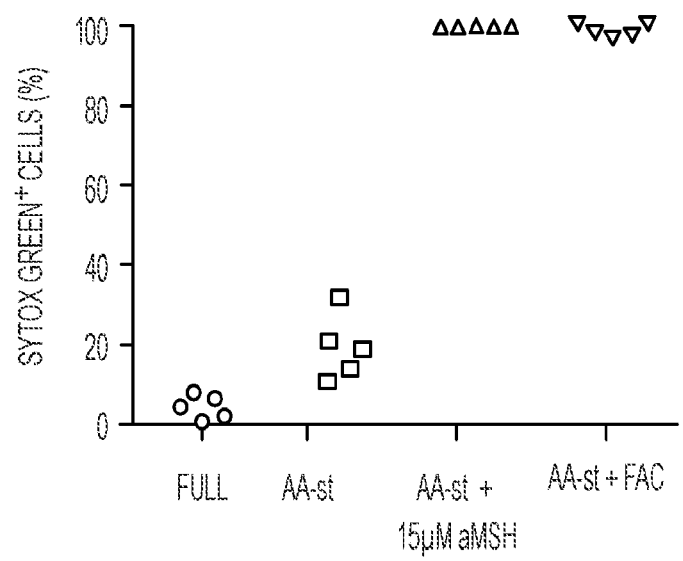
Figure 12D:
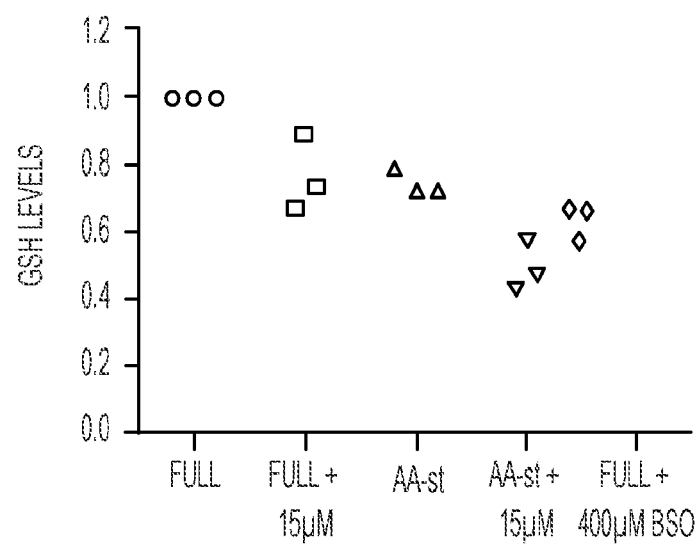
Figure 12E:
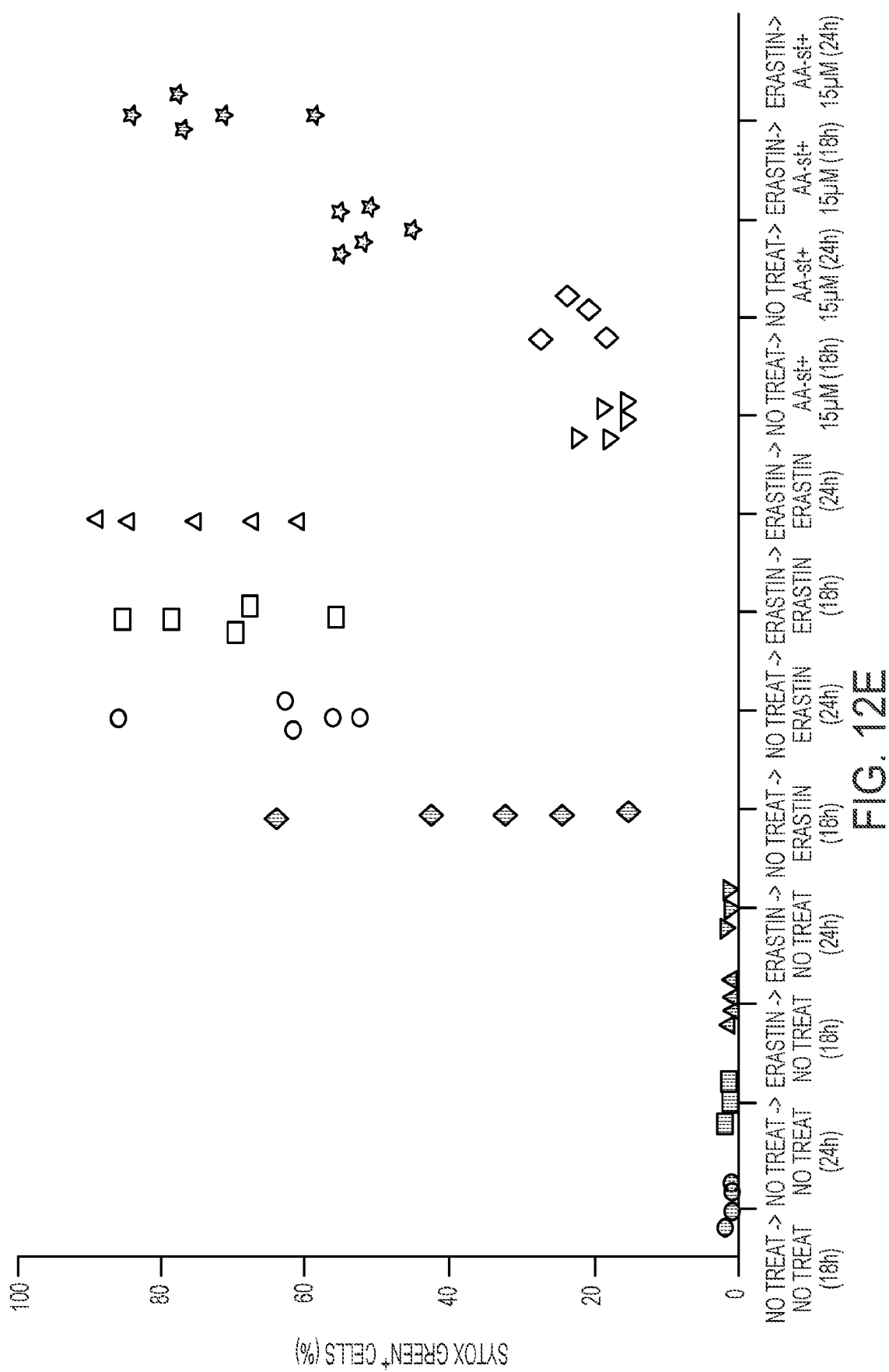

The nanoparticles used herein were surface-modified with αMSH peptides for targeting cancers in vivo. This modification also was shown to enhance cellular uptake (data not shown). This particle surface modification does not appear to be involved in ferroptosis because ferroptosis induction has also been observed with PEG-coated C' dots that are not modified with αMSH targeting ligands. However, death caused by PEG-coated C' dots without the αMSH modification occurred with slower kinetics within cell populations due to decreased rates of uptake of the base particles compared to those that are α-MSH-modified platforms in MC1-R expressing melanoma cells (FIG. 7F). On the other hand, particle size was found to play a critical role in the induction of ferroptosis under amino acid deprived conditions. Relative to the high percentage of Sytox Green labeled HT1080 cells (e.g., 80%) found 48 hours after exposure to smaller diameter (~6 nm) PEGylated C' dots, the percentage of labeled cells found after incubation with larger diameter (~10 nm) particles was much lower, on the order of 25%, only slightly increased over non-treated cells (FIGS. 9A-9C).

While conceivably the sensitivity of some cancers could lower the particle concentrations needed to exert an anti-tumor effect, it was also found that multiple high dose treatments are well tolerated. Evaluation of tumor, hepatic, renal, and hematologic specimens from particle- and vehicle-treated HT-1080- and 786-O-bearing mice was performed at the termination of the experimental examples. No significant group differences were found in complete blood counts, serum chemistries, and hepatic and renal histopathology, except for indirect and total bilirubin serum concentrations which were moderately elevated in particle-treated mice, as compared to control animals (Table 2, Table 3). However, no mechanism could be ascribed to this finding given the lack of hemolysis on complete blood counts and absence of liver injury on histopathology and serum chemistries. These findings therefore suggest that multiple high-dose α-MSH-PEG-C' dot treatments are well tolerated. The extent of macrophage staining among particle-treated (marked) and vehicle-treated (mild) tumor specimens is also summarized (Table 4).

Table 2 shows metabolic concentration profiles, renal profiles, and hepatic function profiles in tumor-bearing mice.

TABLE 2

| | | HT1080 Particle-Exposed Female | | | | HT1080 Saline Vehicle Male Female | | | | | 786-O Particle-Exposed Female | | | | 786-O Saline Vehicle Male | |
|---|---|---|---|---|---|---|---|---|---|---|---|---|---|---|---|---|
| Metabolic profile | Na (mEq/L) | 151 | 149 | 153 | 156 | 156 | 152 | 152 | 156 | 152 | 157 | 157 | 154 | 155 | QNS | QNS |
| | K (mEq/L) | 8.1 | 9.2 | 8.2 | 9.6 | 9.3 | 10.7 | 9.1 | 8.2 | 8.5 | 8.5 | 8.8 | 10.1 | 8.8 | ONS | ONS |
| | Cl (mEq/L) | 111 | 111 | 111 | 108 | 109 | 109 | 117 | 113 | 112 | 114 | 115 | 113 | 110 | ONS | ONS |
| | TCO$_2$ (mEq/L) | 26 | 24 | 26 | 13 | 23 | 21 | 18 | 23 | 23 | 14 | 11 | 10 | 18 | ONS | 15 |
| | Ca (mg/dL) | 10.5 | 10.2 | 10.2 | 10.3 | 10.3 | 9.7 | 10.5 | 10.4 | 10.3 | 9.7 | 10.0 | 10.4 | 10.1 | 6.4 | 9.2 |
| | P (mg/dL) | 9.2 | 9.0 | 8.6 | 9.1 | 10.0 | 9.1 | 9.5 | 8.6 | 7.6 | 9.4 | 9.0 | 10.8 | 9.9 | 8.5 | 10.0 |
| | GLU (mg/dL) | 179 | 184 | 192 | 108 | 153 | 149 | 216 | 164 | 215 | 142 | 208 | 224 | 210 | 149 | 160 |
| Renal | BUN (mg/dL) | 12 | 18 | 19 | 29 | 28 | 30 | 19 | 21 | 23 | 16 | 17 | 16 | 24 | 19 | 21 |
| | Crea (mg/dL) | 0.2 | 0.2 | 0.24 | 0.12 | 0.12 | 0.03 | 0.20 | 0.23 | 0.21 | 0.10 | 0.11 | 0.13 | 0.18 | ONS | ONS |
| Heptatic Function | ALP (U/L) | 29 | 37 | 58 | 67 | 71 | 45 | 73 | 56 | 48 | 106 | 95 | 120 | 71 | 60 | 55 |
| | AST (U/L) | 140 | 293 | 120 | 113 | 67 | 119 | 365 | 149 | 209 | 188 | 156 | 1100 | 68 | 214 | 43 |
| | ALT (U/L) | 15 | 94 | 30 | 24 | 18 | 25 | 158 | 57 | 71 | 87 | 66 | 509 | 34 | 144 | 21 |
| | GGT (U/L) | 0 | 0 | 0 | 0 | 0 | 0 | 0 | 0 | 0 | 0 | 0 | 0 | 0 | 0 | 0 |
| | TBIL (mg/dL) | 0.8* | 0.8* | 0.9* | 0.2 | 0.3 | 0.4 | 0.3 | 0.2 | 0.3 | 0.8* | 0.7* | 0.9* | 0.2 | 0.2 | 0.1 |
| | DBIL (mg/dL) | 0.1 | 0.1 | 0.1 | 0.0 | 0.0 | 0.0 | 0.0 | 0.0 | 0.1 | 0.1 | 0.1 | 0.1 | 0.1 | 0.0 | 0.0 |
| | IBIL (mg/dL) | 0.7* | 0.7* | 0.8* | 0.2 | 0.3 | 0.4 | 0.3 | 0.2 | 0.2 | 0.7* | 0.6* | 0.8* | 0.1 | 0.2 | 0.1 |
| | TP (g/L) | 4.9 | 4.9 | 5.1 | 5.3 | 5.2 | 5.3 | 5.3 | 5.3 | 5.3 | 4.9 | 5.1 | 5.4 | 5.0 | 5.6 | 5.3 |
| | ALB (g/L) | 3.8 | 3.9 | 3.9 | 3.3 | 3.1 | 3.1 | 3.3 | 3.2 | 3.2 | 3.1 | 3.2 | 3.3 | 2.9 | 3.3 | 3.0 |
| | GLOB (g/dL) | 1.9 | 2.0 | 2.0 | 2.0 | 2.1 | 2.2 | 2.0 | 2.1 | 2.1 | 1.8 | 1.9 | 2.1 | 2.1 | 2.3 | 2.3 |

TABLE 2-continued

|  | HT1080 Particle-Exposed Female | | | | HT1080 Saline Vehicle Male Female | | | | 786-O Particle-Exposed Female | | | | 786-O Saline Vehicle Male | | |
|---|---|---|---|---|---|---|---|---|---|---|---|---|---|---|---|
| CHOL (mg/dL) | 86 | 83 | 88 | 82 | 98 | 104 | 99 | 108 | 118 | 72 | 71 | 88 | 99 | 67 | 90 |
| TRIG (mg/dL) | 94 | 74 | 96 | 89 | 159 | 127 | 84 | 88 | 85 | 95 | 94 | 94 | 89 | 151 | 92 |
| CK (U/L) | 442 | 506 | 325 | 50 | 122 | 255 | 616 | 300 | 358 | 63 | 117 | 458 | 100 | 53 | 36 |

Na, sodium;
K, potassium;
Cl, chloride;
TC0₂, total carbon dioxide;
Ca, calcium;
P, phosphorus;
GLU, glucose;
BUN, blood urea nitrogen;
Crea, creatinine;
ALP, alkaline phosphatase;
AST, aspartate aminotransferase;
ALT, alanine aminotransferase;
GGT, gamma-glutamyl transferase;
TBIL, total bilirubin;
DBIL, direct bilirubin;
IBIL, indirect bilirubin;
TP, total protein;
ALB, albumin;
GLOB, globulin;
CHM, cholesterol;
TRIG, triglyceride;
CK, creatine kinase;
*, elevated relative to normal values Table 3 shows hematologic profiles in tumor-bearing mice

TABLE 3

|  | 786-0 Particle-Exposed Female | | | | 786-0 Saline Vehicle Male | |
|---|---|---|---|---|---|---|
| RBC (M/μL) | 9.87 | 9.79 | 10.50 | 9.53 | 9.30 | 9.13 |
| HGB (g/dL) | 15.3 | 15.0 | 1.6.5 | 14.4 | 14.2 | 14.0 |
| HCT (%) | 52.1 | 52.0 | 57.4 | 49.8 | 48.7 | 48.2 |
| MC (fL) | 52.8 | 53.1 | 54.7 | 52.3 | 52.4 | 52..8 |
| MCH (pg) | 15.5 | 15.3 | 15.7 | 15.1 | 15.3 | 15.3 |
| MCHC (g/dL) | 29.4 | 28.8 | 28.7 | 28.9 | 29.2 | 29.0 |
| RDW-SD (fL) | 31.4 | 32.3 | 31.0 | 29.9 | 29.3 | 30.7 |
| RDW-CV (%) | 23.5 | 23.5 | 23.0 | 22.5 | 22.2 | 22.3 |
| RET (K/μL) | 436.3 | 470.9 | 573.3 | 487.9 | 444.5 | 454.7 |
| RET (%) | 4.42 | 4.81 | 5.46 | 5.12 | 4.78 | 4.98 |
| PLT (K/μL) | 908 | 650 | 682 | 365 | 294 | 985 |
| PDW (fL) | 7.0 | 7.0 | 7.1 | 7.8 | 8.2 | 6.6 |
| MPV (fL) | 6.2 | 6.1 | 6.5 | 6.7 | 6.9 | 6.1 |
| WBC (K/μL) | 2.25 | 1.93 | 2.21 | 3.22 | 2.73 | 3.75 |
| NEUT (K/μL) | 0 | 0.82 | 0.70 | 1.65 | 1.32 | 7.36 |
| LYMPH (K/μL) | 0.84 | 0.84 | 0.80 | 1.06 | 1.01 | 0.93 |
| MONO (K/μL) | 0.46 | 0.14 | 0.58 | 0.34 | 0.28 | 0.35 |
| EO (K/μL) | 0.09 | 0.13 | 0.12 | 0.16 | 0.10 | 0.10 |
| BASO (K/μL) | 0.00 | 0.00 | 0.01 | 0.01 | 0.02 | 0.01 |
| NEUT (%) | 38.3 | 42.5 | 31.7 | 51.2 | 48.3 | 62.9 |
| LYMPH (%) | 37.3 | 43.5 | 36.2 | 32.9 | 37.0 | 24.8 |
| MONO (%) | 20.4 | 7.3 | 262 | 10.6 | 10.3 | 9.3 |
| EO (%) | 4.0 | 6.7 | 5.4 | 5.0 | 3.7 | 2.7 |
| BASO(%) | 0.0 | 0.0 | 0.5 | 0.3 | 0.7 | 0.3 |

RBC, red blood cell;
HGB, hemoglobin concentration;
HCT, hematocrit;
MCV, mean corpuscular volume;
MCH, mean corpuscular hemoglobin;
MCHC, mean corpuscular hemoglobin concentration;
ROW-SD and ROW-CV, red blood cell distribution width standard deviation and coefficient of variance;
RET, reticuLocyte relative and absolute counts;
PLT, platelet count;
POW, platelet distribution width;
MPV, mean platelet volume;
WBC, white blood cell;
and relative and absolute counts of NEUT, neutrophils, LYMPH, lymphocytes, MONO, monocytes, EO, eosinophils, BASO, basophils Table 4 shows histopathologic profiles in tumor-bearing mice.

TABLE 4

|  | HT1080 Particle-Exposed Female | | HT1080 Saline Vehicle Female | | 786-0 Particle-Exposed Female | | 786-0 Saline Vehicle Male | |
|---|---|---|---|---|---|---|---|---|
| Tumor H&E | SQ tumor consistent with HT1080 | SQ tumor consistent with HT1080 | SQ tumor consistent with HT1080 | SQ tumor consistent with HT1080 | SQ tumor consistent with 786-0 | SQ tumor consistent with 786-0 | SQ tumor consistent with 786-0 | SQ tumor consistent with 786-0 |

TABLE 4-continued

| | HT1080 Particle-Exposed Female | | HT1080 Saline Vehicle Female | | 786-0 Particle-Exposed Female | | 786-0 Saline Vehicle Male | |
|---|---|---|---|---|---|---|---|---|
| Tumor Mac2 | Marked | Marked | Mild | Mild | Marked | Marked | ND | ND |
| Liver H&E | N. | Hepatitis, histiocytic and neutrophillic, 1, MFR; Extramedullary hematopoiesis, 1. | N. | N. | N. | N. | N. | N. |
| Kidney H&E | Cortical tubular cyst, F, U. | N. | N. | N. | N. | N. | Cortical tubular necrosis and regeneration, 1, MF, U. | N. |

SQ, subcutaneous;
N, normal;
Mac2, macrophage immunohistochemical marker;
N: Normal,
F: Focal,
FE: Focally extensive,
MF: Multifocal,
MFR: Multifocal random,
D: Diffuse,
U: Unilateral,
1: Minimal,
2: Mild,
3: Moderate,
4: Marked.

The mechanism whereby C dots contribute to ferroptosis can be determined to identify whether other kinds of nanomaterials may have similar effects to induce this form of cell death and whether other controlled variations in particle structure, composition, or surface chemical properties can alter, or even abrogate, induction of ferroptosis. Without wishing to be bound to any theory, the ability of nanoparticle-induced ferroptosis as a redox modulator of cell fate, as well as a mediator of tumor regression and growth inhibition, suggesting it can be possible to exploit this process therapeutically to synchronously and selectively kill cancers sensitive to those cancers most susceptible to this mechanism.

In certain embodiments, tumor vascularity influences particle delivery, nutrient and oxygen status, and treatment response. In certain embodiments, assessment of tumor vascularity across a variety of pre-clinical tumor types provides improved screening of models suitable for induction of cell death by ferroptosis. In certain embodiments, assessments identify appropriate combinatorial treatment paradigms.

In certain embodiments, controlled variations in C' dot properties (e.g., structure, composition, or surface chemistry) either enhance, or abrogate, induction of ferroptosis. It was found, for example, that C' dot size plays a critical role in the magnitude of the effect observed under amino acid-deprived conditions (FIG. 9A). Smaller diameter (~6 nm) PEGylated C' dots led to a significantly higher percentage of Sytox Green labeled HT-1080 cells (about 80%) cells compared to that found for larger diameter (~10 nm) C' dots (about 25%).

Further, while the response to liproxstatin-1 provides an example for ferroptosis as an anti-tumor mechanism in vivo, other mechanisms can be contributory, including but not limited to modulation of the tumor microenvironment, given marked macrophage recruitment to particle-treated tumors (FIGS. 5G and 5H, HT-1080; FIG. 9C, 786-0).

In certain embodiments, combination therapies can be administered to a subject to promote ferroptotic induction. For example, a drug (e.g., TAS-102) can be administered to tumor cells, and then a sufficiently high concentration of nanoparticles can be administered to induce ferroptosis. Details on TAS-102 can be found in "Randomized Trial of TAS-102 for Refractory Metastatic Colorectal Cancer" by R. J. Mayer et al., *NEJM*, May 14, 2015, which contents are incorporated herein by reference. Moreover, the tumor can be deprived of hormones (e.g., castration), and sufficiently high concentrations of nanoparticles administered to the tumor can induce and/or even enhance a ferroptotic cell death program relative to tumors not exposed to hormonal or inhibitor treatments.

Without wishing to be limited to any particular theory, it is postulated that hormonal castration (and/or nutrient, e.g., amino acid deprivation) causes cells to compensate by over-expressing receptors that internalize particles in the neighborhood. In certain embodiments, the effect of iron on ferroptosis can be additionally utilized. For example, in alternative embodiments, certain cell types may not need to be metabolically or hormonally deprived to internalize nanoparticles for inducement of ferroptosis.

Nanoparticle Modulation of Tumor Microenvironment and Macrophage Plasticity/Activation Distinct macrophage subsets have been linked with either protective or pathogenic roles in cancer. Classically activated, "proinflammatory" M1 phenotype macrophages have roles in anti-tumor immunity, affording a protective role in tumorigenesis. These macrophages activate tumor-killing mechanisms and antagonize the suppressive activities of tumor associated macrophages and myeloid-derived suppressive cells. M1 macrophages are activated by Toll-like receptor ligands (such as lipopolysaccharide) and interferon-T, which amplify helper T cell subtype TH1 responses, providing a positive feedback loop in the antitumor response. In addition, M1 macrophages express pro-inflammatory cytokines and inducible nitric-oxide synthase, among others. Alternatively, activated, "pro-resolving" macrophages (M2 macrophages) have anti-inflammatory function, regulating wound healing. In addition, they suppress adaptive tumor-specific immune responses and promote tumor growth, invasion, metastasis, stroma remodeling and angiogenesis.

Silica nanoparticles, without and with tumor-targeting moieties (e.g., alpha melanocyte stimulating hormone) continue to be tested in animal models for assessing cell death programs (e.g., ferroptosis) and drug therapy. As described herein, small numbers of Mac-2 positive macrophages, a murine macrophage marker were shown in the soft tissues surrounding control tumors by immunohistochemical staining, while particle-treated tumors were circumscribed by much larger numbers of Mac-2 positive cells in the same locations at both low and high magnification. This marked increase in the number of macrophages surrounding particle-treated tumors relative to that about control lesions has a role in disease protection and wound repair by engulfing cellular debris. It can be further acknowledged that macrophages are known to demonstrate a high degree of plasticity (e.g., represent a spectrum of activated phenotypes rather than discrete stable subpopulations) in response to local cues from the tumor microenvironment and can assume a spectrum of roles upon activation that are required for maintaining tissue homeostasis, including shifts in their function associated with tumor shrinkage.

The described foregoing results, as well as associated tumor growth inhibition and shrinkage, were completely unexpected for this hybrid inorganic-organic platform that combines an ultrasmall silica nanoparticle size (e.g., 6 nm) with surface functionalities of varying net charge, size, and conformation. In certain embodiments, mechanisms relating to whether these results might be attributed solely to ferroptosis, or whether immunomodulation and/or other activated metabolic/non-immune processes within the tumor microenvironment played a role can be determined. Without wishing to be bound to any theory, C dot physicochemical properties (e.g., size, charge, attached surface chemical moieties) can modulate such processes in response to local cues from the tumor microenvironment.

In certain embodiments, a protein corona (e.g., IgG, albumin, etc) is determined to form about the particle surface following systemic administration leading to phenotypic activation of macrophages (e.g., pro-inflammatory (M1) and/or pro-resolving (M2)). In certain embodiments, differences in profiles of phenotypic activation of macrophages between particles extracted in blood/plasma specimens, murine tumor tissue, ex vivo human tumor tissue specimens are determined In certain embodiments, monocyte/macrophage response to the presence of particles is determined and/or controlled. In certain embodiments, the response of other components of the tumor microenvironment to achieve tumoricidal behavior is determined and/or controlled. In certain embodiments, surface chemistry of therapeutic nanoparticles influence monocyte/macrophage responses. In certain embodiments, surface chemistry of therapeutic nanoparticles is designed to control monocyte/macrophage responses.

In certain embodiments, native and/or surface-functionalized ultrasmall silica nanoparticles (e.g., C dots) activate macrophages (e.g., M1 macrophages). In certain embodiments, high IL-12 levels are present, as IL-12 stimulates IFNγ production by TH1 cells (e.g., IL-10 levels should be low). In certain embodiments, iNOS expression and levels of TNFα, GM-CSF, and LPS are measured. In certain embodiments, transcription factors (e.g., IRF-5, STAT-1) are measured. In certain embodiments, cytokines secreted by M1 cells (e.g., IL-1, IL-6, Il-15, IL-18, and IL-23) are measured. M1 macrophages secrete pro-inflammatory cytokines and chemokines attracting other types of immune cells and integrating/orchestrating the immune response. M1 macrophages also express high levels of major histocompatibility complex (MHC), costimulatory molecules, and Fc γR.

In certain embodiments, upregulation and/or downregulation of genes linked to M1 phenotype occur. In certain embodiments, signaling pathways and/or immune effectors such as p38MAPK, p44/p42 MAPK, JNK, upregulation of CD40, CD80, CD86 (e.g., co-stimulatory molecules), and I-A/I-E activation markers (e.g., B cell activation) is effected by native and/or surface-functionalized ultrasmall silica nanoparticles.

In certain embodiments, macrophage activation depends on TLR4 (Toll-like receptor 4) and ROS signaling to kill cells. In certain embodiments, LPS-induced phenotype (e.g., expression profiling) occurs when exposed to native and/or surface-functionalized ultrasmall silica nanoparticles.

In certain embodiments, functional effects of C dots on macrophage podosomes (e.g., actin-enriched cell surface structures enabling migration and invasion by delivering factors needed for extracellular matrix degradation formation and extracellular matrix degradation activity) can be determined.

In certain embodiments, cancer-related inflammation can be targeted in patients using surface functionalized C dots.

In certain embodiments, 'bad' and 'good' inflammatory processes are altered by C dot physiochemical properties to promote adaptive immunity instead of tumor development.

In certain embodiments, drug delivery (or other therapies) are combined with native immunomodulation properties of C dots to increase the therapeutic potential of C dots in cancer treatment and/or tissue repair processes (e.g., wound healing).

In certain embodiments, dose escalation studies with the dual-modality particle probes are used to investigate improvements in targeted therapeutic delivery, penetration, and maximum treatment response over the native drug for both dasatinib-NDCs in PDGFB-driven gliomas and gefitinib-NDCs in EGFRmt+ preclinical flank/brain xenograft models; imaging findings are being confirmed histologically. Pharmacokinetic studies have also been performed with these agents to assess for unexpected toxicity and evaluate particle dosimetry. A separate cohort of mice can be injected with dual-modality particle probes to track drug vs particle delivery and distribution to monitor stability of the platform. Expected increased effective drug concentrations at tumor sites are based upon previously observed preferential tumor retention and the ability to quantitatively estimate therapeutic dosing requirements.

Cell Culture and Constructs

MEF and HT1080 cells were cultured in Dulbecco's modified Eagle's medium (DMEM) (MSKCC Media Preparation Facility) supplemented with 10% fetal bovine serum (FBS, Sigma, St. Louis, MO) with penicillin/streptomycin (Corning, Corning, NY). MCF10A cells were cultured in DMEM/F12 (Gibco, Grand Island, NY) supplemented with 5% horse serum (Atlanta Biologicals, Flowery Branch, GA), 20 ng/ml EGF (Peprotech, Rocky Hill, NJ), 10 µg/ml insulin (Sigma), 0.5 µg/ml hydrocortisone (Sigma), and 100 ng/ml cholera toxin (Sigma) with penicillin/streptomycin. M21, BxPC3, H1650, and 786-0 cells were cultured in RPMI-1640 (Gibco) supplemented with 10% FBS with penicillin/streptomycin. SKOV3 cells were cultured in McCoy's 5a modified medium (Gibco) supplemented with 10% FBS with penicillin/streptomycin. Amino acid-free medium was prepared by dialyzing heat-inactivated FBS (for MEF, HT1080, M21, BxPC3, H1650, and SKOV3 cells) or horse serum (for MCF10A cells) for 4 h, followed by overnight incubation at 4° C. in phosphate-buffered saline (PBS) in MWCO 3500 dialysis tubing (21-152-9; Fisherbrand, Pittsburgh, PA) and addition to base media prepared without amino acids. PRetro-Lamp1-GFP was introduced into M21 cells by retroviral transduction, and stable cell lines were selected with puromycin (2 µg ml$^{-1}$).

Reagents

The following reagents were used at the indicated concentrations: Concanamycin A (ConA) (Sigma) 100 nM; SYTOX Green Nucleic Acid Stain (S7020; Invitrogen, Carlsbad, CA) 5 nM; Ferrostatin-1 (Fer-1) (EMD Millipore, Billerica, MA) 1 µM; Liproxstatin-1 (Selleckchem) 1 µM and 125 mg/kg for in vitro and in vivo, respectively; Deferoxamine (DFO) (Sigma) 100 µM; Butylated hydroxyanisole (BHA) (Sigma) 50 µM; Ascorbic acid (Asc Acid) (Sigma) 200 µM; Trolox (Sigma) 100 µM; N-acetylcysteine (NAC) (Sigma) 10 mM; Glutathione (GSH) (Sigma) 5 mM; TNFα(Sigma) 100 ng/ml; Cycloheximide (CHX) (Sigma) 1 µg/ml and 50 µg/ml to induce necroptosis and apoptosis, respectively; zVAD (Sigma) 20 µM; Necrostatin-1 (Sigma) 30 µM; Buthionine sulphoximine (BSO) (Sigma) 400 µM; Ferric ammonium citrate (FAC) (Sigma, F5879) 400 µM; Erastin (Sigma), 5 µM, C11-BODIPY (581/591) 2 µM (Invitrogen). Reagents were added to cultures at the start of biological assays with the exception of ConA which was added 1 hour prior to lysis for western blotting.

Peptide Synthesis

A modified melanocortin-1 receptor targeting peptide Re(Arg11)CCMSH with a double aminohexanoic acid (Ahx2) aliphatic linker and N-Ac-Cys was synthesized using standard solid phase Fmoc peptide chemistry. The rhenium-cyclized αMSH peptide analog, Ac-Cys1-(Ahx)2-dLys2-Re[Cys-Cys-Glu-His-dPhe-Arg-Trp-Cys]-Arg-Pro-Val-NH2, was analyzed and purified on a Beckman Coulter High Performance Liquid Chromatography (HPLC) system coupled with an LCQ FLEET Ion Trap Mass spectrometer (Thermo Fisher Scientific) and finally recovered by lyophilization.

Synthesis and Characterization of α-MSH-PEG-C' Dots

αMSH is a neuroimmunomodulator, and its receptor, MC1-R, is present on macrophages. In certain embodiments, αMSH peptides are attached to nanoparticles (e.g., C' dots). In certain embodiments, α-MSH-PEG-C' dots are used for combinational therapy. For example, α-MSH-PEG-C' dots induce ferroptosis and provide immunomodulation via αMSH peptides.

Fluorescent silica nanoparticles (C' dots) of different size, encapsulating the organic dye Cy5, were synthesized in water. αMSH peptides were conjugated to maleimido-terminated silane-polyethylene glycol (PEG) via its N-terminal acetylated cysteine thiol to form α-MSH-PEG. Conjugates were attached to the particle surface in the PEGylation step to generate αMSH functionalized C' dots, or α-MSH-PEG-C' dots. Synthesized particle samples were dialyzed in water and purified by gel permeation chromatography (GPC, Bio-Rad Laboratories, Inc, Hercules, California) prior to further characterization. Absorption and emission spectral profiles for the encapsulated and native Cy5 dye were obtained using a Varian Cary 5000 spectrophotometer (Varian, Palo Alto, CA) and a fluorescence spectrofluorometer (Photon Technology International, Inc, Birmington, NJ). Hydrodynamic radius, brightness, and concentration of α-MSH-PEG-C' dots, as against free Cy5 dye, were determined using a homebuilt fluorescence correlation spectroscopy (FCS) set up configured with a solid-state 633-nm excitation.

Western Blotting

Cells were scraped into ice-cold RIPA buffer (50 mM Tris at pH 7.4, 150 mM NaCl, 2 mM EDTA, 1% NP40, 0.1% SDS with protease inhibitor cocktail) and lysed for 10 min on ice. Lysates were then centrifuged at 15,870 g for 20 min at 4° C. and protein was quantified by BCA assay (Pierce, Waltham, MA). Samples were separated on 15% polyacrylamide SDS-PAGE gels and transferred to a polyvinyldifluoride membrane which was blocked with TBST plus 5% BSA and incubated overnight at 4° C. with primary antibodies (anti-LC3A/B (4108; Cell Signaling, Danvers, MA) anti-FTH1 (3998; Cell Signaling), and anti-Actin (A1978; Sigma)), diluted in blocking buffer. Blots were incubated with horseradish peroxidase conjugated to secondary antibodies and protein was detected using enhanced chemiluminescence detection (Invitrogen). Densitometry analysis was carried out using ImageJ software (NIH).

Time-Lapse Microscopy

Cells were plated onto glass-bottom dishes (MatTek, Ashland, MA). Overnight and fluorescence and differential interference contrast (DIC) images were acquired every 30 min for indicated times using a Nikon TI-E inverted microscope, a CoolSNAP HQ$^2$ CCD (charge-coupled device) camera (Photometrics, Tucson, AZ). A live-cell incubation chamber maintained cells at 37° C. and 5% $CO_2$. NIS Elements software (Nikon, Melville, NY) was used. Cell fates, including cell survival, death, and proliferation, were manually quantified and processed using NIS Elements software and Image J.

Glutathione Quantification

For glutathione measurements, HT-1080 cells were plated on 6 cm cell culture dishes, incubated with 15 µM α-MSH-tagged nanoparticles in amino acid-free DMEM+10% dialyzed FBS and harvested approximately 2 hours before the expected time of death. As controls, cells were treated with a mix of 3 parts full or amino acid-free DMEM and 1 part $H_2O$, or 100 µM BSO in full media. Cells were washed 3× with cold PBS and harvested through cell scraping in 50 µL cold lysis buffer. Protein concentrations were measured using the BCA assay and sample volumes were adjusted so that each had the same final protein concentration. Total glutathione was measured using the Glutathione Assay Kit (Cayman Chemicals, 703002) and reduced glutathione was measured using the QuantiChrom™ Glutathione Assay Kit (BioAssay Systems, DIGT-250) according to manufacturer's instructions.

Analysis of Reactive Oxygen Species

Cells were treated with or without 15 µM α-MSH-PEG-C' dots for 24 hours, then harvested and resuspended in 500 µL Hanks Balanced Salt Solution (HBSS) (Gibco) supplemented with either $H_2DCFDA$ (25 µM) or C11-BODIPY (581/591) (2 µM) (both from Invitrogen) and incubated for 15 minutes at 37° C. Cells were then resuspended in 500 µL of fresh HBSS and analyzed using the FL1 channel of a flow cytometer (MoFlo, Beckman Coulter). Data were collected from a minimum of 10,000 cells per condition.

Iron Measurements

For iron loading capacity measurements of C' dots, 50 µL α-MSH-PEG-C' dots (60 µM) were added to either 150 µL iron-containing media (8.6 µM) or to 150 µL $FeCl_3$ solutions prepared over a range of iron ($Fe^{3+}$) concentrations (2 µM to 2 mM, Table 1). Solutions were spun at room temperature (160 rpm) for 48 hours, followed by separation of free iron from C' dots using a PD-10 column, and eluting in water.

Cellular samples were incubated with and without particles in media for 48 hours prior to centrifugation, pelleted, and washed three times prior to re-suspending in phosphate buffered saline solution. Iron measurements (parts per billion, ppb) were determined using Microwave Plasma—Atomic Emission Spectroscopy, along with iron-loading capacities. Iron loading capacity was computed as the ratio of the amount of iron in purified particle-exposed C' dots (or cells), divided by the total amount of initial iron measured prior to purification, and multiplied by 100. All experiments were performed in triplicate.

GPX4 Activity Assay

The GPX4 specific activity assay was performed according to Roveri and colleagues. Briefly, frozen cell pellets were resuspended in 100 μL lysis buffer (100 mM $KH_2PO_4$/$K_2HPO_4$, pH 7.4, 1 mM EDTA, 150 mM KCl, 0.1% CHAPS, 3 mM (3-mercaptoethanol and protease inhibitor cocktail) and homogenized by 50 pestle strokes. Samples were incubated for 15 min on ice and cell debris was removed by centrifugation (20000 g and 10 min, 4° C.). 50 μL of the supernatant from homogenized cells were used to measure the enzymatic activity in 1 ml of assay buffer (100 mM TrisHCl pH 7.8 containing 5 mM EDTA, 0.1% Triton X, 3 mM GSH, 200 μM NADPH and 0.6 U/ml glutathione reductase) in the presence of 20 μM phosphatidylcholine hydroperoxide (PCOOH). GPX4 activity is determined by the glutathione reductase-dependent consumption of NADPH detectable by a decrease in absorbance at 340 nm in a SpectraMax plate reader (Molecular Device GmbH). Protein content in the samples was determined by the colorimetric 660 nm Pierce Protein Assay method (Pierce, Waltham, MA).

Animal Models and Tumor Inoculation

All animal experiments were performed in accordance with protocols approved by the Institutional Animal Care and Use Committee of Memorial Sloan-Kettering Cancer Center and followed NIH guidelines for animal welfare. Human melanoma (M21) xenografts were generated on the shaved flanks of immunodeficient male SCID/Beige (C.B-17/IcrHsd-Prkdc$^{scid}$Lyst$^{bg-J}$) mice (6-8 weeks old; Harlan Laboratories, South Easton, MA). Human sarcoma HT1080 and 786-0 flank xenografts (~2=10$^6$ cells/100 μl) were additionally generated using the same model for intravenous particle injection. Average initial tumor volumes of 45-75 mm$^3$ were used for all experiments.

In Vivo Dosing Strategy and Examination

Five million M21 cells, cultured in serum-supplemented media, were subcutaneously implanted into the right flank of mice using a 23-gauge trocar needle to establish melanoma xenografts 2 days after particle exposure (n=3) or without exposure (n=3). In a subsequent study, mice were assigned to one of two different treatment groups to evaluate the response of HT-1080 and 786-0 tumors to high-concentrations (60 μM) of i.v.-injected α-MSH-PEG-C' dots (n=5 mice; 200 μl) administered three times over a 10-day period (i.e., days 0, 4, 7). Control HT-1080 and 786-0 mice (n=3) were administered 0.9% saline vehicle at the same time points. In a third treatment study, HT-1080 mice were assigned to one of two groups to evaluate response to three, high-concentration doses (60 μM) of i.v.-injected α-MSH-PEG-C' dot (n=3 mice; 200 μl) alone or following intraperitoneal administration of liproxstatin-1 (n=3 mice, 125 mg/kg) over a 10-day period. Tumor sizes were measured using calipers over the treatment interval. All mice were examined by palpation at the site of tumor cell inoculation, and were observed daily over until the termination of tumor growth studies for signs of morbidity or mortality. Two perpendicular diameters ($d_1 \leq d_2$) of the tumor used to calculate the tumor volume (V; $\frac{4}{3} \cdot \pi \cdot d_1^2 \cdot d_2/8$) were measured with calipers daily following the injection of cells.

Fluorescence Imaging

Animals were anesthetized using isoflurane and whole body optical fluorescence imaging was acquired to identify nanoparticle fluorescence at the tumor site. Mice were scanned for 0.1 to 1 seconds using the IVIS Spectrum photon-counting device optical imaging system (Xenogen, Alameda, CA) with the blocks and filters for Cy5 fluorescence (excitation 650 nm, emission 680 nm) and for background fluorescence (excitation 465 nm, emission 600 nm), selected according to the manufacturer's recommendations. Fluorescence background was likewise subtracted according to the manufacturers' instructions. Fluorescence signal was reported as radiant efficiency ((photons/s/cm$^2$/sr)/(mW/cm$^2$).

Histopathologic Analysis

Immediately after terminating the in vivo imaging study, HT-1080 and 786-0 male and female mice were euthanized by $CO_2$ inhalation, and representative particle-exposed (n=2) and control (n=1) tumors, as well as hepatic and renal specimens, were excised at necropsy. Hematologic specimens were additionally obtained for complete blood counts and serum chemistries. Excised tumors, livers, and kidneys were fixed in 10% neutral buffered formalin for 24 hours, processed in alcohol and xylene, embedded in paraffin, sectioned at 5-micron thickness, and stained with hematoxylin and eosin (H&E). Additional sections were stained by immunohistochemistry for Mac-2 (primary antibody Cedarlane CL8942B applied at concentration of 1:100 following heat-induced epitope retrieval [HIER] in a pH 6.0 buffer), myeloperoxidase (Dako A0398, 1:1000, HIER pH 6.0), cleaved caspase-3 (Cell Signaling Technology 9661, 1:250, HIER pH6.0), and Ki-67 (Abcam ab16667, 1:100, HIER pH 9.0). Mac-2 staining was performed manually with an avidin-biotin detection system (Vectastain ABC Elite Kit, Vector Laboratories, PK-6100). Other stains were performed on a Leica Bond RX automated stainer using the Bond Polymer Refine detection kit (Leica Biosystem DS9800). Tumor sections were also stained by the TUNEL method as previously described. All slides were examined by a board-certified veterinary pathologist.

Tumor Vascularity Assessment

Tumor vascularity was assessed by staining HT-1080 tumors by immunohistochemistry for CD31 on a Leica Bond RX automated staining platform (Leica Biosystems). Following heat-induced epitope retrieval at pH 9.0, the primary antibody (rat monoclonal, catalog #DIA-310; Dianova) was applied at a concentration of 1:250 and was followed by application of a polymer detection system (Novocastra Bond Polymer Refine Detection, Leica Biosystems).

Statistics

Volume-time profiles were compared between the two treatment groups using robust standard errors calculated using by a generalized estimating equations approach. Particle-treated tumor growth profiles, with and without a pharmacological inhibitor to ferroptosis, liproxstatin-1, were compared using a linear model. The longitudinal aspect of the data was taken into account by using generalized estimating equations. Statistical significance was assigned to be $P<0.05$.

What is claimed is:

1. A method of treatment of a subject, the method comprising:
  administering nanoparticles at an administered concentration greater than 1 μM to activate the tumor microenvironment, characterized by a pro-inflammatory response surrounding or within tumor tissue as compared to non-treated tumor tissue;
wherein the administered nanoparticles have an average diameter no greater than 15 nm, and
wherein the administered nanoparticles comprise a core comprising silica and a silica shell surrounding at least a portion of the core.

2. The method of claim 1, wherein the pro-inflammatory response comprises an activation of macrophages.

3. The method of claim 1, wherein the tumor tissue is glutathione depleted.

4. The method of claim 1, wherein the tumor tissue comprises an accumulation of lipid peroxidation.

5. The method of claim 1, the method comprising depriving a tumor tissue of hormones.

6. The method of claim 5, wherein the tumor tissue is deprived of hormones via castration.

7. The method of claim 1, wherein the tumor tissue is selected from the group consisting of renal, prostate, melanoma, pancreatic, lung, fibrosarcoma, breast, brain, ovarian, and colon tumor tissue.

8. The method of claim 7, wherein the tumor pancreatic tissue comprises BxPC3 cells.

9. The method of claim 7, wherein the tumor lung tissue comprises H1650 cells.

10. The method of claim 1, wherein the nanoparticles have an average diameter no greater than 10 nm.

11. The method of claim 1, wherein the nanoparticles have an average diameter from about 5 nm to about 7 nm.

12. The method of claim 1, wherein the nanoparticles comprise from 1 to 20 targeting moieties, wherein the targeting moieties bind to receptors on cells.

13. The method of claim 1, wherein the nanoparticles comprise from 1 to 20 targeting moieties, wherein the 1 to 20 targeting moieties comprises alpha-melanocyte-stimulating hormone (αMSH).

14. The method of claim 1, wherein the nanoparticles comprise a targeting moiety.

15. The method of claim 1, wherein the nanoparticles are administered multiple times over the course of treatment.

16. The method of claim 1, further comprising administering the nanoparticles every 3 or 4 days over the course of treatment.

17. The method of claim 1, wherein cells of the tumor tissue comprise an intracellular concentration of iron of 8.3 parts per billion (ppb) or higher.

18. The method of claim 1, wherein cells of the tumor tissue comprise an intracellular concentration of iron of 144.7 parts per billion (ppb) or higher.

19. The method of claim 1, wherein cells of the tumor tissue comprise an intracellular concentration of iron of 2.58 µM or higher.

* * * * *